United States Patent
Langer et al.

(10) Patent No.: US 9,067,919 B2
(45) Date of Patent: Jun. 30, 2015

(54) USE OF DIBENZOFURANS AND DIBENZOTHIOPHENES SUBSTITUTED BY NITROGEN-BONDED FIVE-MEMBERED HETEROCYCLIC RINGS IN ORGANIC ELECTRONICS

(75) Inventors: Nicolle Langer, Heppenheim (DE); Christian Schildknecht, Mannheim (DE); Christian Lennartz, Schifferstadt (DE); Gerhard Wagenblast, Wachenheim (DE); Thomas Schäfer, Liestal (CH)

(73) Assignee: BASF SE, Ludwigshafen (DE)

( * ) Notice: Subject to any disclaimer, the term of this patent is extended or adjusted under 35 U.S.C. 154(b) by 334 days.

(21) Appl. No.: 13/179,061

(22) Filed: Jul. 8, 2011

(65) Prior Publication Data
US 2012/0007063 A1 Jan. 12, 2012

Related U.S. Application Data

(60) Provisional application No. 61/362,314, filed on Jul. 8, 2010.

(51) Int. Cl.
*H01L 51/50* (2006.01)
*C07D 405/14* (2006.01)
*C07D 405/04* (2006.01)
*H01L 51/00* (2006.01)

(52) U.S. Cl.
CPC ............ *C07D 405/14* (2013.01); *C07D 405/04* (2013.01); *H01L 51/0073* (2013.01); *H01L 51/0085* (2013.01); *H01L 51/0094* (2013.01); *H01L 51/5016* (2013.01); *H01L 51/5048* (2013.01); *H01L 51/5096* (2013.01)

(58) Field of Classification Search
None
See application file for complete search history.

(56) References Cited

U.S. PATENT DOCUMENTS

| | | |
|---|---|---|
| 2003/0137239 A1* | 7/2003 | Matsuura et al. ............. 313/503 |
| 2009/0079340 A1 | 3/2009 | Kinoshita et al. |
| 2009/0284134 A1 | 11/2009 | Iida et al. |
| 2010/0258767 A1 | 10/2010 | Matsunami et al. |
| 2010/0264405 A1 | 10/2010 | Molt et al. |
| 2011/0006670 A1 | 1/2011 | Katakura et al. |
| 2011/0049496 A1 | 3/2011 | Fukuzaki |
| 2011/0204333 A1 | 8/2011 | Xia et al. |
| 2012/0309980 A1 | 12/2012 | Kinoshita et al. |

FOREIGN PATENT DOCUMENTS

| | | |
|---|---|---|
| EP | 1 956 008 A1 | 8/2008 |
| EP | 2 042 508 A1 | 4/2009 |
| JP | 2007-217397 | 8/2007 |
| JP | 2008-303150 | 12/2008 |
| JP | 2010-118591 | 5/2010 |
| JP | 2010-135467 | 6/2010 |
| JP | 2010-238880 | 10/2010 |
| JP | 2010-254642 | 11/2010 |
| JP | 2010-267847 | 11/2010 |
| WO | WO 03/105538 A1 | 12/2003 |
| WO | WO 2005/054212 A2 | 6/2005 |
| WO | WO 2005/113704 A2 | 12/2005 |
| WO | WO 2006/114377 A1 | 11/2006 |
| WO | WO 2006/128800 A1 | 12/2006 |
| WO | WO 2009/050281 A1 | 4/2009 |
| WO | WO 2010/079051 A1 | 7/2010 |
| WO | WO 2010/116759 A1 | 10/2010 |
| WO | WO 2011/010840 A1 | 1/2011 |
| WO | WO 2011/106344 A1 | 9/2011 |

OTHER PUBLICATIONS

Huang et al., Tuning the Optoelectronic Properties of 4,4'-N,N'-Dicarbazole-biphenyl through Heteroatom Linkage: New Host Materials for Phosphorescent Organic Light-Emitting Devices, Organic Letters, 2010, vol. 12, No. 15, pp. 3488-3441.*
U.S. Appl. No. 14/123,530, filed Dec. 3, 2013, Koenemann, et al.
M. A. Baldo, et al., "Very High-Efficiency Green Organic Light-Emitting Devices Based on Electrophosphorescence", Applied Physics Letters, vol. 75, No. 1, Jul. 5, 1999, 3 pages.
Yvonne Unger, et al., "Green-Blue Emitters: NHC-Based Cyclometalated [Pt(CC*)(acac)] Complexes", Angewandte Chemie International Edition, 49, 2010, 3 pages.
U.S. Appl. No. 14/115,934, filed Nov. 6, 2013, Wagenblast, et al.
Extended European Search Report issued Feb. 3, 2014 in Patent Application No. 11803227.5.

* cited by examiner

*Primary Examiner* — Gregory Clark
(74) *Attorney, Agent, or Firm* — Oblon, McClelland, Maier & Neustadt, L.L.P.

(57) ABSTRACT

The present invention relates to the use of dibenzofurans and dibenzothiophenes which have at least one nitrogen-bonded five-membered heterocyclic ring as a substituent as host, blocker and/or charge transport material in organic electronics. The present invention further relates to dibenzofurans and dibenzothiophenes which comprise at least one nitrogen-bonded five-membered heterocyclic ring and at least one carbazolyl radical as substituents, to a process for preparation thereof, and to the use of these compounds in organic electronics.

49 Claims, No Drawings

USE OF DIBENZOFURANS AND DIBENZOTHIOPHENES SUBSTITUTED BY NITROGEN-BONDED FIVE-MEMBERED HETEROCYCLIC RINGS IN ORGANIC ELECTRONICS

The present invention relates to the use of dibenzofurans and dibenzothiophenes which have at least one nitrogen-bonded five-membered heterocyclic ring as a substituent as host, blocker and/or charge transport material in organic electronics. The present invention further relates to dibenzofurans and dibenzothiophenes which comprise at least one nitrogen-bonded five-membered heterocyclic ring and at least one carbazolyl radical as substituents, to a process for preparation thereof, and to the use of these compounds in organic electronics.

Organic electronics is a subfield of electronics which uses electronic circuits which comprise polymers or smaller organic compounds. Fields of use of organic electronics are the use of polymers or smaller organic compounds in organic light-emitting diodes (OLEDs), use in organic solar cells (organic photovoltaics) and in switching elements such as organic transistors, for example organic FETs and organic TFTs.

The use of suitable novel organic materials thus allows various new types of components based on organic electronics to be provided, such as displays, sensors, transistors, data stores or photovoltaic cells. This makes possible the development of new applications which are thin, light, flexible and producible at low cost.

A preferred field of use according to the present application is the use of relatively small organic compounds in organic light-emitting diodes.

Organic light-emitting diodes (OLEDs) exploit the property of materials of emitting light when they are excited by electrical current. OLEDs are of particular interest as an alternative to cathode ray tubes and liquid-crystal displays for producing flat visual display units. Owing to the very compact design and the intrinsically low power consumption, the devices comprising OLEDs are suitable especially for mobile applications, for example for applications in cellphones, laptops, etc., and for illumination.

The basic principles of the way in which OLEDs work and suitable structures (layers) of OLEDs are specified, for example, in WO 2005/113704 and the literature cited therein.

The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (M. A. Baldow et al., Appl. Phys. Lett. 1999, 75, 4 to 6). For quantum-mechanical reasons, when the phosphorescence emitters are used, up to four times the quantum efficiency, energy efficiency and power efficiency is possible.

Of particular interest are organic light-emitting diodes with long operative lifetime, good efficiency, high stability to thermal stress and a low use and operating voltage.

In order to implement the aforementioned properties in practice, it is not only necessary to provide suitable emitter materials, but the other components of the OLED (complementary materials) must also be balanced to one another in suitable device compositions. Such device compositions may, for example, comprise specific matrix materials in which the actual light emitter is present in distributed form. In addition, the compositions may comprise blocker materials, it being possible for hole blockers, exciton blockers and/or electron blockers to be present in the device compositions. Additionally or alternatively, the device compositions may further comprise hole injection materials and/or electron injection materials and/or charge transport materials such as hole conductor materials and/or electron conductor materials. The selection of the aforementioned materials which are used in combination with the actual light emitter has a significant influence on parameters including the efficiency and the lifetime, and the use and operating voltages, of the OLEDs.

The prior art proposes numerous different materials for use in the different layers of OLEDs.

WO 2006/128800 A1 discloses an electroluminescent component comprising a dibenzofuran derivative which may bear amino substituents among others. Corresponding derivatives which have nitrogen-comprising five-membered heterocyclic rings in the 2 and/or 4 position are not disclosed explicitly in this document.

WO 2006/114377 A1 discloses triazoles which may be substituted by aromatics, especially dibenzofurans. The triazoles are bonded to dibenzofuran in the 3 position. No dibenzofuran or dibenzothiophene compounds substituted in the 2 and/or 4 position are disclosed explicitly.

WO 2005/054212 A1 and WO 2003/105538 A1 disclose dibenzofuran derivatives which may be 3-substituted by five-membered nitrogen heterocycles. Dibenzofuran derivatives 2- and 4-substituted by five-membered nitrogen heterocycles are not mentioned in this document.

There is additionally known prior art in which corresponding nitrogen heterocycle-substituted dibenzofurans or dibenzothiophenes are used as ligands in metal complexes.

US 2009/079340 A1 discloses, for example, the following compounds:

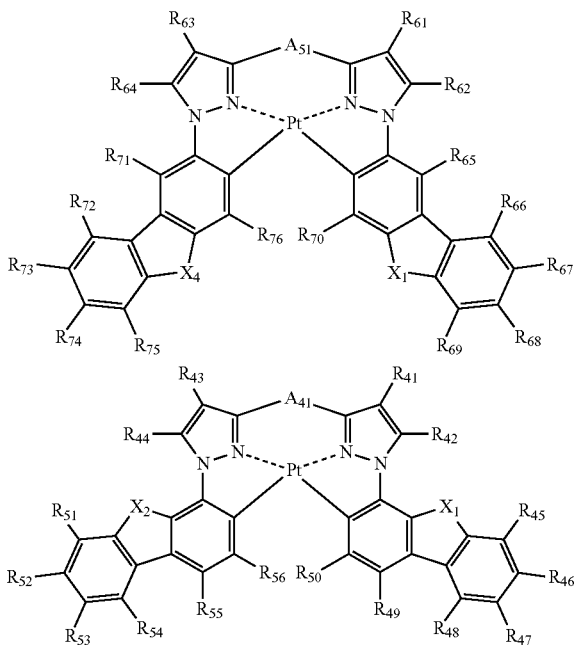

Formula (IV)

JP 2007/217397 discloses the following precursors for ligands:

(34)

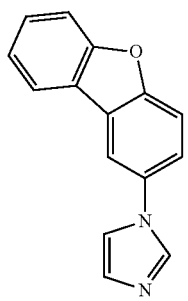

(59)

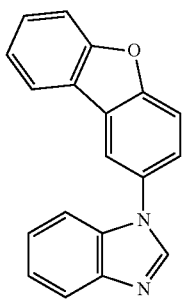

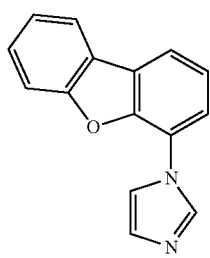

Neither document discloses use as a complementary material (see definition above). Compounds with additional carbazole substitution on dibenzofuran or dibenzothiophene are not disclosed explicitly.

JP 2008/303150 discloses likewise correspondingly substituted dibenzofurans or dibenzothiophenes, where the heterocycle in these compounds is not bonded via nitrogen.

It is thus evident from the prior art that there are known dibenzofuran and dibenzothiophene derivatives which are used especially as fluorescence emitters, and optionally as matrix material, in a light-emitting layer. In addition, corresponding dibenzofuran derivatives are known, which have a nitrogen-comprising substituent in the 2 or 4 position, and are present as ligands in metal complexes.

It is an object of the present invention, with respect to the aforementioned prior art, to provide further materials suitable for use in OLEDs and further applications in organic electronics. More particularly, host, blocker and/or charge transport materials for use in OLEDs shall be provided. In addition, the materials shall be suitable for providing OLEDs which ensure good efficiencies, good operative lifetimes and a high stability to thermal stress, and a low use and operating voltage of the OLEDs.

These objects are achieved in accordance with the invention by the use of compounds of the formula (I)

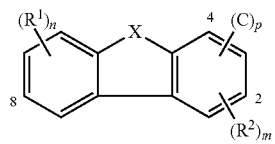

in which
X is S or O;
$R^1$, $R^2$ are each independently aryl, heteroaryl, alkyl, cycloalkyl, heterocycloalkyl, a crosslinkable or polymerizable group bonded via a spacer, $-NR^3R^4$, $-P(O)R^5R^6$, $-S(O)_2R^9$, $-S(O)R^{10}$, $-SR^{11}$ or $-OR^{12}$, or a C group;
$R^3$, $R^4$ are each independently aryl, heteroaryl, alkyl, cycloalkyl or heterocycloalkyl, a crosslinkable or polymerizable group bonded via a spacer,
or $R^3$ and $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;
$R^5$, $R^6$,
$R^7$, $R^8$,
$R_9$, $R_{10}$,
$R^{11}$, $R_{12}$ are each independently aryl, heteroaryl, alkyl, cycloalkyl or heterocycloalkyl, a crosslinkable or polymerizable group bonded via a spacer,
n is 0, 1, 2, 3 or 4,
m is 0, 1, 2 or 3,
p is 1 or 2, where m+p is ≤4,
C is a five-membered saturated or unsaturated heterocyclic radical of the general formula (II)

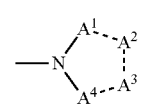

where
$A^1$ are each independently $CR^a$, N or $NR^b$;
$A^2$ are each independently $CR^c$, N or $NR^d$;
$A^3$ are each independently $CR^e$, N or $NR^f$;
$A^4$ are each independently $CR^g$, N or $NR^h$
$R^a$, $R^b$,
$R^c$, $R^d$,
$R^e$, $R^f$,
$R^g$, $R^h$ are each independently hydrogen, aryl, heteroaryl, alkyl, cycloalkyl, heterocycloalkyl, a crosslinkable or polymerizable group bonded via a spacer;
or
($R^a$ or $R^b$) and ($R^c$ or $R^d$), or
($R^e$ or $R^f$) and ($R^g$ or $R^h$), and/or
($R^c$ or $R^d$) and ($R^e$ or $R^f$)
form, together with the carbon or nitrogen atom, a cyclic radical which has 3 to 10 ring atoms and may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;

where the C group is bonded in the 2 and/or 4 position, or two units of the general formula (I) are bridged to one another via a bond, a linear or branched, saturated or unsaturated bridge optionally interrupted by at least one heteroatom or via O, where this bridge in the general formula (I) is bonded in place of $R^a$, $R^b$, $R^c$, $R^d$, $R^e$, $R^f$, $R^g$, $R^h$ or via and/or in place of $R^1$ or $R^2$, in monomeric, polymerized or crosslinked form, as host, blocker and/or charge transport materials.

The objects of the invention are also achieved by compounds of the general formula (III)

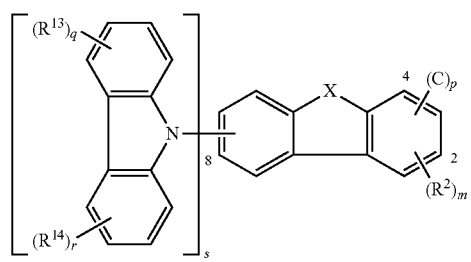

in which
X is S or O;
$R^2$ are each independently aryl, heteroaryl, alkyl, cycloalkyl, heterocycloalkyl, a crosslinkable or polymerizable group bonded via a spacer, $-NR^3R^4$, $-P(O)R^5R^6$, $-PR^7R^8$, $-S(O)_2R^9$, $-S(O)R^{10}$, $-SR^{11}$ or $-OR^{12}$,
$R^3$, $R^4$ are each independently aryl, heteroaryl, alkyl, cycloalkyl or heterocycloalkyl, a crosslinkable or polymerizable group bonded via a spacer,
or $R^3$ and $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, and a group with donor or acceptor action;
$R^5$, $R^6$,
$R^7$, $R^8$,
$R^9$, $R^{10}$,
$R^{11}$, $R^{12}$ are each independently aryl, heteroaryl, alkyl, cycloalkyl or heterocycloalkyl, a crosslinkable or polymerizable group bonded via a spacer,
$R^{13}$, $R^{14}$ are each independently aryl, heteroaryl, alkyl, cycloalkyl, heterocycloalkyl, a crosslinkable or polymerizable group bonded via a spacer, $-NR^3R^4$, $-P(O)R^5R^6$, $-PR^7R^8$, $-S(O)_2R^9$, $-S(O)R^{10}$, $-SR^{11}$ or $-OR^{12}$,
m is 0, 1, 2 or 3,
p is 1 or 2, where m+p is ≤4,
q is 0, 1, 2, 3 or 4,
r is 0, 1, 2, 3 or 4,
s is 1, 2, 3 or 4,
C is a five-membered saturated or unsaturated heterocyclic radical of the general formula (II)

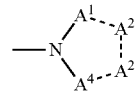

where
$A^1$ are each independently $CR^a$, N or $NR^b$;
$A^2$ are each independently $CR^c$, N or $NR^d$;
$A^3$ are each independently $CR^e$, N or $NR^f$;
$A^4$ are each independently $CR^g$, N or $NR^h$
$R^a$, $R^b$,
$R^c$, $R^d$,
$R^e$, $R^f$,
$R^g$, $R^h$ are each independently hydrogen, aryl, heteroaryl, alkyl, cycloalkyl, heterocycloalkyl, a crosslinkable or polymerizable group bonded via a spacer;
or
($R^a$ or $R^b$) and ($R^c$ or $R^d$), or
($R^e$ or $R^f$) and ($R^g$ or $R^h$), and/or
($R^c$ or $R^d$) and ($R^e$ or $R^f$)
form, together with the carbon or nitrogen atom, a cyclic radical which has 3 to 10 ring atoms and may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;
where the C group is bonded in the 2 and/or 4 position, or
two units of the general formula (III) are bridged to one another via a bond, a linear or branched, saturated or unsaturated bridge optionally interrupted by at least one heteroatom or via O, where this bridge in the general formula (III) is bonded in place of $R^a$, $R^b$, $R^c$, $R^d$, $R^e$, $R^f$, $R^g$, $R^h$, $R^{13}$, $R^{14}$ or via and/or in place of $R^2$.

It has been found that the specific heterocycle-substituted dibenzofuran and dibenzothiophene compounds of the formula (I) or (III) are particularly suitable for use in applications in which charge carrier conductivity is required, especially for use in organic electronics applications, for example selected from switching elements such as organic transistors, e.g. organic FETs and organic TFTs, organic solar cells and organic light-emitting diodes (OLEDs), the compounds of the formula (I) and (III) being particularly suitable for use as matrix material in a light-emitting layer and/or as hole and/or exciton blocker material and/or as electron and/or exciton blocker material and/or as electron conductor material, especially in combination with a phosphorescence emitter. Use of the inventive compounds of the formula (I) or (III) in OLEDs gives OLEDs which have good efficiencies and a long lifetime and which can be operated especially at a low use and operating voltage. The inventive compounds of the formula (III) are especially suitable for use as matrix and/or hole/exciton blocker materials for blue and green emitters, for example light blue or deep blue emitters, these being especially phosphorescence emitters. As electron conductors, the inventive compounds can be used in OLEDs with all colors known to those skilled in the art. In addition, the compounds of the formula (I) or (III) can be used in organic electronics applications selected from switching elements and organic solar cells.

In the context of the present application, the terms aryl radical or group, heteroaryl radical or group, alkyl radical or group, cycloalkyl radical or group, heterocycloalkyl radical or group, alkenyl radical or group, alkynyl radical or group, aralkyl radical or group, and groups with donor and/or acceptor action are each defined as follows:

An aryl radical (or group) is understood to mean a radical which has a base skeleton of 6 to 30 carbon atoms, preferably 6 to 18 carbon atoms, and which is formed from an aromatic ring or a plurality of fused aromatic rings. Suitable base skeletons are, for example, phenyl, naphthyl, anthracenyl or phenanthrenyl, indenyl or fluorenyl. This base skeleton may be unsubstituted (i.e. all carbon atoms which are substitutable bear hydrogen atoms) or be substituted at one, more than one or all substitutable positions of the base skeleton.

Suitable substituents are, for example, deuterium, alkoxy radicals, aryloxy radicals, alkylamino groups, arylamino groups, carbazolyl groups, silyl groups, $SiR^{16}R^{17}R^{18}$, suitable silyl groups $SiR^{16}R^{17}R^{18}$ being specified below, alkyl radicals, preferably alkyl radicals having 1 to 8 carbon atoms, more preferably methyl, ethyl or i-propyl, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals and carbazolyl radicals, alkenyl radicals, preferably alkenyl radicals which bear one double bond, more preferably alkenyl radicals with one double bond and 1 to 8 carbon atoms, alkynyl radicals, preferably alkynyl radicals with one triple bond, more preferably alkynyl radicals with one triple bond and 1 to 8 carbon atoms, or groups with donor or acceptor action, or crosslinkable or polymerizable groups bonded via a spacer. Suitable groups with donor or acceptor action are specified below. Most preferably, the substituted aryl radicals bear substituents selected from the group consisting of methyl, ethyl, isopropyl, alkoxy, heteroaryl, halogen, pseudohalogen and amino, preferably arylamino. The aryl radical or the aryl group is preferably a $C_6$-$C_{18}$-aryl radical, more preferably a $C_6$-aryl radical, which is optionally substituted by at least one or more than one of the aforementioned substituents. More preferably, the $C_6$-$C_{18}$-aryl radical, preferably $C_6$-aryl radical, has none, one, two, three or four, most preferably none, one or two, of the aforementioned substituents.

A heteroaryl radical or a heteroaryl group is understood to mean radicals which differ from the aforementioned aryl radicals in that, in the base skeleton of the aryl radicals, at least one carbon atom is replaced by a heteroatom, and in that the base skeleton of the heteroaryl radicals has preferably 5 to 18 ring atoms. Preferred heteroatoms are N, O and S. Particularly preferred suitable heteroaryl radicals are nitrogen-containing heteroaryl radicals. Most preferably, one or two carbon atoms of the base skeleton are replaced by heteroatoms, preferably nitrogen. Especially preferably, the base skeleton is selected from systems such as pyridine, pyrimidine and five-membered heteroaromatics such as pyrrole, furan, pyrazole, imidazole, thiophene, oxazole, thiazole, triazole. In addition, the heteroaryl radicals may be fused ring systems, for example benzofuryl, benzothienyl, benzopyrrolyl, dibenzofuryl, dibenzothienyl, phenanthrolinyl, carbazolyl radicals, azacarbazolyl radicals or diazacarbazoyl radicals. The base skeleton may be substituted at one, more than one or all substitutable positions of the base skeleton. Suitable substituents are the same as have already been specified for the aryl groups.

An alkyl radical or an aryl group is understood to mean a radical having 1 to 20 carbon atoms, preferably 1 to 10 carbon atoms, more preferably 1 to 8 and most preferably 1 to 4 carbon atoms. This alkyl radical may be branched or unbranched and optionally interrupted by one or more heteroatoms, preferably Si, N, O or S, more preferably N, O or S. In addition, this alkyl radical may be substituted by one or more of the substituents mentioned for the aryl groups. In addition, the alkyl radicals present in accordance with the invention may have at least one halogen atom, for example F, Cl, Br or I, especially F. In a further embodiment, the alkyl radicals present in accordance with the invention may be fully fluorinated. It is likewise possible that the alkyl radical bears one or more (hetero)aryl groups. In the context of the present application, for example, benzyl radicals are thus substituted alkyl radicals. All of the (hetero)aryl groups listed above are suitable. The alkyl radicals are more preferably selected from the group consisting of methyl, ethyl, isopropyl, n-propyl, n-butyl, isobutyl and tert-butyl; very particular preference is given to methyl and ethyl.

A cycloalkyl radical or a cycloalkyl group is understood to mean a radical having from 3 to 20 carbon atoms, preferably from 3 to 10 carbon atoms, more preferably from 3 to 8 carbon atoms. This base skeleton may be unsubstituted (i.e. all carbon atoms which are substitutable bear hydrogen atoms) or be substituted at one, more than one or all substitutable positions of the base skeleton. Suitable substituents are the groups already specified above for the aryl radicals. It is likewise possible that the cycloalkyl radical bears one or more (hetero)aryl groups. Examples of suitable cycloalkyl radicals are cyclopropyl, cyclopentyl and cyclohexyl.

A heterocycloalkyl radical or a heterocycloalkyl group is understood to mean radicals which differ from the aforementioned cycloalkyl radicals in that, in the base skeleton of the cycloalkyl radicals, at least one carbon atom is replaced by a heteroatom. Preferred heteroatoms are N, O and S. Most preferably, one or two carbon atoms of the base skeleton of the cycloalkyl radicals are replaced by heteroatoms. Examples of suitable heterocycloalkyl radicals are radicals derived from pyrrolidine, piperidine, piperazine, tetrahydrofuran, dioxane.

An alkenyl radical or an alkenyl group is understood to mean a radical which corresponds to the aforementioned alkyl radicals having at least two carbon atoms, with the difference that at least one C—C single bond of the alkyl radical is replaced by a C—C double bond. The alkenyl radical preferably has one or two double bonds.

An alkynyl radical or an alkynyl group is understood to mean a radical which corresponds to the aforementioned alkyl radicals having at least two carbon atoms, with the difference that at least one C—C single bond of the alkyl radical is replaced by a C—C triple bond. The alkynyl radical preferably has one or two triple bonds.

An $SiR^{16}R^{17}R^{18}$ group is understood to mean a silyl radical in which $R^{16}$, $R^{17}$ and $R^{18}$ are each independently alkyl, cycloalkyl, heterocycloalkyl, aryl, heteroaryl or $OR^{22}$.

An $SiR^{23}R^{24}R^{25}$ group is understood to mean a silyl radical in which $R^{23}$, $R^{24}$ and $R^{25}$ are each independently alkyl, cycloalkyl, heterocycloalkyl, aryl, heteroaryl or $OR^{22}$.

In the context of the present application, a group or a substituent with donor or acceptor action is understood to mean the following groups:

Groups with donor action are understood to mean groups which have a +I and/or +M effect, and groups with acceptor action are understood to mean groups which have a −I and/or −M effect. Preferred suitable groups are selected from $C_1$-$C_{20}$-alkoxy, $C_6$-$C_{30}$-aryloxy, $C_6$-$C_{30}$-arylthio, $SiR^{19}R^{20}R^{21}$, $OR^{22}$, halogen radicals, halogenated $C_1$-$C_{20}$-alkyl radicals, carbonyl (—CO($R^{19}$)), carbonylthio (—C=O (S$R^{19}$)), carbonyloxy (—C=O(O$R^{19}$)), oxycarbonyl (—OC=O($R^{19}$)), thiocarbonyl (—SC=O($R^{19}$)), amino (—N$R^{19}R^{20}$), pseudohalogen radicals, amido (—C=O (N$R^{19}$)), —N$R^{19}$C=O($R^{21}$), phosphonate (—P(O)(O$R^{19}$)$_2$, phosphate (—OP(O)O$R^{19}$)$_2$), phosphine (—P$R^{19}R^{20}$), phosphine oxide (—P(O)$R^{19}$)$_2$), sulfate (—OS(O)$_2$O$R^{19}$), sulfoxide (—S(O)$R^{19}$), sulfonate (—S(O)$_2$O$R^{19}$), sulfonyl (—S(O)$_2$ $R^{19}$, sulfonamide (—S(O)$_2$N$R^{19}R^{20}$), NO$_2$, boronic esters (—OB(O$R^{19}$)$_2$), imino (—C=N$R^{19}R^{20}$), borane radicals, stannane radicals, hydrazine radicals, hydrazone radicals, oxime radicals, nitroso groups, diazo groups, vinyl groups, sulfoximines, alanes, germanes, boroximes and borazines.

The $R^{19}$, $R^{20}$ and $R^{21}$ radicals mentioned in the aforementioned groups with donor or acceptor action are each independently:
substituted or unsubstituted $C_1$-$C_{20}$-alkyl or substituted or unsubstituted $C_6$-$C_{30}$-aryl, or $OR^{22}$, suitable and preferred alkyl and aryl radicals having been specified above. The $R^{19}$, $R^{20}$ and $R^{21}$ radicals are more preferably each $C_1$-$C_6$-alkyl, e.g. methyl, ethyl or i-propyl, or phenyl. In a preferred embodiment—in the case of $SiR^{19}R^{20}R^{21}$—$R^{19}$, $R^{20}$ and $R^{21}$ are preferably each independently substituted or unsubstituted $C_1$-$C_{20}$-alkyl or substituted or unsubstituted aryl, preferably phenyl.

Preferred substituents with donor or acceptor action are selected from the group consisting of:
$C_1$- to $C_{20}$-alkoxy, preferably $C_1$-$C_6$-alkoxy, more preferably ethoxy or methoxy; $C_6$-$C_{30}$-aryloxy, preferably $C_6$-$C_{10}$-aryloxy, more preferably phenyloxy; $SiR^{19}R^{20}R^{21}$ where $R^{19}$, $R^{20}$ and $R^{21}$ are preferably each independently substituted or unsubstituted alkyl or substituted or unsubstituted aryl, preferably phenyl; more preferably, at least one of the $R^{19}$, $R^{20}$ and $R^{21}$ radicals is substituted or unsubstituted phenyl, suitable substituents having been specified above; halogen radicals, preferably F, Cl, more preferably F, halogenated $C_1$-$C_{20}$-alkyl radicals, preferably halogenated $C_1$-$C_6$-alkyl radicals, most preferably fluorinated $C_1$-$C_6$-alkyl radicals, e.g. $CF_3$, $CH_2F$, $CHF_2$ or $C_2F_5$; amino, preferably dimethylamino, diethylamino or diarylamino, more preferably diarylamino; pseudohalogen radicals, preferably CN, —C(O) OC$_1$-$C_4$-alkyl, preferably —C(O)OMe, P(O)R$_2$, preferably P(O)Ph$_2$.

Very particularly preferred substituents with donor or acceptor action are selected from the group consisting of methoxy, phenyloxy, halogenated $C_1$-$C_4$-alkyl, preferably $CF_3$, $CH_2F$, $CHF_2$, $C_2F_5$, halogen, preferably F, CN, $SiR^{19}R^{20}R^{21}$, suitable $R^{19}$, $R^{20}$ and $R^{21}$ radicals already having been specified, diarylamino (N$R^{19}R^{20}$, where $R^{19}$, $R^{20}$ are each $C_6$-$C_{30}$-aryl), —C(O)OC$_1$-$C_4$-alkyl, preferably —C(O) OMe, P(O)Ph$_2$.

Halogen groups are preferably understood to mean F, Cl and Br, more preferably F and Cl, most preferably F.

Pseudohalogen groups are preferably understood to mean CN, SCN and OCN, more preferably CN.

The aforementioned groups with donor or acceptor action do not rule out the possibility that further radicals and substituents which are specified in the present application but are not included in the above list of groups with donor or acceptor action have donor or acceptor action.

The aryl radicals or groups, heteroaryl radicals or groups, alkyl radicals or groups, cycloalkyl radicals or groups, heterocycloalkyl radicals or groups, alkenyl radicals or groups and groups with donor and/or acceptor action may—as mentioned above—be substituted or unsubstituted. In the context of the present application, an unsubstituted group is understood to mean a group in which the substitutable atoms of the group bear hydrogen atoms. In the context of the present application, a substituted group is understood to mean a group in which one or more substitutable atom(s) bear(s) a substituent instead of a hydrogen atom at least at one position. Suitable substituents are the substituents already mentioned above with regard to the aryl radicals or groups.

When radicals with the same numbering occur more than once in the compounds of the present invention, these radicals may each independently have the definitions specified.

In the compound of the general formula (I), X is S or O, preferably O.

The $R^1$ radical in the compound of the general formula (I) is independently aryl, heteroaryl, alkyl, cycloalkyl, heterocycloalkyl, a crosslinkable or polymerizable group bonded via a spacer, —N$R^3R^4$, —P(O)$R^5R^6$, —P$R^7R^8$, —S(O)$_2R^9$, —S(O)$R^{10}$, —S$R^{11}$ or —O$R^{12}$, or a C group, preferably aryl, heteroaryl or —N$R^3R^4$ or a C group, where the aforementioned radicals may be unsubstituted or substituted. Suitable substituents have been specified above. The C group is defined hereinafter. More preferably, $R^1$ is phenyl, C group, or —N$R^3R^4$ which may be substituted by the aforementioned substituents or unsubstituted. Most preferably, $R^1$ is C group, or —N$R^3R^4$ which may be substituted by the aforementioned substituents or unsubstituted.

In a further preferred embodiment the radical $R^1$ is independently aryl selected from phenyl, naphthyl, anthracenyl, phenanthrenyl, indenyl and fluorenyl which each may be unsubstituted substituted at one, more than one or all substitutable positions, heteroaryl selected from pyridine radicals, pyrimidine radicals, pyrrole radicals, furan radicals, pyrazole radicals, imidazole radicals, thiophene radicals, oxazole radicals, thiazole radicals, triazole radicals, benzofuryl radicals, benzothienyl radicals, benzopyrrolyl radicals, dibenzofuryl radicals, phenanthrolinyl radicals, carbazolyl radicals, azacarbazolyl radicals and diazacarbazoyl radicals which may be unsubstituted or substituted at one, more than one or all substitutable positions, alkyl, cycloalkyl, heterocycloalkyl, a crosslinkable or polymerizable group bonded via a spacer, —N$R^3R^4$, —P(O)$R^5R^6$, —P$R^7R^8$, —S(O)$_2R^9$, —S(O)$R^{10}$, —S$R^{11}$ or —O$R^{12}$, where the aforementioned radicals may be unsubstituted or substituted. Suitable substituents have been specified above.

In a further even more preferred embodiment the radical $R^1$ is —N$R^3R^4$; and $R^3$, $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, more preferred definitions of the radicals $R^3$ and $R^4$ are mentioned below. Also, preferred groups —N$R^3R^4$ are mentioned below.

The $R^2$ radical in the compound of the general formula (I) is independently aryl, heteroaryl, alkyl, cycloalkyl, heterocycloalkyl, a crosslinkable or polymerizable group bonded via a spacer, —NR³R⁴, —P(O)R⁵R⁶, —PR⁷R⁸, —S(O)₂R⁹, —S(O)R¹⁰, —SR¹¹ or —OR¹², more preferably aryl, heteroaryl or —NR³R⁴, where the aforementioned radicals may be unsubstituted or substituted. Suitable substituents have been specified above. Most preferably, R¹ is heteroaryl or —NR³R⁴ which may be substituted by the aforementioned groups or unsubstituted.

In the compound of the general formula (I), if present, R³ and R⁴ are each independently aryl, heteroaryl, alkyl, cycloalkyl or heterocycloalkyl, a crosslinkable or polymerizable group bonded via a spacer, or R³ and R⁴ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action.

More preferably, R³ and R⁴ are each independently aryl, or R³ and R⁴ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action.

Most preferably, in the compound of the general formula (I), the R³ and R⁴ radicals form, together with the nitrogen atom, a cyclic radical which has 5 ring atoms and may be fused to one or more, preferably two, further cyclic radicals having 3 to 10, more preferably 5 or 6, ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and are preferably unsubstituted.

Examples of preferentially suitable —NR³R⁴ are selected from carbazolyl, pyrrolyl, indolyl, imidazolyl, triazolyl, benzimidazolyl, azacarbazolyl, diazacarbazolyl and diphenylamine, where the aforementioned groups are unsubstituted or substituted by one or more substituents selected from alkyl, cycloalkyl, heterocycloalkyl, aryl, heteroaryl, a crosslinkable or polymerizable group bonded via a spacer or a group with donor or acceptor action.

The R¹ radical may also preferably be —NR³R⁴ where —NR³R⁴ is a five-membered heterocyclic radical of the general formula (II). The definition of the radical of the general formula (II) can be found below. For R¹, particularly preferred radicals are therefore also:

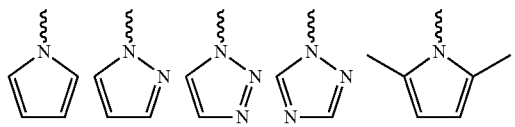

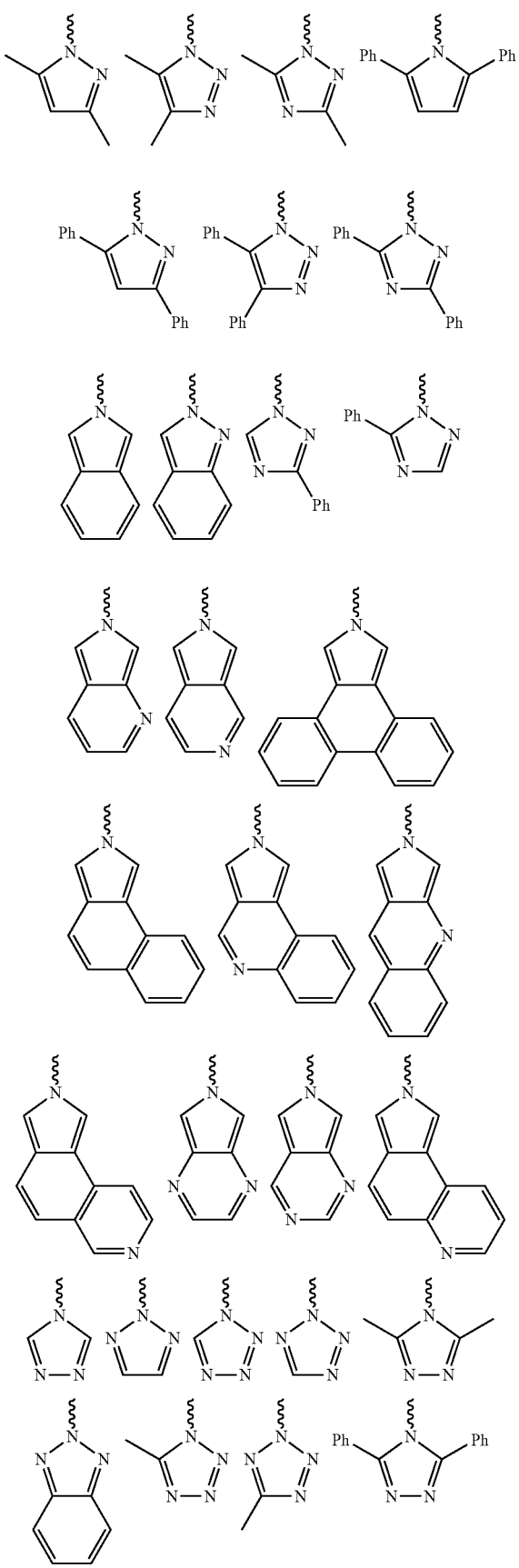

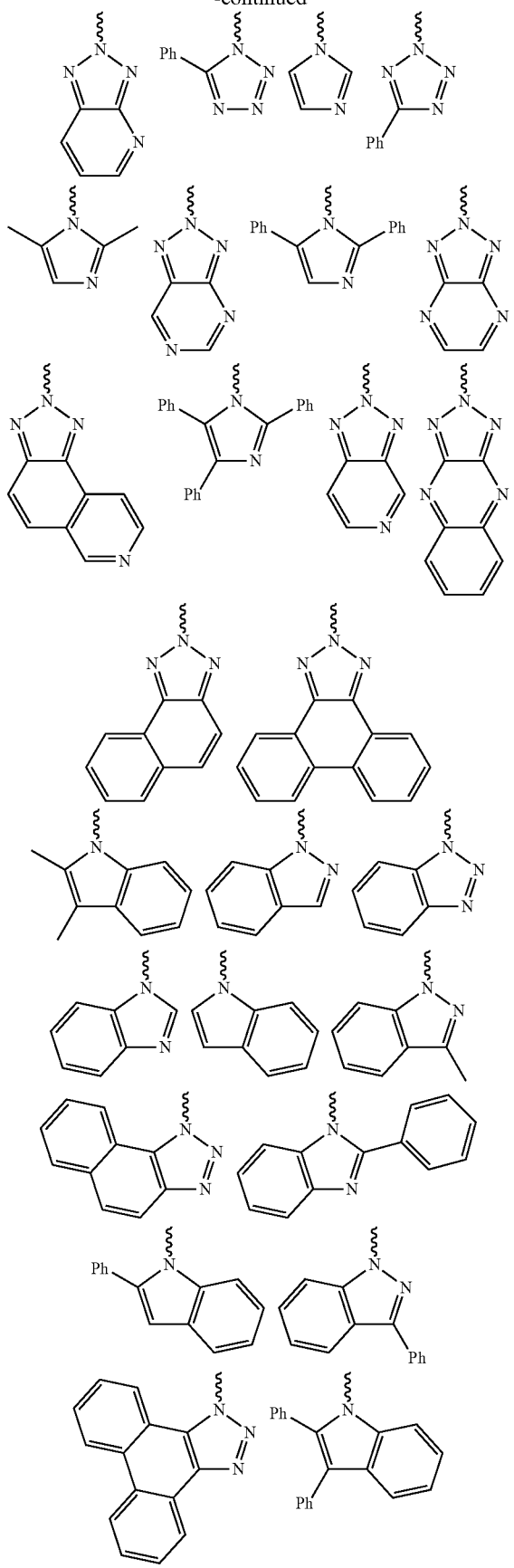
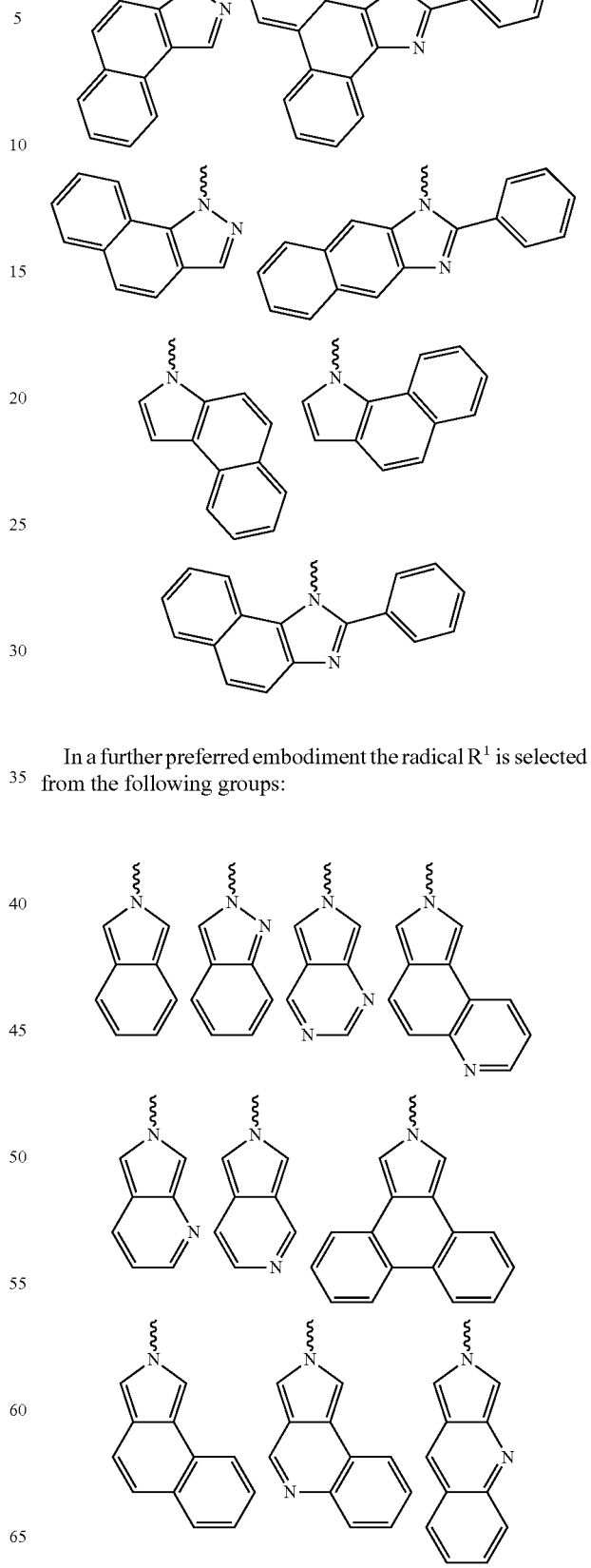
In a further preferred embodiment the radical R¹ is selected from the following groups:
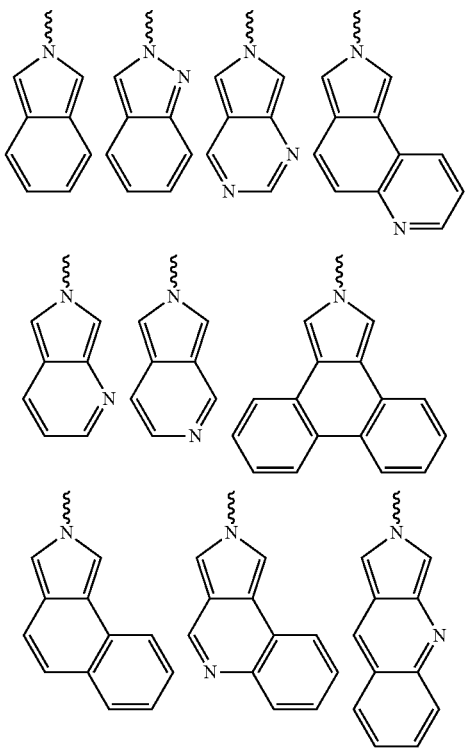

-continued

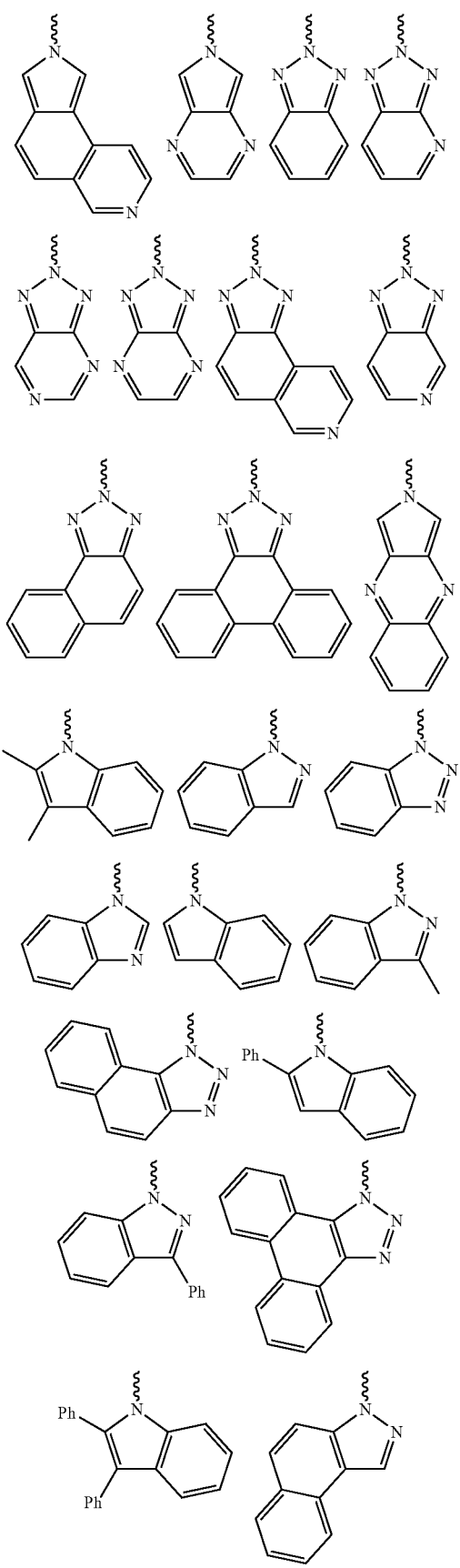

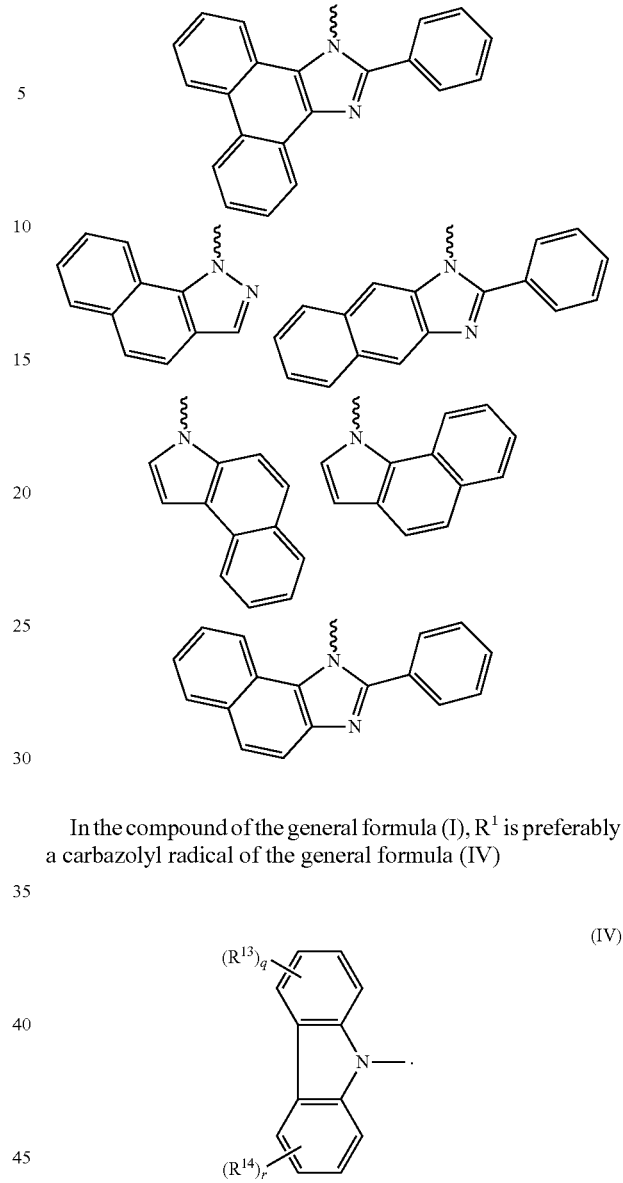

In the compound of the general formula (I), $R^1$ is preferably a carbazolyl radical of the general formula (IV)

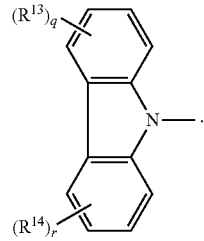

(IV)

The above-described substituents which may be present on the fused rings of the —$NR^3R^4$— moiety are symbolized in the formula by $(R^{13})_q$ and $(R^{14})_r$, and are defined hereinafter.

In the radical of the general formula (IV), $R^{13}$, $R^{14}$ are each independently aryl, heteroaryl, alkyl, cycloalkyl, heterocycloalkyl, a crosslinkable or polymerizable group bonded via a spacer, —$NR^3R^4$, —$P(O)R^5R^6$, —$PR^7R^8$, —$S(O)_2R^9$, —$S(O)R^{10}$, —$SR^{11}$ or —$OR^{12}$, group with donor acceptor action.

In the compound of the general formula (I), $R^5$, $R^6$, $R^7$, $R^8$, $R^9$, $R^{10}$, $R^{11}$, $R^{12}$ are each independently aryl, heteroaryl, alkyl, cycloalkyl or heterocycloalkyl, a crosslinkable or polymerizable group bonded via a spacer, preferably aryl or heteroaryl, where the radicals are unsubstituted or substituted by one or more of the radicals selected from alkyl, cycloalkyl, heterocycloalkyl, aryl, heteroaryl and a group with donor or acceptor action, more preferably unsubstituted or substituted phenyl, where suitable substituents are specified above, for example tolyl or a group of the formula

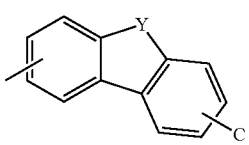

in which Y is S or O, and the C group is as defined above.

Most preferably, $R^8, R^9, R^{10}, R^{11}, R^{12}, R^{13}, R^{14}$ and $R^{15}$ are each independently phenyl, tolyl or a group of the formula

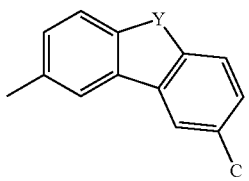

in which Y is S or O, and the C group is as defined above.

Particularly preferred examples of radicals of the general formula (IV), i.e. particularly preferred —$NR^3R^4$ groups, are:

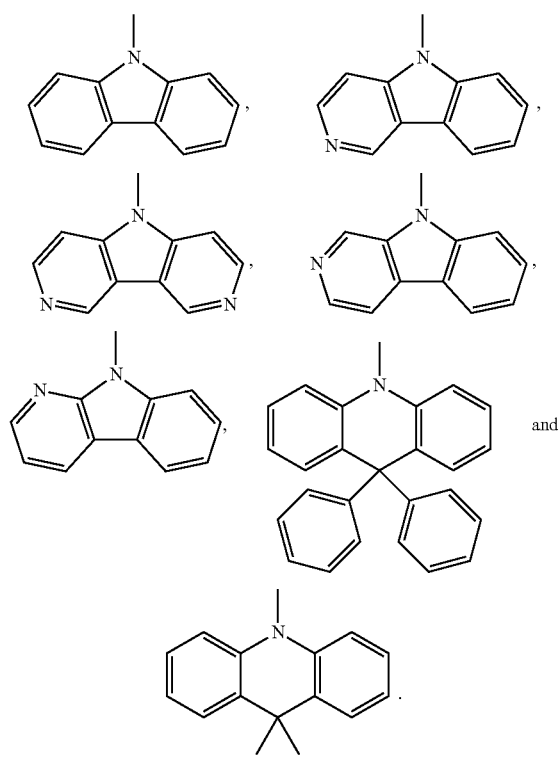

Particularly preferred —$P(O)R^5R^6$ groups are:

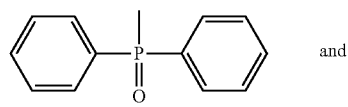 and

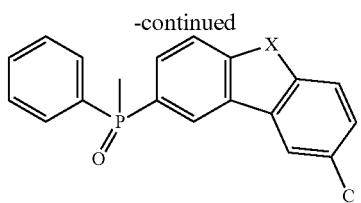

in which X and the C group are each as defined above.

A particularly preferred $PR^7R^8$ group is:

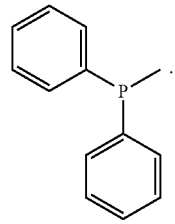

Particularly preferred —$S(O)_2R^9$ and —$S(O)R^{10}$ groups are:

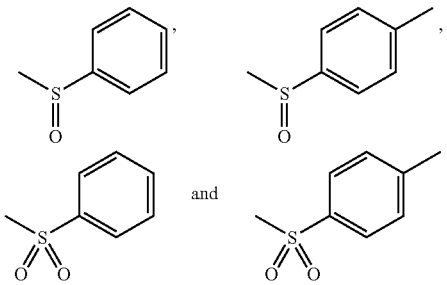

Particularly preferred —$SR^{11}$ and —$OR^{12}$ groups are:

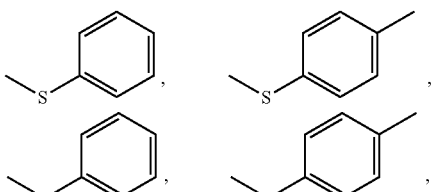

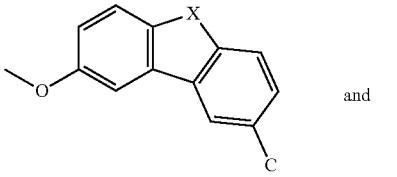

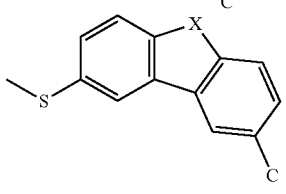

in each of which X is S or O, and C is as defined above.

Polymerizable or crosslinkable groups suitable in accordance with the invention are specified hereinafter. The person skilled in the art is aware that, in the inventive use, compounds of the general formula (I) used in polymeric or crosslinked form have at least one crosslinkable or polymerizable group and have been crosslinked or polymerized. Compounds of the general formula (I) which do not have any polymerizable or crosslinkable groups, or compounds of the general formula (I) which have polymerizable or crosslinkable groups, can be used in monomeric form in accordance with the invention. The same applies to compounds of the general formula (III).

In the compounds of the general formula (I), n is 0, 1, 2, 3 or 4, preferably 0, 1 or 2, more preferably 1, which means that, more preferably, one $R^1$ group with the abovementioned definitions is present in the compound of the general formula (I).

In the compounds of the general formula (I), m is 0, 1, 2 or 3, preferably 0 or 1, more preferably O, which means that, more preferably, no $R^2$ group with the abovementioned definitions is present in the compound of the general formula (I).

In the compounds of the general formula (I), p is 1 or 2, preferably 1, which means that, more preferably, one C group with the abovementioned definitions is present in the compound of the general formula (I).

In the compounds of the general formula (I), m+p is ≤4, which means that, in the compound of the general formula (I), not more than 4 substituents altogether are present on the appropriate benzene radical of the dibenzofuran or dibenzothiophene base skeleton to which the C group and $R^2$ are bonded.

It is readily apparent to the person skilled in the art that hydrogen atoms are present in the case that no substituents are present at positions in the compounds of the general formula (I).

In the inventive compounds of the general formula (I), at least one five-membered saturated or unsaturated heterocyclic C radical of the general formula (II)

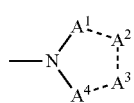

(II)

is present, with the abovementioned definitions of $A^1$, $A^2$, $A^3$, $A^4$, $R^a$, $R^b$, $R^c$, $R^d$, $R^e$, $R^f$, $R^g$ and $R^h$.

According to the invention, the radical (II) may be saturated or unsaturated. In the case of a saturated C radical, all bonds which occur in the five-membered ring between two nitrogens $NR^b$, $NR^d$, $NR^f$ and $NR^h$ are single bonds.

In the case of an unsaturated C radical, general formula (II), the bonds which occur in the five-membered ring between N, $A^1$, $A^2$, $A^4$ and/or $A^4$ may be corresponding single or double bonds. C radicals which comprise at least one double bond may therefore be unsaturated or have aromatic character. The person skilled in the art is aware that the general formula (II) describes all radicals possible in accordance with the invention, i.e. saturated, unsaturatated and aromatic radicals, even though only dotted single bonds are shown in the drawing. The person skilled in the art knows which bonds in the general formula (II) are single or double bonds and that, in the case of saturated or partly saturated radicals of the general formula (II), further hydrogen atoms are optionally present on the corresponding $A^1$, $A^2$, $A^3$ and $A^4$. In partly unsaturated or aromatic C radicals, the $R^a$, $R^b$, $R^c$, $R^d$, $R^e$, $R^f$, $R^g$ radicals are not present at the corresponding sites on $A^1$, $A^2$, $A^3$ and/or $A^4$. The formulation, for example, "$R^a$ or $R^b$" is selected since, in the inventive compounds, for example, either $R^a$ or $R^b$ etc. is present according to which definitions $A^1$, $A^2$ etc.

$R^a$, $R^b$, $R^c$, $R^d$, $R^e$, $R^f$, $R^g$ and $R^h$ are each independently hydrogen, aryl, heteroaryl, alkyl, cycloalkyl, heterocycloalkyl, a crosslinkable or polymerizable group bonded via a spacer. With regard to the definition of the radicals mentioned and preferred embodiments, the above statements apply. Most preferably, $R^a$, $R^b$, $R^c$, $R^d$, $R^e$, $R^f$, $R^g$ and $R^h$ are each independently hydrogen, alkyl or aryl. $R^a$, $R^c$, $R^e$ and $R^g$ are especially preferably each independently hydrogen, alkyl or aryl. $R^b$, $R^d$, $R^f$ and $R^h$ are especially preferably each independently alkyl or aryl, which means that preferably no NH is present in the ring.

In a preferred embodiment of the present invention, $A^1$ is $CR^a$ or N, $A^2$ is $CR^c$ or N, $A^3$ is $CR^e$ or N and $A^4$ is $CR^g$ or N, which means that, in this preferred embodiment, no $R^b$, $R^d$, $R^f$ and $R^h$ radicals are present.

The general formula (II) preferably corresponds to the following formula (IIa)

(IIa)

or an isomeric formula thereof with the corresponding abovementioned definitions of $A^1$, $A^2$, $A^3$ and $A^4$; more particularly, in the formula (IIa), $A^1$ is $CR^a$ or N, $A^2$ is $CR^c$ or N, $A^3$ is $CR^e$ or N and $A^4$ is $CR^g$ or N.

In a preferred embodiment, the present invention relates to the inventive use wherein the C group in the compound of the general formula (I) is:

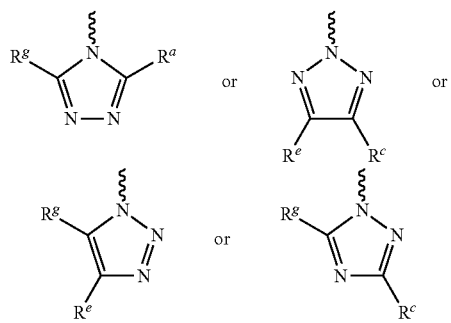

In one embodiment, $R^a$ in the radical mentioned above is not

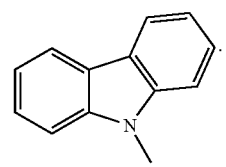

In a further preferred embodiment, the present invention relates to the inventive use wherein the C group in the compound of the general formula (I) is:

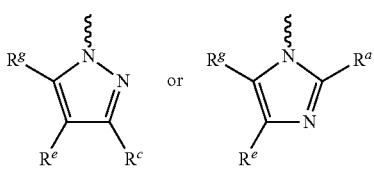

In one embodiment, the residues in the formula

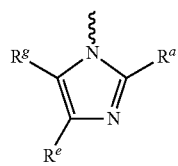

have the following meanings:
$R^g$, $R^e$ are H, and
$R^a$ is hydrogen, aryl, heteroaryl, alkyl, cycloalkyl, heterocycloalkyl, a crosslinkable or polymerizable group bonded via a spacer.

In a further preferred embodiment, the present invention relates to the inventive use

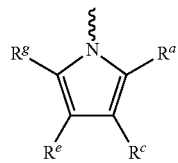

wherein the C group in the compound of the general formula (I) is:

In one embodiment, the use of the following compound is excluded:

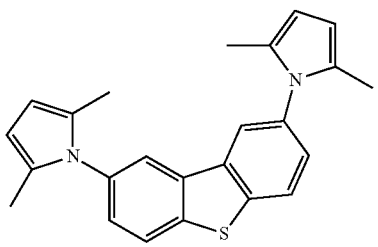 [SMILES: Cc1ccc(C)n1-c1ccc2sc3ccc(-n4c(C)ccc4C)cc3c2c1]

In a further preferred embodiment, the present invention relates to the inventive use wherein at least one of $R^a$, $R^c$, $R^e$ and $R^g$ in the compound of the general formula (I) is aryl, preferably optionally substituted phenyl.

In a preferred embodiment of the present invention,
$R^a$ and $R^c$ or
$R^e$ and $R^g$, and/or, preferably or,
$R^c$ and $R^e$
form, together with the carbon atom, a cyclic radical which has 3 to 10 ring atoms and may be unsubstituted or substituted by one or more substituents selected from alkyl, cycloalkyl, heterocycloalkyl, aryl, heteroaryl or a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action.

In a particularly preferred embodiment,
$R^a$ and $R^c$ or
$R^e$ and $R^g$, and/or, preferably or,
$R^c$ and $R^e$
form, together with the carbon atom, a cyclic radical which has 5, 6 or 7 ring atoms and is either unsubstituted or substituted by alkyl groups, for example methyl, and/or aryl groups, for example phenyl.

In this embodiment, in which the $R^a$ and $R^c$ or $R^e$ and $R^g$, and/or, preferably or, $R^c$ and $R^e$ radicals form the abovementioned fused rings, the remaining, i.e. unfused, $R^a$, $R^c$, $R^e$, $R^g$ radicals are preferably aryl, more preferably phenyl or substituted phenyl.

By virtue of the fact that ($R^a$ and $R^c$) or ($R^e$ and $R^g$) or ($R^c$ and $R^e$) preferably form a corresponding abovementioned fused ring, with particular preference in accordance with the invention, only one fused ring is present in the C radical of the general formula (II).

Very particularly preferred C radicals are depicted below:

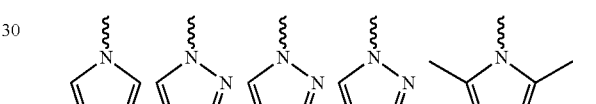

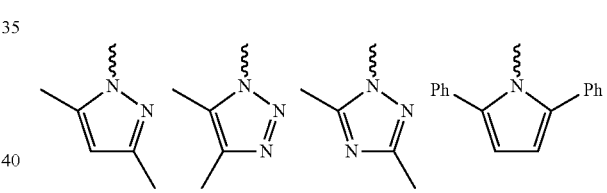

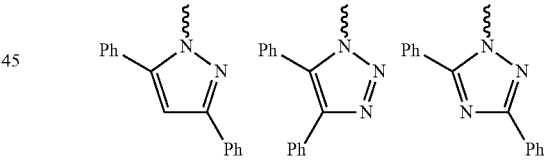

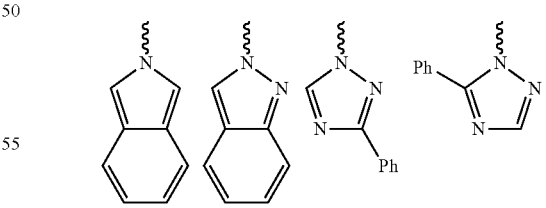

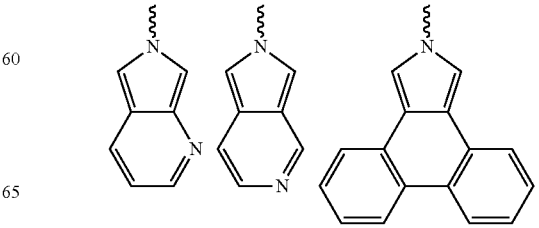

-continued
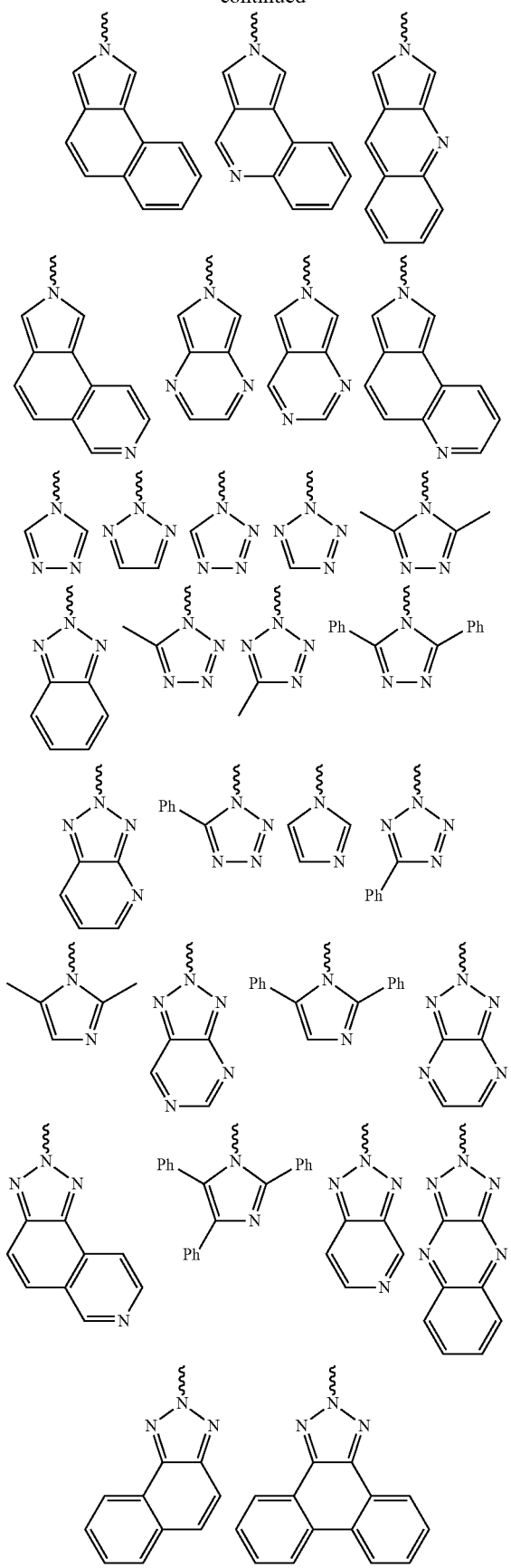
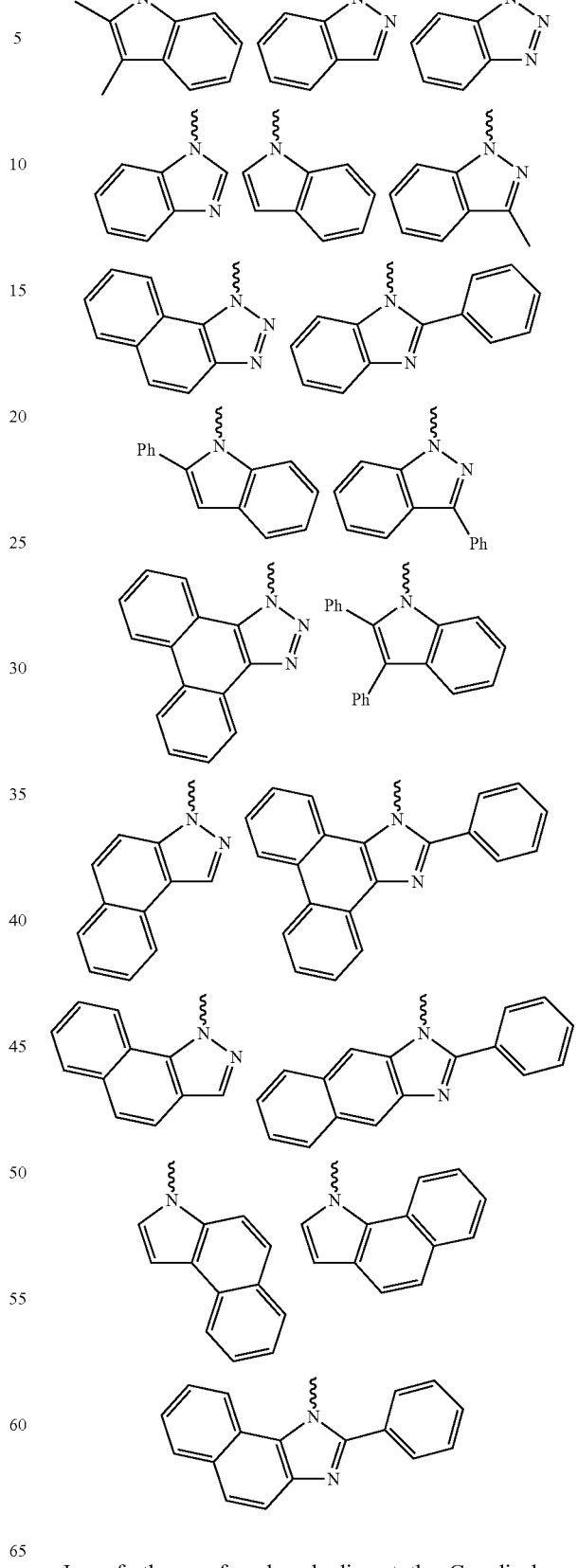
In a further preferred embodiment the C radicals are selected from:

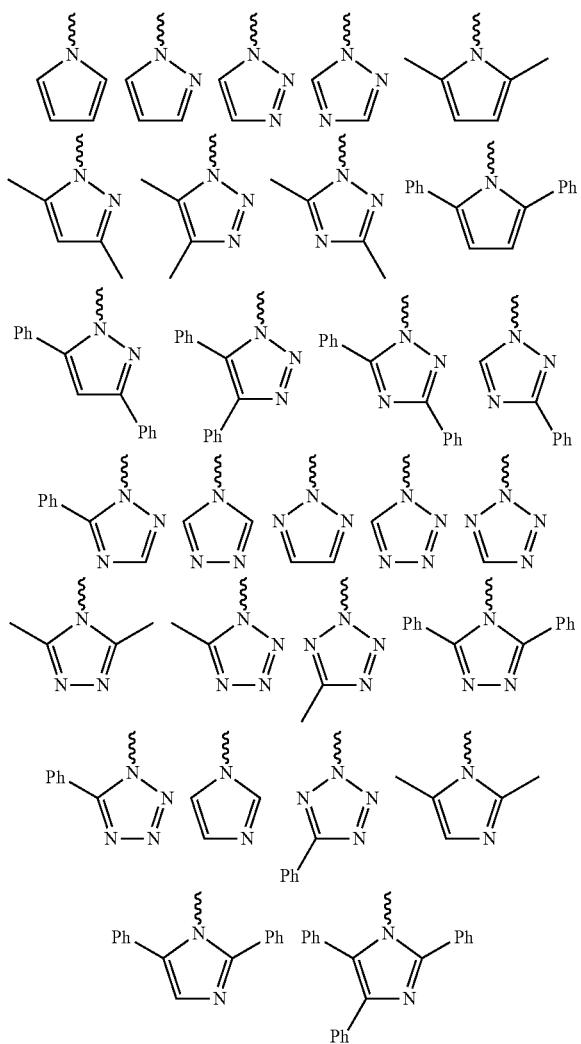

In a further preferred embodiment the present invention concerns the use of a compound of formula (I) as defined above, in which $R^1$ is —$NR^3R^4$, $R^3$, $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, C is a five-membered saturated or unsaturated heterocyclic radical of the general formula (II)

(II)

where $A^1$ are each independently $CR^a$, N or $NR^b$;

$A^2$ are each independently $CR^c$, N or $NR^d$;

$A^3$ are each independently $CR^e$, N or $NR^f$;

$A^4$ are each independently $CR^g$, N or $NR^h$ $R^a$, $R^b$, $R^c$, $R^d$, $R^e$, $R^f$, $R^g$, $R^h$ are each independently hydrogen, aryl, heteroaryl, alkyl, cycloalkyl, heterocycloalkyl, a crosslinkable or polymerizable group bonded via a spacer, n is 1, and m is 0 or 1, preferably 0, wherein the residues in formula (I) not defined before are defined as mentioned above.

In a further embodiment of the present invention, two units of the general formula (I) are bridged to one another via a bond, i.e. a C—C bond, a C—N bond, a linear or branched, saturated or unsaturated bridge optionally interrupted by at least one heteroatom or via O, where this bridge in the general formula (I) where this bridge in the general formula (I) is bonded in place of $R^a$, $R^b$, $R^c$, $R^d$, $R^e$, $R^f$, $R^g$, $R^h$ or via and/or in place of $R^1$ or $R^2$.

The bridge is preferably selected from the group consisting of a bond, —$CH_2$—, —$C_2H_4$—, —$C_3H_6$—, —$C_4H_8$—, —$C_6H_{12}$—, —$C_8H_{16}$—, —$C_9H_{18}$—, —$CH(C_8H_{17})CH_2$—, —$C_2H_4(CF_2)_8C_2H_4$—, —C≡C—, -1,4-$(CH_2)_2$-phenyl-$(CH_2)_2$—, 1,3-$(CH_2)_2$-phenyl-$(CH_2)_2$—, -1,4-phenyl-, -1,3-phenyl-, —O—, —O—$Si(CH_3)_2$—O— or —O—$Si(CH_3)_2$—O—$Si(CH_3)_2$—O—. The bridge is most preferably a bond or -1,3-phenyl-.

The inventive bridged compounds most preferably correspond to the following general formula (Ia) or (Ib)

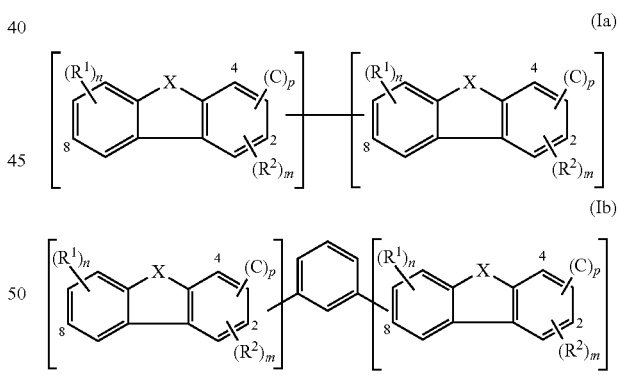

with the abovementioned definitions of $R^1$, $R^2$, X, C, m, n and p. Preferably, in this embodiment, n and m are each 0, and p is 1.

According to the invention, in the compound of the general formula (I) used, the at least one C radical is bonded in the 2 and/or 4 position, preferably in the 2 position.

The $R^1$ and $R^2$ radicals, if present, may generally be bonded at all possible positions not occupied by the C radical(s), for example positions 1, optionally 2, 3, optionally 4, 6, 7, 8 and/or 9. The positions of the dibenzofurans or dibenzothiophenes used in accordance with the invention are shown in the diagram below:

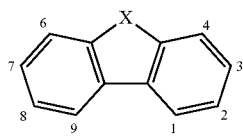

where X is O or S.

In a preferred embodiment, in the case that n and p in the compound of the general formula (I) are 1, the radical $R^1$ is preferably bonded in 8 position and the radical C is preferably bonded in 2 position. More preferably, m is 0.

In a very particularly preferred embodiment, the compound of the general formula (I) for the inventive use is selected from the following group:

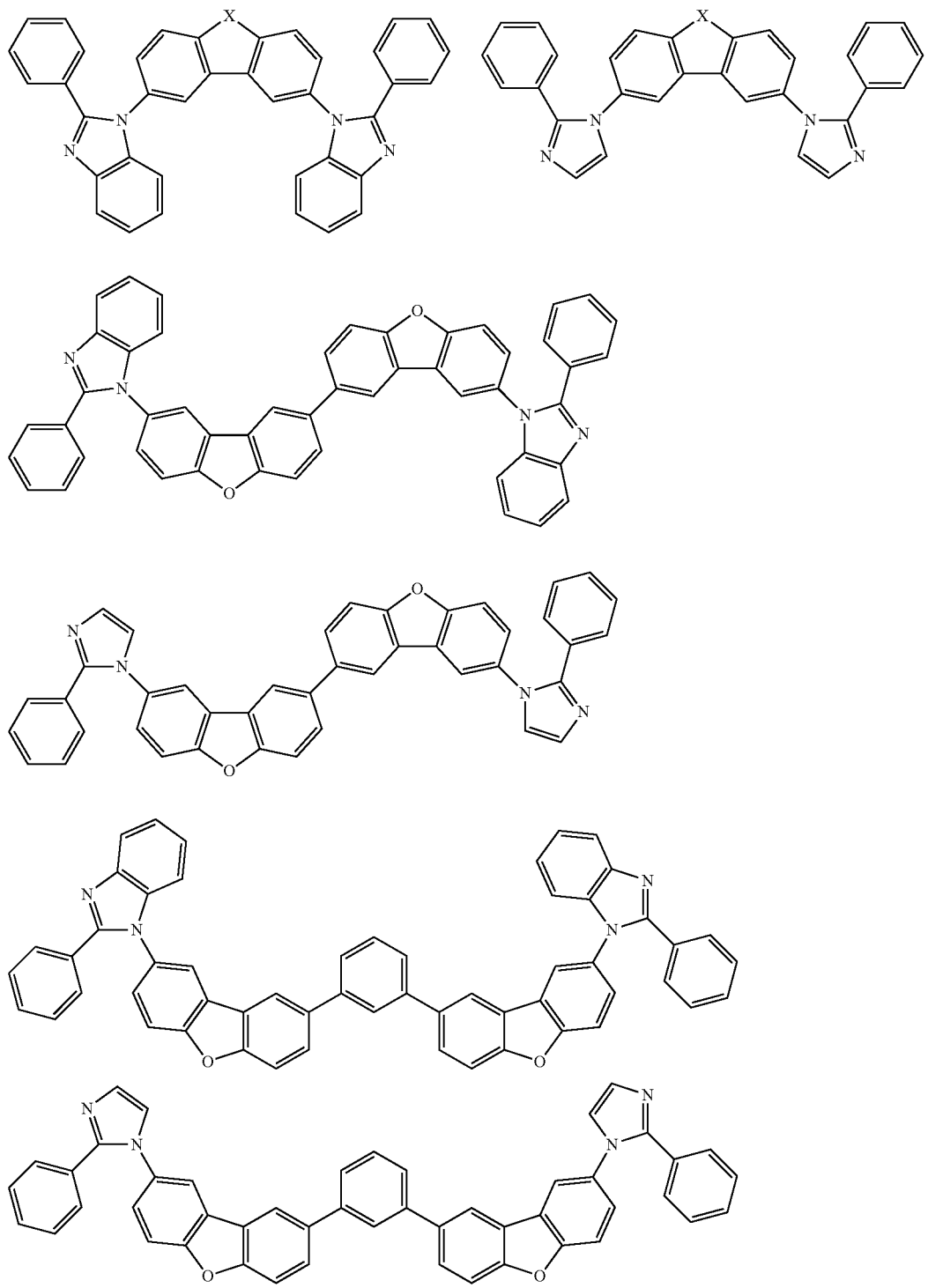

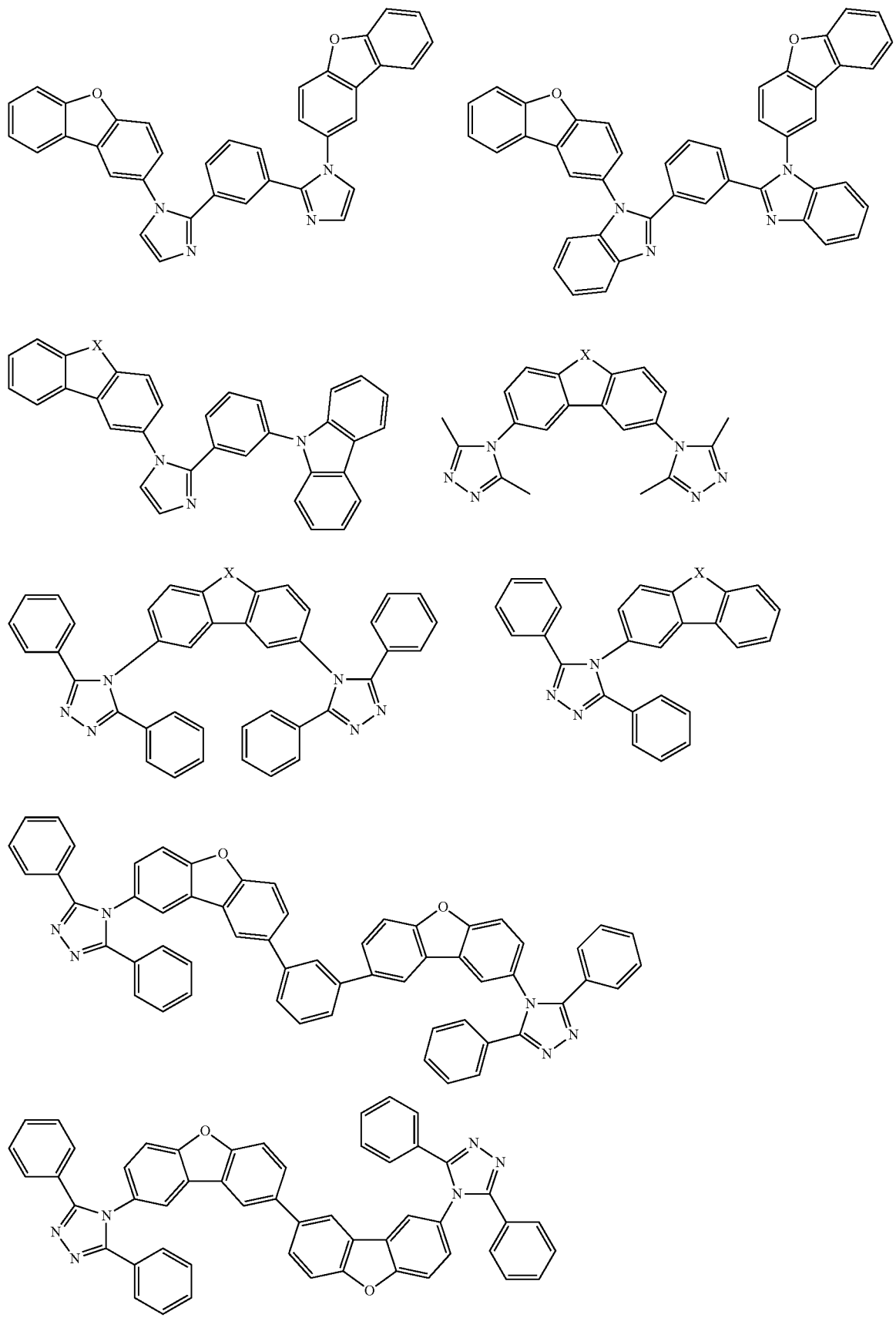

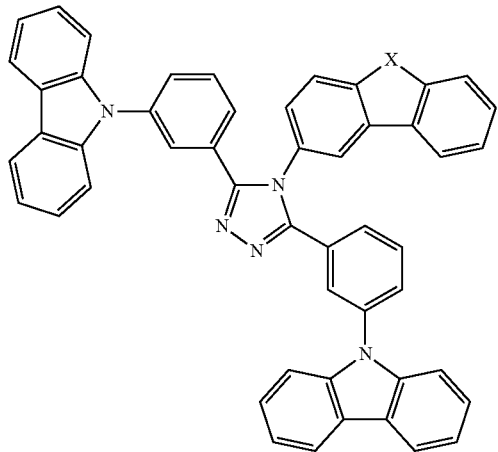
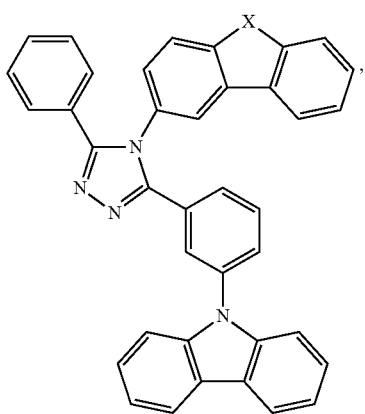
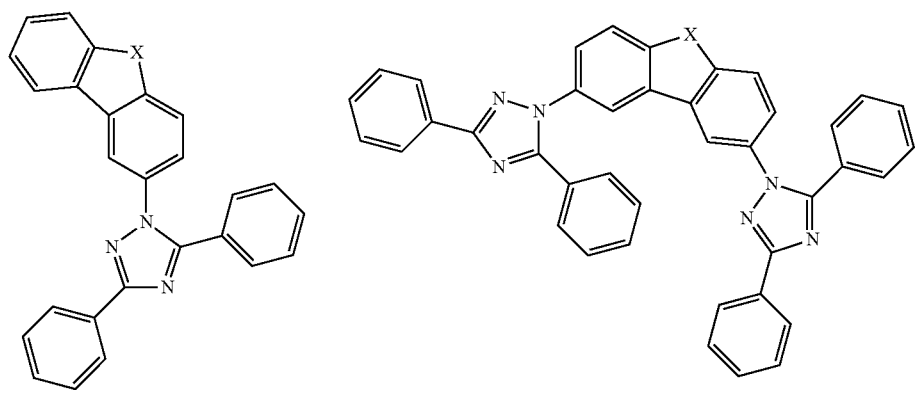
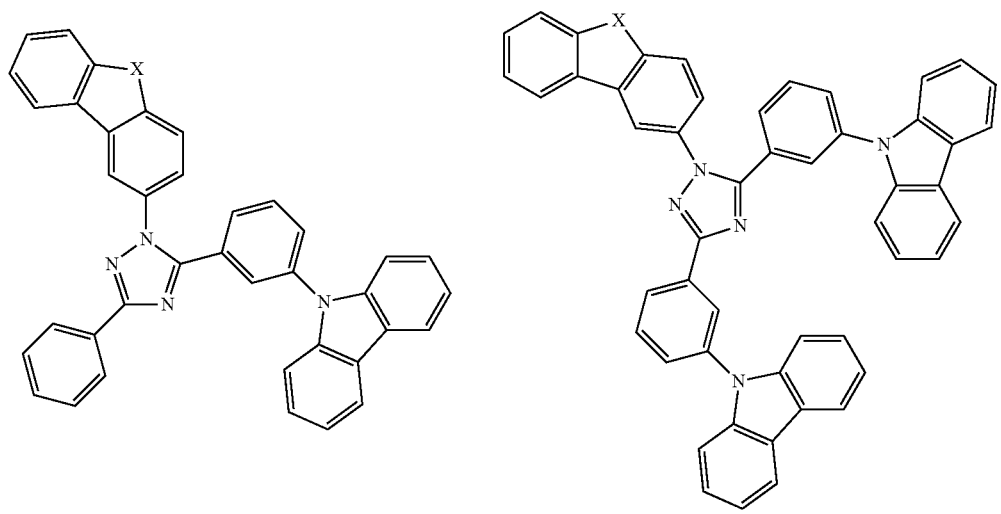

-continued
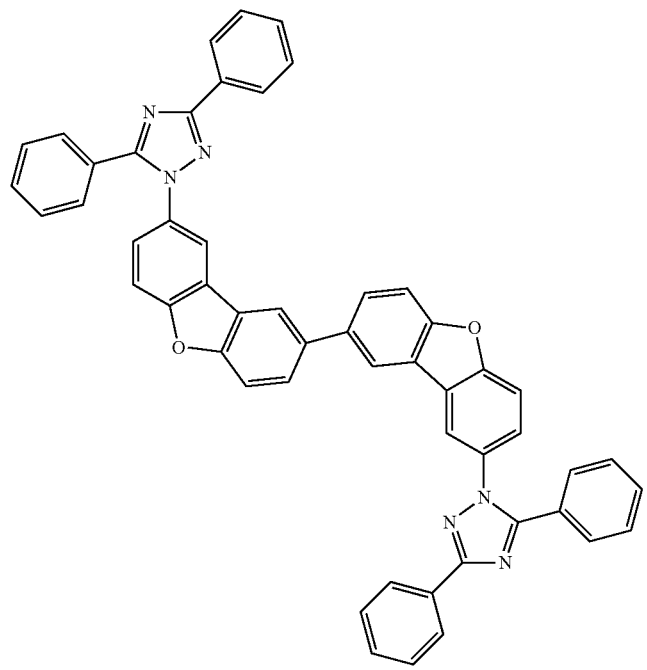
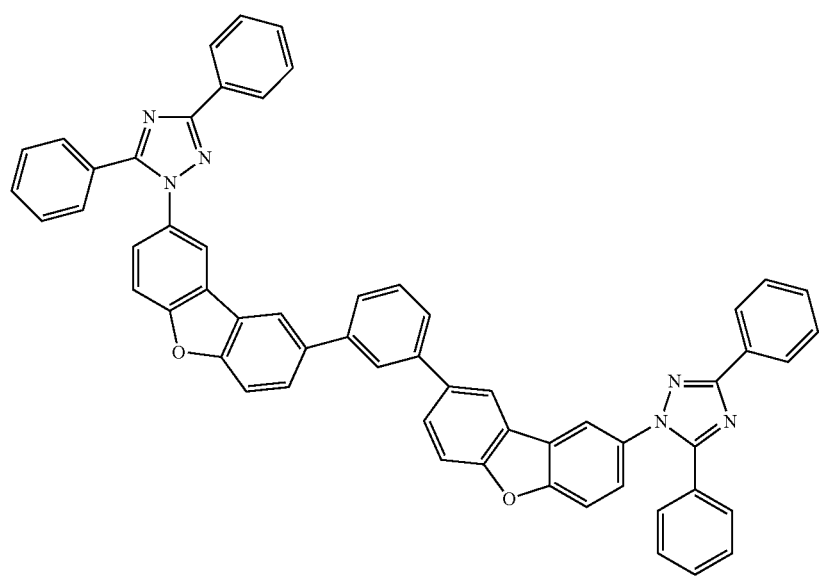
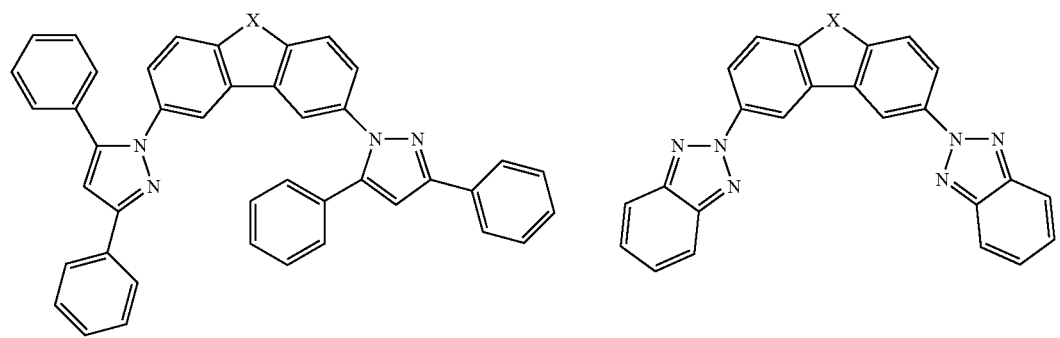

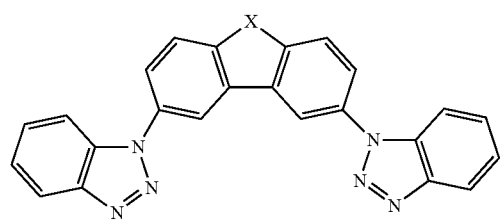 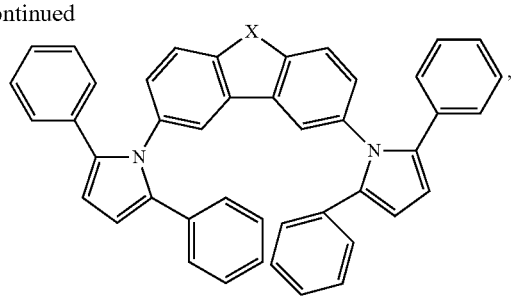

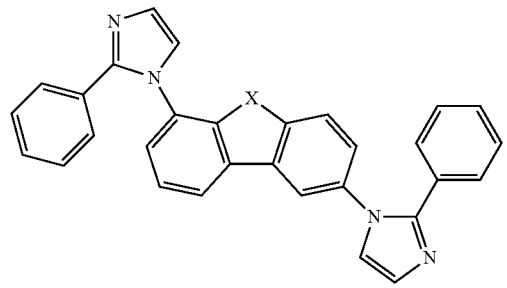 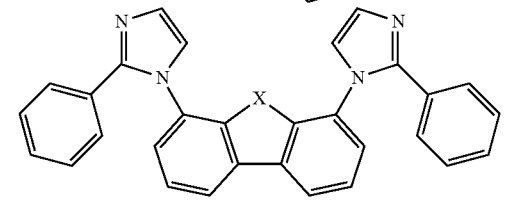

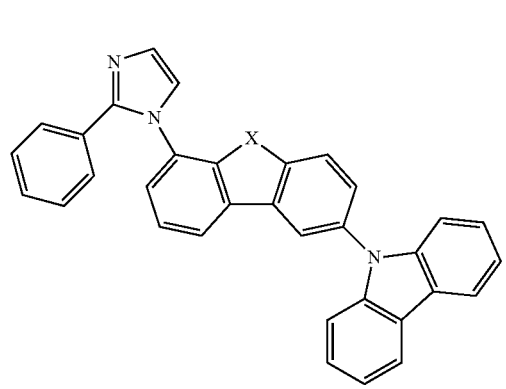 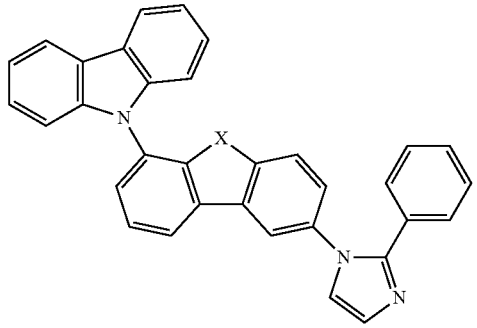

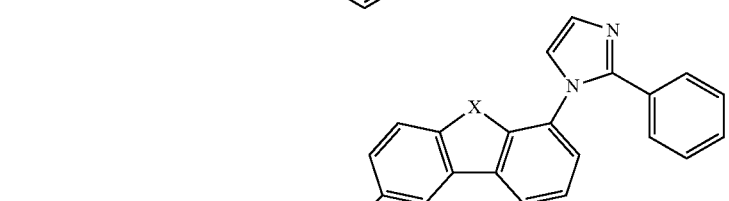

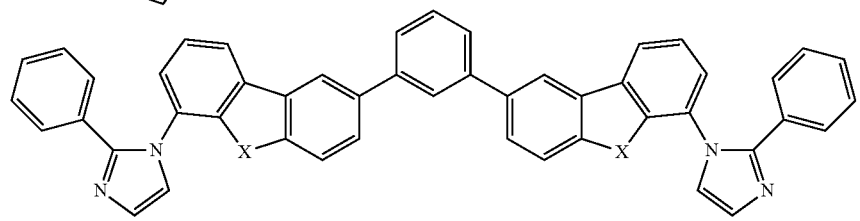

where X is S or O.

Processes for preparing the inventive compounds of the general formula (I) are known per se to those skilled in the art and are described by way of example for the compounds of the general formula (III).

According to the invention, a crosslinkable or polymerizable group bonded via a spacer is generally a group of the formula $-(Sp)_{x1}-[PG']_x$
where
Sp is a bridging unit, PG' is a crosslinkable or polymerizable group,
x1 is 0 or 1, and
x is an integer from 1 to 4.

Since x1 may be defined as 0, it is also possible in accordance with the invention that the crosslinkable or polymerizable group is not bonded via a spacer, but directly.

Sp is, for example, selected from the group consisting of —Ar—, —ArY—, —YAr—, —YAr(CR$^{26}$R$^{27}$)$_n$—, —(CR$^{26}$R$^{27}$)$_n$—, —(YCR$^{26}$R$^{27}$)$_n$—, or —(CR$^{26}$R$^{27}$Y)$_n$—, where
Y is NR$^5$, O, S, C═O, C(═O)O, where R$^5$ is H; C$_6$-C$_{18}$-aryl optionally substituted by at least one C$_1$-C$_{18}$-alkyl or C$_1$-C$_{18}$-alkoxy, C$_1$-C$_{18}$-alkyl optionally interrupted by —O—;
R$^{26}$ and R$^{27}$ are each independently hydrogen, fluorine or C$_1$-C$_{20}$-alkyl,
n is an integer from 1 to 20,
Ar is alkyl, cycloalkyl, aryl or heteroaryl, which may optionally be substituted.

The crosslinkable or polymerizable group PG' is preferably a group selected from —C(R$^{44}$)═CH$_2$, —NHC(O)—C(R$^{45}$)═CH$_2$, —OCH$_2$CH$_2$OC(O)—C(R$^{45}$)═CH$_2$, —OC(O)—C(R$^{45}$)═CH$_2$, —C(O)—C(R$^{46}$)═CH$_2$, —C≡C—, —N═C, —O—CH(CH$_2$CH$_2$CH═CH$_2$)$_2$; C$_5$-C$_8$-cycloalkenyl, bicycloalkenyl, optionally substituted or unsubstituted and having 5 to 30 carbon atoms, (1,2-epoxy ether), (oxetanyl), where
s is an integer from 1 to 6, m1 is an integer from 1 to 6, and R$^6$ is hydrogen or C$_1$-C$_{20}$-alkyl.
R$^{44}$ is hydrogen, C$_1$-C$_4$-alkyl or halogen,
R$^{45}$ is hydrogen, C$_1$-C$_4$-alkyl or halogen, and
R$^{46}$ is hydrogen, C$_1$-C$_4$-alkyl or C$_6$-C$_{12}$-aryl, or
PG' in a further embodiment is a group obtainable from a polymerizable group

R$^{48}$—AHG,
|
R$^{47}$ where AHG is an aromatic or heteroaromatic radical which may optionally be substituted, for example R$^{47}$ and R$^{48}$ are each independently halogen, —C≡CH, boric acid, boric ester, —Mg-Hal, —Zn-Hal, —Sn(R$^{52}$)$_3$, where Hal is halogen and R$^{52}$ is C$_1$-C$_{18}$-alkyl.
R$^{49}$ is independently hydrogen, C$_1$-C$_{18}$-alkyl optionally interrupted by —O—, C$_1$-C$_{18}$-perfluoroalkyl, C$_1$-C$_{18}$-alkoxy optionally interrupted by —O—, or C$_7$-C$_{25}$-aralkyl.

When PG' differs from the polymerizable group

R$^{48}$—AHG,
|
R$^{47}$ the polymers may comprise, in addition to the repeat units mentioned, one or more repeat units RG$^I$ and/or RG$^{II}$:
RG$^I$: units which improve the hole injection or hole transport properties of the polymer;
RG$^{II}$: units which improve the electron injection or electron transport properties of the polymer.

In the compounds of the general formula (I) or (III), polymerizable or crosslinkable groups may be present. In one embodiment, these may be polymerized or crosslinked. Processes for crosslinking or polymerization, for example free-radical processes, are known per se to those skilled in the art. It is possible in accordance with the invention to use free-radical initiators known to those skilled in the art, for example AIBN, or In a preferred embodiment of the present invention, the at least one polymerizable or crosslinkable group is selected from the group consisting of C═C double bond, acrylates, methacrylates, or 1,2-epoxy ethers.

When the compounds of the general formula (I) comprise, as the crosslinkable or polymerizable group, —CH═CH$_2$—, acrylates or methacrylates, the polymerization can be performed, for example, photochemically using known photoinitiators, described, for example, in "Chemistry & Technology of UV & EB Formulations for Coatings, Inks and Paints, Vol. 3: Photoinitiators for Free Radical and Cationic Polymerization" 1991, p. 1115-325). Known photoinitiators are added to the reaction mixture, for example, in an amount of 0.5 to 5% by weight, based on the total amount of all monomers present.

Further suitable polymerization processes are epoxy polymerization, various metathesis reactions, for example described in Ivin, K. J. and Mol, J. C., Olefin Metathesis and Metathesis Polymerization (Academic Press 1997), for example ring-opening metathesis, ADMET (acyclic diene-olefin metathesis), or hydrosilylation. The schemes shown below for formula (I) apply correspondingly to (III).

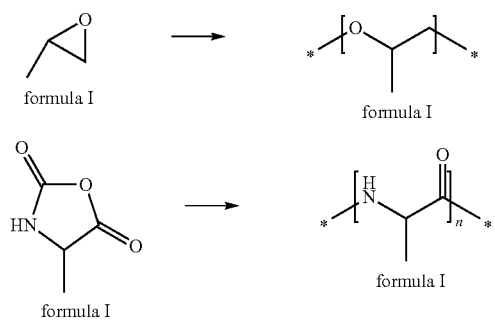

A hydrosilylation can be initiated, for example, by UV radiation, and can by catalyzed by free radical formers, transition metal complexes or Lewis bases, for example $H_2PtCl_6$, $R^hCl(PPh_3)_3$ or trans-IrCl(CO)(PPh_3)_2$.

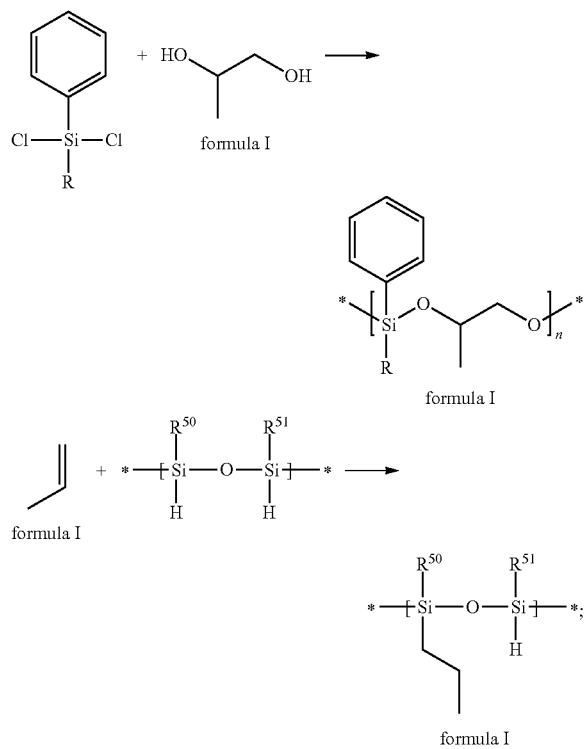

where $R^{50}$ and $R^{51}$ are each independently $C_1$-$C_8$-alkyl, $C_6$-$C_{24}$-aryl or $C_7$-$C_{12}$-aralkyl.

If PG' is a polymerizable group according to

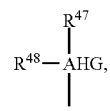

the compounds of the general formula (I) or (III) can be polymerized as follows.

Polymerization processes which use dihalogen-functionalized substrates can be performed under nickel-mediated coupling conditions, for example according to Colon et al. in J. Pol. Sci., Part A, Polymer Chemistry Edition 28 (1990) 367, and Colon et al. in J. Org. Chem. 51 (1986) 2627. The reaction is generally performed in a polar aprotic solvent, for example dimethylacetamide, with a catalytic amount of a nickel salt, triphenylphosphine and a large excess of zinc dust. A variant of the process is described in Ioyda et al. in Bull. Chem. Soc. Jpn, 63 (1990) 80, wherein an organosoluble iodide is used as an accelerator. A further nickel coupling reaction is described in Yamamoto, Progress in Polymer Science 17 (1992) 1153, wherein a mixture of a dihaloaromatic compound with an excess of nickel-(1,5-cyclooctadiene) complex is treated in an inert solvent. In all nickel coupling reactions, essentially random polymers are obtained when substrate mixtures of two or more aromatic dihalides are used.

Such polymerization reactions can be ended by adding a small amount of water. Alternatively, a monofunctional aryl halide can be used as a chain-terminating reagent.

Nickel coupling polymerizations afford essentially random polymers composed of units of the general formula (I) and/or (I*).

In addition, the compounds of the general formula (I) or (I*) can also be polymerized by Suzuki coupling, which is known to those skilled in the art. This polymerization reaction is described, for example, in N. Miyaua and A. Suzuki in Chemical Reviews, vol. 95, pp. 457-2483 (1995). For this purpose, preferably diiodides or dibromides of the compounds of the general formula (I) or (I*) are reacted with appropriate diboric acids or diboric esters. The reaction is preferably performed under Pd catalysis and in the presence of triphenylphosphine at 70° C. to 180° C. in an aromatic hydrocarbon solvent such as toluene. Dimethylformamide or tetrahydrofuran are also suitable. An aqueous base such as sodium carbonate or bicarbonate is used as the HBr scavenger. Corresponding processes are described, for example, in Leadbeater & Marco; Angew. Chem. Int. Ed. Eng. 42 (2003) 1407, T. I. Wallow and B. M. Novak in J. Org. Chem. 59 (1994) 5034-5037; and M. Remmers, M. Schulze, and G. Wegner in Macromol. Rapid Commun. 17 (1996) 239-252.

According to the invention, polymers which have formed from compounds of the general formula (I) and comprise one or more compounds of the general formula (I) can also be used in crosslinked or polymerized form. It is likewise possible that, in addition to the compounds of the general formula (I), further monomers are also polymerized, such that corresponding copolymers are formed. Corresponding examples are specified in WO 2007/090733.

The further monomers may also be hole-conducting units such as $RG^I$ and/or electron-conducting units such as $RG^{II}$, as described in WO 2007/090733.

These remarks relating to polymerization and crosslinking apply to the inventive compounds (I) and (III).

The present invention also relates to the use of crosslinked or polymeric materials comprising repeat units of the general formula (I) in crosslinked or polymerized form as host, blocker and/or charge transport materials.

The present invention also relates to the use of a compound of the general formula (I) as defined above or of a compound of the general formula (III) as defined hereinafter as components in polymerization and/or crosslinking reactions.

The present invention also relates to a crosslinked or polymerized material which comprises units of the general formula (III) as defined hereinafter.

Crosslinked or polymeric materials according to the present invention have excellent solubility in organic solvents, excellent film-forming properties and relatively high glass transition temperatures. In addition, high charge carrier mobilities, high stabilities of color emission and long operating times of the corresponding components can be observed when crosslinked or polymeric materials according to the present invention are used in organic light-emitting diodes (OLEDs).

The inventive crosslinked or polymerized materials are particularly suitable as coatings or in thin films, since they are thermally and mechanically stable and relatively defect-free.

Suitable processes for producing these thin films are, for example, vacuum deposition, spin-coating, the casting method, the Langmuir-Blodgett ("LB") method, the inkjet printing method, dip-coating, letterpress printing, screen printing, doctor blade printing, roller printing, reverse roller printing, offset lithography printing, flexographic printing, web printing, spray coating, brush coating or pad printing and the like. Among the methods mentioned, preference is given to vacuum deposition, spin-coating, the inkjet printing method and the casting method, since they are particularly simple and inexpensive to perform.

The individual component layers, especially the light emission layer, can be formed from a mixture of the inventive compounds and/or materials and optionally further compounds. The nonconjugated polymers of the present invention are particularly useful as matrix materials and/or electron conductors for phosphorescent compounds (triplet emitters) in organic light-emitting diodes (OLEDs).

In the case that layers are obtained by the spin-coating method, the casting method or the inkjet printing method, the coating can be obtained using a solution produced by dissolving the composition in a concentration of 0.0001 to 90% by weight in a suitable organic solvent such as benzene, toluene, xylene, tetrahydrofuran, methyltetrahydrofuran, N,N-dimethylformamide, acetone, acetonitrile, anisole, dichloromethane, dimethyl sulfoxide and mixtures thereof.

The inventive compounds of the formula (I) used in accordance with the invention, in monomeric, polymerized or crosslinked form, can be used as host, blocker and/or charge transport materials, preferably as electron transport materials, preferably in organic electronics applications selected from switching elements such as organic transistors, for example organic FETs and organic TFTs, organic solar cells and organic light-emitting diodes (OLEDs), preference being given to using the compounds of the formula (I) in OLEDs.

The present invention therefore preferably also relates to the inventive use of electron transport material.

The present application further provides for the inventive use of the compounds of the formula (I) in organic electronics applications, preferably in OLEDs.

The compounds of the formula (I) or an inventive crosslinked or polymerized material are notable in that they have at least one five-membered heterocyclic ring bonded via nitrogen on a dibenzofuran or dibenzothiophene base skeleton. These specific compounds are notable especially in that they ensure good efficiencies, good operative lifetimes and a high stability to thermal stress, and a low use and operating voltage of the organic electronics applications, especially of the OLEDs.

The compounds of the formula (I) or an inventive crosslinked or polymerized material can preferably be used as host material and/or hole/exciton blocker material and/or electron/exciton blocker material and/or electron conductor material in organic electronics applications, especially in OLEDs.

Owing to the transport properties and the position of the triplet level and hence the exciton blocker properties of the compounds of the formula (I) or of the inventive crosslinked or polymerized material, these compounds can also be used as hole/exciton blocker material and/or electron/exciton blocker material. Compounds of the formula (I) or an inventive crosslinked or polymerized material which have a good electron conductor capacity can especially be used on the cathode side of an OLED.

Suitable structures of the organic electronics applications are known to those skilled in the art and are specified in detail hereinafter with regard to the inventive compounds of the general formula (III).

The present invention also relates to a compound of the general formula (III)

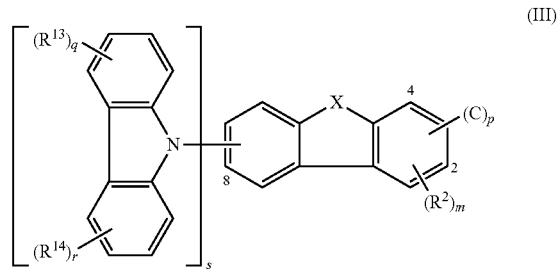

in which
X is S or O;
$R^2$ are each independently aryl, heteroaryl, alkyl, cycloalkyl, heterocycloalkyl, a crosslinkable or polymerizable group bonded via a spacer, $-NR^3R^4$, $-P(O)R^5R^6$, $-PR^7R^8$, $-S(O)_2R^9$, $-S(O)R^{10}$, $-SR^{11}$ or $-OR^{12}$,
$R^3$, $R^4$ are each independently aryl, heteroaryl, alkyl, cycloalkyl or heterocycloalkyl, a crosslinkable or polymerizable group bonded via a spacer,
  or $R^3$ and $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, and a group with donor or acceptor action;
$R^5$, $R^6$,
$R^7$, $R^8$,
$R^9$, $R^{10}$,
$R^{11}$, $R^{12}$ are each independently aryl, heteroaryl, alkyl, cycloalkyl or heterocycloalkyl, a crosslinkable or polymerizable group bonded via a spacer,
$R^{13}$, $R^{14}$ are each independently aryl, heteroaryl, alkyl, cycloalkyl, heterocycloalkyl, a crosslinkable or polymerizable group bonded via a spacer, —NR³R⁴, —P(O)R⁵R⁶, —PR⁷R⁶, —S(O)₂R⁹, —S(O)R¹⁰, —SR¹¹ or —OR¹², m is 0, 1, 2 or 3,
p is 1 or 2, where m+p is ≤4,
q is 0, 1, 2, 3 or 4,
r is 0, 1, 2, 3 or 4,
s is 1, 2, 3 or 4,
C is a five-membered saturated or unsaturated heterocyclic radical of the general formula (II)

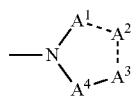

(II)

where
A¹ are each independently CR$^a$, N or NR$^b$;
A² are each independently CR$^c$, N or NR$^d$;
A³ are each independently CR$^e$, N or NR$^f$;
A⁴ are each independently CR$^g$, N or NR$^h$
R$^a$,
R$^c$, R$^d$,
R$^e$, R$^f$,
R$^g$, R$^h$ are each independently hydrogen, aryl, heteroaryl, alkyl, cycloalkyl, heterocycloalkyl, a crosslinkable or polymerizable group bonded via a spacer;
or
(R$^a$ or R$^b$) and (R$^c$ or R$^d$), or
(R$^e$ or R$^f$ and (R$^g$ or R$^h$), and/or
(R$^c$ or R$^d$) and (R$^e$ or R$^f$)
form, together with the carbon or nitrogen atom, a cyclic radical which has 3 to 10 ring atoms and may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;
where the C group is bonded in the 2 and/or 4 position, or
two units of the general formula (III) are bridged to one another via a bond, a linear or branched, saturated or unsaturated bridge optionally interrupted by at least one heteroatom or via 0, where this bridge in the general formula (III) is bonded in place of R$^a$, R$^b$, R$^c$, R$^d$, R$^e$, R$^f$, R$^g$, R$^h$, R¹³, R¹⁴ or via and/or in place of R².

With regard to the radicals or groups X, R², C, and accordingly also R³, R⁴, R⁵, R⁶, R⁷, R⁸, R⁹, R¹⁰, R¹¹, R¹², m, p, s, A¹, A², A³, A⁴, in the compound of the general formula (III) or any bridge present between two units of the general formula (III), corresponding polymeric or crosslinked compounds and the corresponding preferred embodiments, the statements made for the compound of the general formula (I) used in accordance with the invention apply.

The inventive compounds of the general formula (III) are notable for the specific combination of at least one carbazolyl substituent with at least one five-membered heterocycle bonded via a nitrogen atom as a further substituent. By virtue of this inventive feature of the compounds of the general formula (III), these compounds can be used particularly advantageously in organic electronics, for example in OLEDs.

In one embodiment, the radical C in the compound of formula (III) is defined as follows:
C is a five-membered saturated or unsaturated heterocyclic radical of the general formula (II)

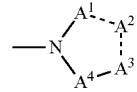

(II)

where
A¹ are each independently CR$^a$, N or NR$^b$;
A² are each independently CR$^c$, N or NR$^d$;
A³ are each independently CR$^e$, N or NR$^f$;
A⁴ are each independently CR$^g$, N or NR$^h$
R$^a$, R$^b$,
R$^c$, R$^d$,
R$^e$, R$^f$,
R$^g$, R$^h$ are each independently hydrogen, aryl, heteroaryl, alkyl, cycloalkyl, heterocycloalkyl, a crosslinkable or polymerizable group bonded via a spacer.

Preferred radicals C in formula (III) are mentioned below.
In the inventive compounds of the general formula (III), at least one carbazolyl substituent of the general formula (IV)

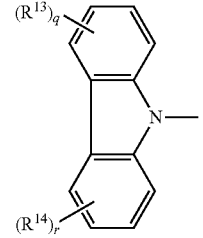

(IV)

is present, preferably bonded in the 8 position.

The present invention therefore more preferably relates to an inventive compound of the general formula (III), wherein a carbazolyl substituent (IV)

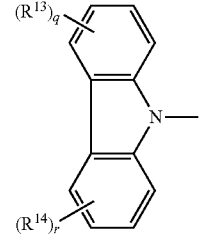

(IV)

is present bonded in the 8 position of the dibenzofuran or dibenzothiophene base skeleton.

In the compound of the general formula (III), m is 0, 1, 2 or 3, p is 1 or 2, q is 0, 1, 2, 3 or 4, r is 0, 1, 2, 3 or 4, and s is 1, 2, 3 or 4.

In a preferred embodiment, in the general formula (III), s is 1 or 2, more preferably 1.

In a further preferred embodiment, in the general formula (III), q is 0 or 1, more preferably 0.

In a further preferred embodiment, in the general formula (III), r is 0 or 1, more preferably 0.

In a further embodiment, s in formula (III) is 1, p is 1 and m is 0.

With regard to the $R^{13}$ and $R^{14}$ radicals which occur in the compound of the general formula (III), and the corresponding preferred embodiments, the statements made for the compounds of the general formula (I) used in accordance with the invention apply.

In the inventive compounds of the general formula (III), at least one five-membered saturated or unsaturated heterocyclic C radical of the general formula (II)

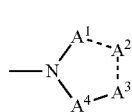

(II)

is present, with the abovementioned definitions of $A^1, A^2, A^3, A^4, R^a, R^b, R^c, R^d, R^e, R^f, R^g$ and $R^h$.

According to the invention, the radical (II) may be saturated or unsaturated. In the case of a saturated C radical, all bonds which occur in the five-membered ring between two nitrogens are $NR^b$, $NR^d$, $NR^f$ and $NR^h$.

In the case of an unsaturated C radical, general formula (II), the bonds which occur in the five-membered ring between N, $A^1, A^2, A^4$ and/or $A^4$ may be corresponding single or double bonds. C radicals which comprise at least one double bond may therefore be unsaturated or have aromatic character. The person skilled in the art is aware that the general formula (II) describes all radicals possible in accordance with the invention, i.e. saturated, unsaturatated and aromatic radicals, even though only dotted single bonds are shown in the drawing. The person skilled in the art knows which bonds in the general formula (II) are single or double bonds and that, in the case of saturated or partly saturated radicals of the general formula (II), further hydrogen atoms are optionally present on the corresponding $A^1, A^2, A^3$ and $A^4$. In partly unsaturated or aromatic C radicals, the $R^a, R^b, R^c, R^d, R^f, R^g$ radicals are not present at the corresponding sites on $A^1, A^2, A^3$ and/or $A^4$. The formulation, for example, "$R^a$ or $R^b$" is selected since, in the inventive compounds, for example, either $R^a$ or $R^b$ etc. is present according to which definitions $A^1, A^2$ etc.

$R^a, R^b, R^c, R^d, R^e, R^g$ and $R^h$ are each independently hydrogen, aryl, heteroaryl, alkyl, cycloalkyl, heterocycloalkyl, a crosslinkable or polymerizable group bonded via a spacer. With regard to the definition of the radicals mentioned and preferred embodiments, the above statements apply. Most preferably, $R^a, R^b, R^c, R^d, R^e, R^f, R^g$ and $R^h$ are each independently hydrogen, alkyl or aryl. $R^a, R^c, R^e$ and $R^g$ are especially preferably each independently hydrogen, alkyl or aryl. $R^b, R^d, R^f$ and $R^h$ are especially preferably each independently alkyl or aryl, which means that preferably no NH is present in the ring.

In a preferred embodiment of the present invention, $A^1$ is $CR^a$ or N, $A^2$ is $CR^c$ or N, $A^3$ is $CR^e$ or N and $A^4$ is $CR^g$ or N.

In this preferred embodiment, no $R^b, R^d, R^f$ and $R^h$ radicals are present.

The general formula (II) preferably corresponds to the following formula (IIa)

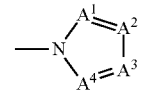

(IIa)

or an isomeric formula thereof with the corresponding abovementioned definitions of $A^1, A^2, A A^3$ and $A^4$; more particularly, in the formula (IIa), $A^1$ is $CR^a$ or N, $A^2$ is $CR^c$ or N, $A^3$ is $CR^e$ or N and $A^4$ is $CR^g$ or N.

In a preferred embodiment, the present invention relates to the inventive compound of the general formula (III) the C group is:

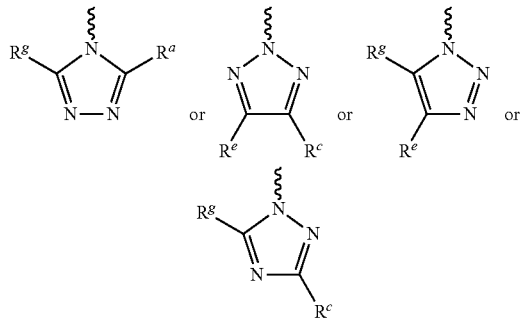

In a further preferred embodiment, the present invention relates to the inventive compound of the general formula (III) the C group is:

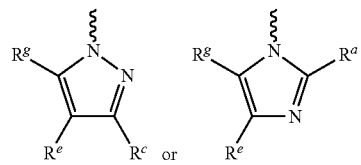

In a further preferred embodiment, the present invention relates to the inventive compound of the general formula (I) the C group is:

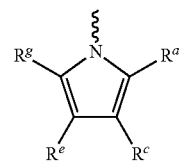

In a further preferred embodiment, the present invention relates to the inventive compound of the general formula (III) wherein at least one of $R^a, R^c, R^e$ and $R^g$ is aryl, preferably optionally substituted phenyl.

In a preferred embodiment of the present invention, $R^a$ and $R^c$ or $R^e$ and $R^g$, and/or, preferably or, $R^c$ and $R^e$ form, together with the carbon atom, a cyclic radical which has 3 to 10 ring atoms and may be unsubstituted or substituted by one or more substituents selected from alkyl, cycloalkyl, heterocycloalkyl, aryl, heteroaryl or a group with donor or acceptor action and/or may be fused to one or more further cyclic radicals having 3 to 10 ring atoms, where the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action.

In a particularly preferred embodiment,
$R^a$ and $R^c$ or
$R^e$ and $R^g$, and/or, preferably or,
$R^c$ and $R^e$
form, together with the carbon atom, a cyclic radical which has 5, 6 or 7 ring atoms and is either unsubstituted or substituted by alkyl groups, for example methyl, and/or aryl groups, for example phenyl.

In this embodiment, in which the $R^a$ and $R^c$ or $R^e$ and $R^g$, and/or, preferably or, $R^c$ and $R^e$ radicals form the abovementioned fused rings, the remaining, i.e. unfused, $R^a$, $R^c$, $R^e$, $R^g$ radicals are preferably aryl, more preferably phenyl or substituted phenyl.

By virtue of the fact that ($R^a$ and $R^c$) or ($R^e$ and $R^g$) or ($R^c$ and $R^e$) preferably form a corresponding abovementioned fused ring, with particular preference in accordance with the invention, only one fused ring is present in the C radical of the general formula (II).

In a further embodiment of the present invention, two units of the general formula (III) are bridged to one another via a bond, i.e. a C—C bond, a C—N bond, a linear or branched, saturated or unsaturated bridge optionally interrupted by at least one heteroatom or via O, where this bridge in the general formula (III) where this bridge in the general formula (III) is bonded in place of $R^a$, $R^b$, $R^c$, $R^d$, $R^e$, $R^f$, $R^g$, $R^h$ or via and/or in place of $R^1$ or $R^2$.

The bridge is preferably selected from the group consisting of a bond, —$CH_2$—, —$C_2H_4$—, —$C_3H_6$—, —$C_4H_8$—, —$C_6H_{12}$—, —$C_8H_{16}$—, —$C_9H_{18}$—, —CH($C_8H_{17}$)$CH_2$—, —$C_2H_4(CF_2)_8C_2H_4$—, —C≡C—, -1,4-$(CH_2)_2$-phenyl-$(CH_2)_2$—, 1,3-$(CH_2)_2$-phenyl-$(CH_2)_2$—, -1,4-phenyl-, -1,3-phenyl-, —O—, —O—Si$(CH_3)_2$—O— or —O—Si$(CH_3)_2$—O—Si$(CH_3)_2$—O—. The bridge is most preferably a bond or -1,3-phenyl-.

The inventive bridged compounds most preferably correspond to the following general formula (IIIa) or (IIIb)

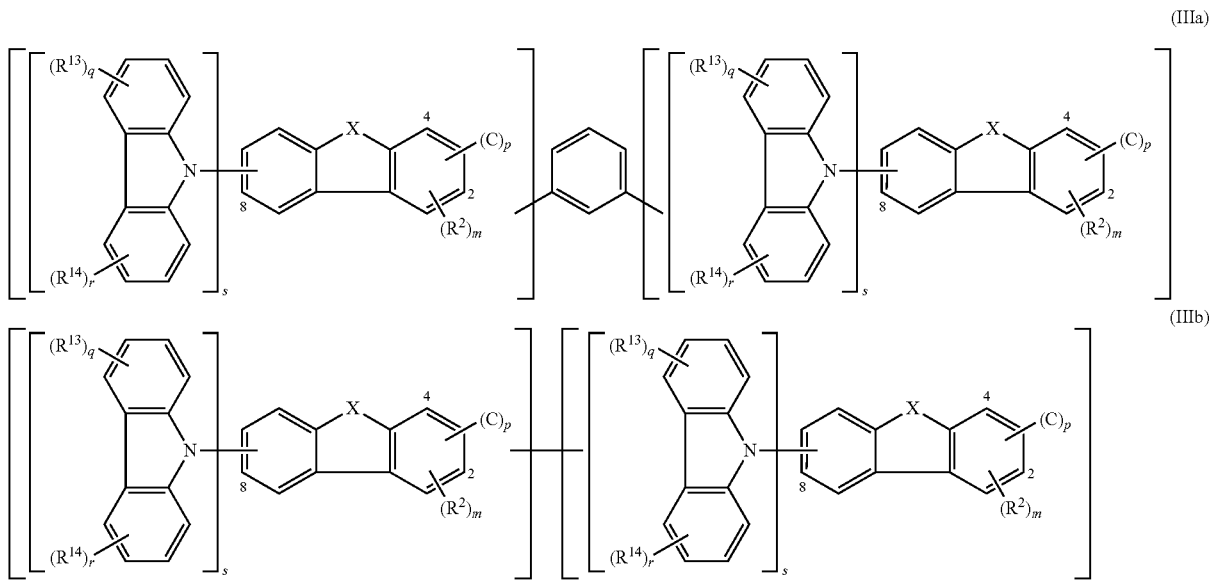

with the abovementioned definitions of $R^2$, $R^{13}$, $R^{14}$, X, C, m, p, s, r and q. Preferably, in this embodiment, m, q and r are each 0, and p and s are each 1.

In a very particularly preferred embodiment, the present invention therefore relates to compounds of the general formula (III) selected from the following group:

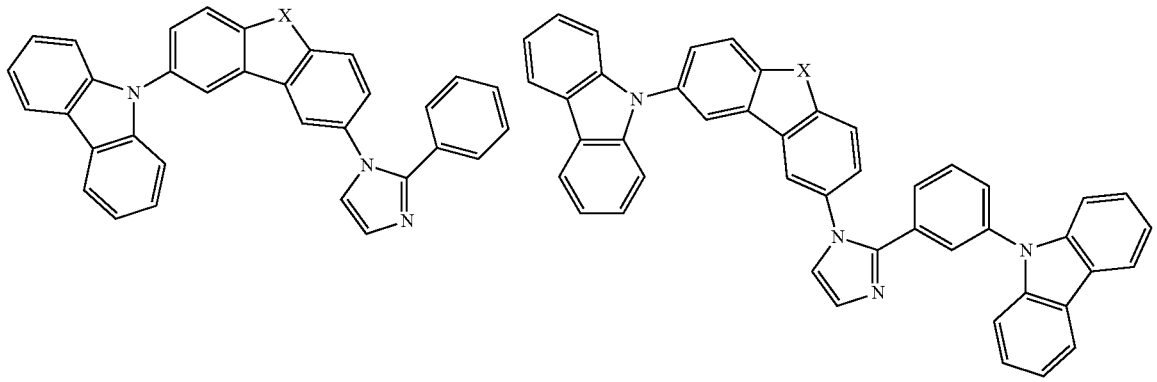

-continued
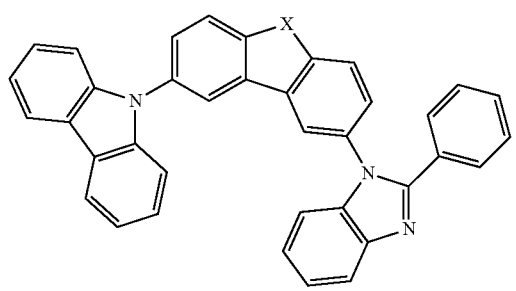
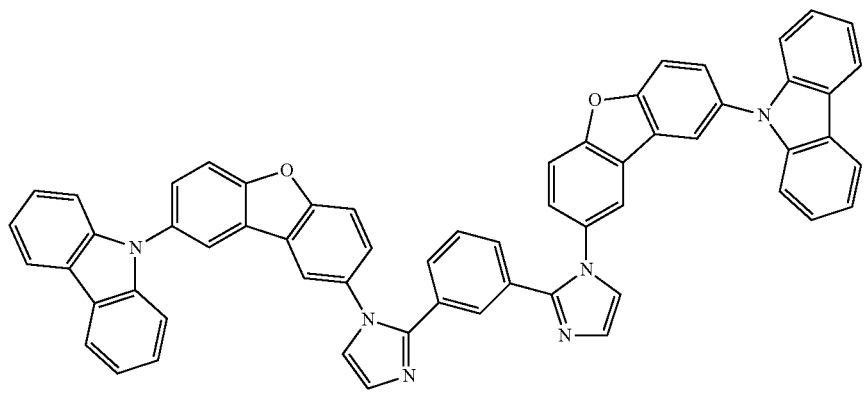
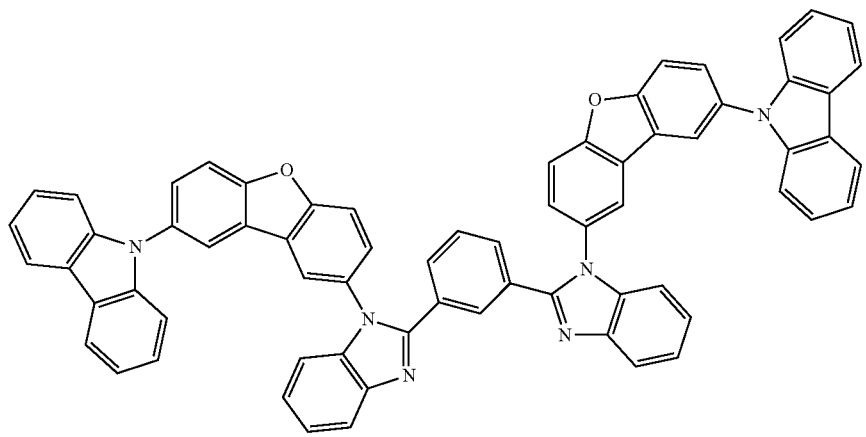
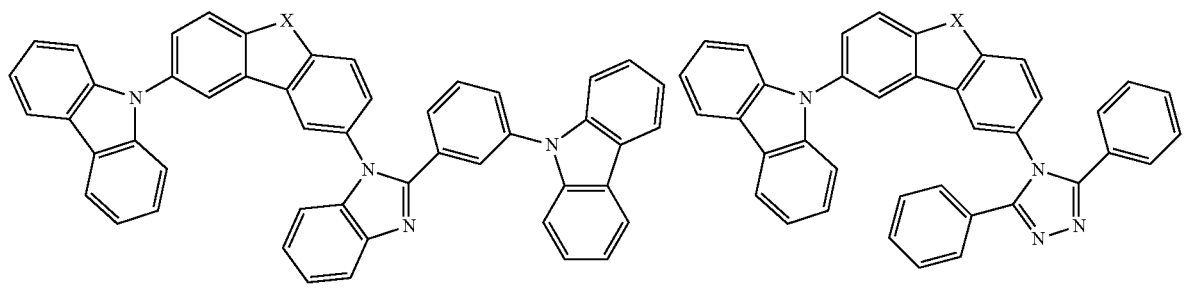

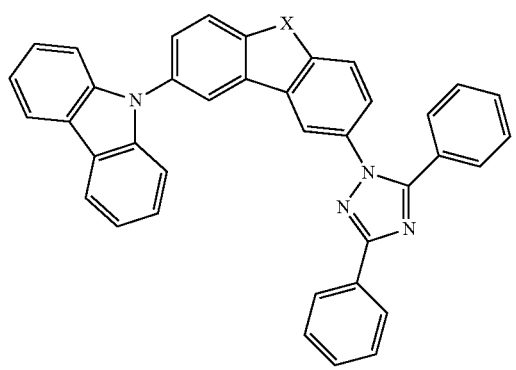
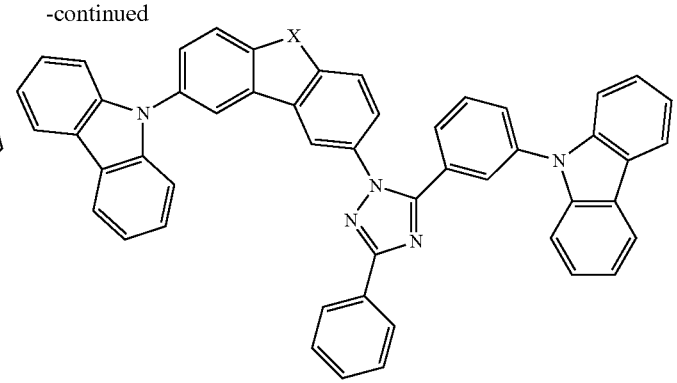

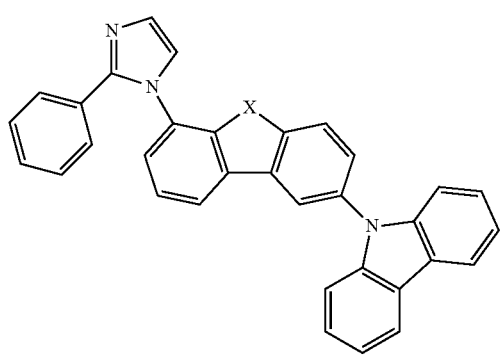
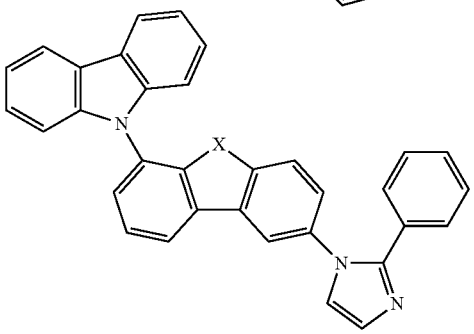

where X is S or O.

The present invention also relates to a process for preparing the inventive compounds of the formula (III), wherein the at least one carbazolyl radical (IV)

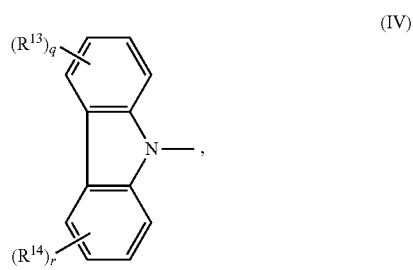

the optionally substituted five-membered nitrogen heterocycles C and optionally $R^2$ radicals are introduced into a base skeleton of the formula (V) according to one of the following variants a) or b)

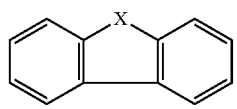

where X is O or S,
variant a)
ia) preparation of a precursor compound suitable for introduction of the carbazolyl radical(s) (IV), and optionally of the $R^2$ radical(s) and of the C radical(s),
iia) introduction of the carbazolyl radical(s) (IV),
iiia) introduction of the C radical(s) or of a precursor thereof, and, if present, introduction of the $R^2$ radical(s),
iva) if appropriate, conversion of the precursor of C to the C radical,
or
variant b)
ib) preparation of a precursor compound suitable for introduction of the carbazolyl radical(s) (IV), and optionally of the $R^2$ radical(s) and of the C radical(s),
iib) introduction of the C radical(s) or of a precursor thereof,
iiib) introduction of the carbazolyl radical(s) (IV), and, if present, introduction of the $R^2$ radical(s),
ivb) if appropriate, conversion of the precursor of C to the C radical.
Step ia) or ib):

Suitable precursor compounds for introduction of the carbazolyl radical(s) (IV) and of the C radical(s) are especially the corresponding halogenated, preferably brominated, compounds of the general formula (V*):

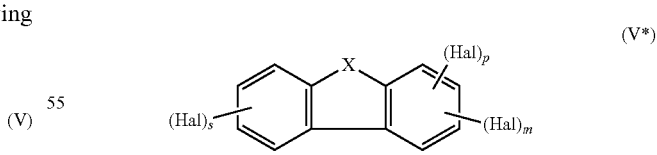

where Hal is halogen, preferably bromine or iodine, more preferably bromine, m, p and are each as defined in formula (III), and X is S or O.

The halogenation can be performed by the processes known to those skilled in the art. Preference is given to bromination or iodination in the 2, 4 and 8 positions, or in the 2 and 8 positions or in the 4 and 8 positions.

Optionally substituted dibenzofurans, dibenzothiophenes can be dibrominated in the 2,8 positions (dibenzofuran and dibenzothiophene) with bromine or NBS in glacial acetic acid or in chloroform. Suitable processes are described, for example, for X=S in W. Yang et al., *J. Mater. Chem.* 2003, 13, 1351. In addition, 2,8-dibromodibenzothiophene, 2,8-dibromodibenzofuran, 3-bromodibenzothiophene, 3-bromodibenzofuran, 2-bromodibenzothiophene and 2-bromodibenzofuran are commercially available.

Monobromination in the 4 position of dibenzofuran (and analogously for dibenzothiophene) is described, for example, in J. Am. Chem. Soc. 1984, 106, 7150.

Monobromination in the 2 position of dibenzofuran or dibenzothiophene is effected analogously to the dibromination, except that only one equivalent of bromine or NBS is added.

Preference is also given to using iodinated dibenzofurans, dibenzothiophenes. It is also possible to use mixed (once iodinated+once brominated) compounds.

The preparation is described, inter alia, in *Tetrahedron. Lett.* 2006, 47, 6957-6960, *Eur. J. Inorg. Chem.* 2005, 24, 4976-4984, *J. Heterocyclic Chem.* 2002, 39, 933-941, *J. Am. Chem. Soc.* 2002, 124, 11900-11907, *J. Heterocyclic Chem.* 2001, 38, 77-87.

For the nucleophilic substitution, Cl- or F-substituted dibenzofurans, dibenzothiophenes and carbazoles are required. The chlorination is described, inter alia, in *J. Heterocyclic Chemistry,* 1997, 34, 891-900, *Org. Lett.,* 2004, 6, 3501-3504; *J. Chem. Soc. [Section] C: Organic,* 1971, 16, 2775-7, *Tetrahedron Lett.* 1984, 25, 5363-6, *J. Org. Chem.* 2004, 69, 8177-8182. The fluorination is described in *J. Org. Chem.* 1998, 63, 878-880 and *J. Chem. Soc., Perkin Trans.* 2 2002, 5, 953-957.

Step iia) or iiib):

The carbazolyl radical(s) (IV) can be introduced by processes known to those skilled in the art.

The (IV) radical is preferably introduced by reaction of the base skeleton of the formula (V*) or of the compound of the formula (V*) with a radical (IV) of the formula (IV), carbazole being present as the N—H precursor.

The introduction of the (IV) radical is performed generally in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH, or $K_2CO_3$.

The N-alkylation (for example disclosed in M. Tosa et al., Heterocycl. Communications, Vol. 7, No. 3, 2001, p. 277-282) or N-arylation or N-heteroarylation (for example (N-arylation) disclosed in H. Gilman and D. A. Shirley, J. Am. Chem. Soc. 66 (1944) 888; D. Li et al., Dyes and Pigments 49 (2001) 181-186) is preferably performed in a solvent. Suitable solvents are, for example, polar aprotic solvents such as dimethyl sulfoxide, dimethylformamide or alcohols. It is likewise possible to use an excess of the alkyl halide or (hetero)aryl halide used as a solvent. The reaction can additionally be performed in a nonpolar aprotic solvent, for example toluene, when a phase transfer catalyst, for example tetra-n-butylammonium hydrogensulfate, is present (as disclosed, for example, in I. Gozlan et al., J. Heterocycl. Chem. 21 (1984) 613-614).

The molar ratio of the compound of the formula (V*) to the compound of the formula (IV)-H is generally 1:1 to 1:15, preferably 1:1 to 1:6, more preferably 1:4.

The N-alkylation or N-(hetero)arylation is performed generally at a temperature of 0 to 220° C., preferably 20 to 200° C. The reaction time is generally 0.5 to 48 h, preferably 1 to 24 h. In general, the N-alkylation or N-arylation is performed at standard pressure.

The resulting crude product is worked up by processes known to those skilled in the art.

Step iiia) or iib):

The introduction of the C radical can be performed by the processes specified for the introduction of the (IV) radical. In general, the C radical is performed in the presence of a base. Suitable bases are known to those skilled in the art and are preferably selected from the group consisting of alkali metal and alkaline earth metal hydroxides such as NaOH, KOH, $Ca(OH)_2$, alkali metal hydrides such as NaH, KH, alkali metal amides such as $NaNH_2$, alkali metal or alkaline earth metal carbonates such as $K_2CO_3$ or $Cs_2CO_3$, and alkali metal alkoxides such as NaOMe, NaOEt. In addition, mixtures of the aforementioned bases are suitable. Particular preference is given to NaOH, KOH, NaH, or $K_2CO_3$.

Heteroarylation can be effected, for example, by copper-catalyzed coupling of the C radical to a halogenated compound of the formula (V*) (Ullmann reaction).

N-Arylation was disclosed, for example, in H. Gilman and D. A. Shirley, J. Am. Chem. Soc. 66 (1944) 888; D. Li et al., Dyes and Pigments 49 (2001) 181-186). The reaction can be performed in solvent or in a melt. Suitable solvents are, for example, (polar) aprotic solvents such as dimethyl sulfoxide, dimethylformamide, NMP, tridecane or alcohols. It is likewise possible to use an excess of one of the starting materials used (compound of the formula (V*) or precursor compound of the C group) as the solvent.

Preference is given to introducing the precursor of the C radical by converting the compound of the formula (V*) in the presence of NaH in DMF (nucleophilic substitution) or by reaction under Cu/base (Ullmann, see above) or Pd catalysis conditions.

The C radical can be obtained by processes known to those skilled in the art for formation of heterocycles. Any precursors of the C radical used can be converted to the corresponding C radicals by processes known to those skilled in the art, for example C2-arylation via Pd coupling.

The N-alkylation or N-(hetero)arylation is performed generally at a temperature of 0 to 220° C., preferably 20 to 200° C. The reaction time is generally 0.5 to 76 h, preferably 1 to 48 h.

The resulting crude product is worked up by processes known to those skilled in the art.

It is possible in accordance with the invention that, in steps iiia) or iib), not the entire C radical is introduced, but rather a precursor compound of the C radical. In this embodiment of the process according to the invention, the precursor compound of the C radical is converted to the full C radical in steps iva) or ivb).

In step iiia) or iiib) of the process according to the invention, if present, the $R^2$, $R^{13}$ and/or $R^{14}$ radicals can be introduced. This can be accomplished in accordance with the invention as in steps iia) or iib).

The present invention also relates to a crosslinked or polymerized material which comprises units of the general formula (III) or a compound of the general formula (I) according to the present invention.

The compounds of the formula (III) used in accordance with the invention, an inventive compound of the general formula (I) or an inventive crosslinked or polymerized material can be used in organic electronics applications selected from switching elements such as organic transistors, for example organic FETs and organic TFTs, organic solar cells and organic light-emitting diodes (OLEDs), preference being given to using the compounds of the formula (III) or (I) in OLEDs.

The present application therefore further provides for the use of the compounds of the formula (III) or a compound of the general formula (I) or an inventive crosslinked or polymerized material in organic electronics applications, preferably in OLEDs.

The present invention also relates to the use of compounds of the formula (III) or of a compound of the general formula (I) according to the present invention or of the inventive crosslinked or polymerized material in formulations for liquid-processed applications in organic electronics.

The compounds of the formula (III), the compound of the general formula (I) or an inventive crosslinked or polymerized material are notable in that they have at least one carbazole substituent and at least one five-membered heterocyclic ring bonded via nitrogen on a dibenzofuran or dibenzothiophene base skeleton. These specific compounds are notable especially in that they ensure good efficiencies, good operative lifetimes and a high stability to thermal stress, and a low use and operating voltage of the organic electronics applications, especially of the OLEDs.

The compounds of the formula (III), the compound of the general formula (I) or an inventive crosslinked or polymerized material can be used as matrix material and/or hole/exciton blocker material and/or electron/exciton blocker material and/or hole injection material and/or electron injection material and/or hole conductor material and/or electron conductor material, preferably as matrix material and/or hole/exciton blocker material and/or electron conductor material, more preferably as electron conductor material, in organic electronics applications, especially in OLEDs. More preferably, the inventive compounds of the formula (III) or the compound of the general formula (I) are used as matrix and/or hole/exciton blocker material and/or electron conductor material, most preferably as electron conductor material, in organic electronics applications, especially in OLEDs.

The use of one of the compounds of the formula (III), of a compound of the general formula (I) or of an inventive crosslinked or polymerized material as electron conductor material and/or matrix material in combination with an emitter material leads to improved efficiency values and a reduction in the voltage in OLEDs at constant luminance, compared to OLEDs which do not comprise any matrix material comprising a compound of the formula (III) or a compound of the general formula (I). The reduced voltage is attributable to a good conductivity of charge carriers, for example of electrons, in the OLED.

In the emission layer or one of the emission layers of an OLED, it is also possible to combine an emitter material with a matrix material of the compound of the formula (III), of the compound of the general formula (I) or an inventive crosslinked or polymerized material and a further matrix material which has, for example, a good hole conductor capacity. This achieves a high quantum efficiency of this emission layer.

Owing to the transport properties and the position of the triplet level and hence the exciton blocker properties of the compounds of the formula (III), of the compound of the general formula (I) or of the inventive crosslinked or polymerized material, these compounds can also be used as hole/exciton blocker material and/or electron/exciton blocker material. Compounds of the formula (III), of the compound of the general formula (I) or an inventive crosslinked or polymerized material have good electron conductor capacity and can especially be used as electron conductor material on the cathode side of an OLED.

When a compound of the formula (III), a compound of the general formula (I) or an inventive crosslinked or polymerized material is used as matrix material in an emission layer and additionally as hole/exciton blocker material and/or electron/exciton blocker material, owing to the chemical identity or similarity of the materials, an improved interface between the emission layer and the adjacent hole/exciton blocker material and/or electron/exciton blocker material is obtained, which can lead to a decrease in the voltage with constant luminance and to an extension of the lifetime of the OLED. Moreover, the use of the same material for hole/exciton blocker material and/or electron/exciton blocker material and for the matrix of an emission layer allows the production process of an OLED to be simplified, since the same source can be used for the application of the material comprising at least one of the compounds of the formula (III), a compound of the general formula (I) or a material crosslinked or polymerized in accordance with the invention.

Suitable structures of the organic electronics applications are known to those skilled in the art and are specified below.

The organic transistor generally includes a semiconductor layer formed from an organic layer with hole transport capacity and/or electron transport capacity; a gate electrode formed from a conductive layer; and an insulating layer introduced between the semiconductor layer and the conductive layer. A source electrode and a drain electrode are mounted on this arrangement in order thus to produce the transistor element. In addition, further layers known to those skilled in the art may be present in the organic transistor. The compound of the formula (III), the compound of the general formula (I) or an inventive crosslinked or polymerized material may be present in any desired layer of the organic transistor.

The organic solar cell (photoelectric conversion element) generally comprises an organic layer present between two plate-type electrodes arranged in parallel. The organic layer may be configured on a comb-type electrode. There is no particular restriction regarding the site of the organic layer and there is no particular restriction regarding the material of the electrodes. When, however, plate-type electrodes arranged in parallel are used, at least one electrode is preferably formed from a transparent electrode, for example an ITO electrode or a fluorine-doped tin oxide electrode. The organic layer is formed from two sublayers, i.e. a layer with p-type semiconductor properties or hole transport capacity, and a layer formed with n-type semiconductor properties or electron transport capacity. In addition, it is possible for further layers known to those skilled in the art to be present in the organic solar cell. The compound of the formula (III), the compound of the general formula (I) or an inventive crosslinked or polymerized material may be present in any desired layer of the organic solar cell, preferably as electron conductor material.

In a further embodiment, the present invention relates to an organic light-emitting diode comprising at least one compound of the formula (III), at least one compound of the general formula (I) or an inventive crosslinked or polymerized material, more preferably as electron conductor material. The compound of the formula (III), the compound of the general formula (I) or an inventive crosslinked or polymerized material can be used in the organic light-emitting diode as matrix material and/or hole/exciton blocker material and/or electron/exciton blocker material and/or hole injection material and/or electron injection material and/or hole conductor material and/or electron conductor material, preferably as matrix material and/or hole/exciton blocker material and/or electron conductor material, more preferably as electron conductor material, in organic electronics applications, especially in OLEDs.

In a preferred embodiment of the invention, compounds of the general formula (III), compounds of the general formula (I) or an inventive crosslinked or polymerized material are used in a mixture, for example together with another hole conductor or electron conductor in the hole-conducting or preferably in the electron-conducting layer. As further hole conductors or electron conductors, it is generally possible to use materials known to those skilled in the art, especially the hole or electron conductors specified below.

In a further embodiment, the present invention relates to an organic light-emitting diode in which the compounds of the formula (III), compounds of the general formula (I) or an inventive crosslinked or polymerized material are used as hole/exciton blockers, preferably in a blocking layer for holes, or in the light-emitting layer, preferably as matrix material.

It is likewise possible that the compounds of the formula (III), the compounds of the general formula (I) or an inventive crosslinked or polymerized material are present both in the light-emitting layer (preferably as matrix material or electron conductor material) and in the blocking layer for holes (as hole/exciton blockers).

In a particularly preferred embodiment, the present invention relates to an OLED in which all layers, i.e. hole conductor, electron blocker, matrix, hole blocker and electron conductor, comprise, more preferably consist of, compounds of the formula (III), compounds of the general formula (I) or a material crosslinked or polymerized in accordance with the invention, the emission layer additionally comprising an emitter.

The present invention further provides an inventive organic light-emitting diode comprising an anode An and a cathode Ka and at least one light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (III) or formula (I) is present in the electron conductor layer and/or light-emitting layer E and/or in at least one of the further layers.

The present invention preferably relates to an inventive organic light-emitting diode wherein at least one inventive compound of the formula (III) or an inventive compound of the general formula (I) or the inventive crosslinked or polymeric material is present in the electron conductor layer and/or in the light-emitting layer and/or in the at least one blocking layer for holes/excitons.

The present application further provides a light-emitting layer comprising at least one compound of the formula (III), a compound of the general formula (I) or an inventive crosslinked or polymerized material.

The present invention further provides an OLED comprising an inventive light-emitting layer.

The present invention additionally relates to a blocking layer for holes/excitons comprising at least one compound of the formula (III), a compound of the general formula (I) or an inventive crosslinked or polymerized material.

The present invention also relates to an electron-conducting layer comprising at least one inventive compound of the formula (III), an inventive compound of the general formula (I) or an inventive polymeric or crosslinked material.

Structure of the Inventive OLED

The inventive organic light-emitting diode (OLED) thus generally has the following structure:

an anode (An) and a cathode (Ka) and a light-emitting layer E arranged between the anode (An) and the cathode (Ka).

The inventive OLED may, for example—in a preferred embodiment—be formed from the following layers:
1. anode
2. hole conductor layer
3. light-emitting layer
4. blocking layer for holes/excitons
5. electron conductor layer
6. cathode Layer sequences different from the aforementioned structure are also possible, and are known to those skilled in the art. For example, it is possible that the OLED does not have all of the layers mentioned; for example, an OLED with layers (1) (anode), (3) (light-emitting layer) and (6) (cathode) is likewise suitable, in which case the functions of the layers (2) (hole conductor layer) and (4) (blocking layer for holes/excitons) and (5) (electron conductor layer) are assumed by the adjacent layers. OLEDs which have layers (1), (2), (3) and (6), or layers (1), (3), (4), (5) and (6), are likewise suitable. In addition, the OLEDs may have a blocking layer for electrons/excitons between the anode (1) and the hole conductor layer (2).

It is additionally possible that a plurality of the aforementioned functions (electron/exciton blocker, hole/exciton blocker, hole injection, hole conduction, electron injection, electron conduction) are combined in one layer and are assumed, for example, by a single material present in this layer. For example, a material used in the hole conductor layer, in one embodiment, may simultaneously block excitons and/or electrons.

Furthermore, the individual layers of the OLED among those specified above may in turn be formed from two or more layers. For example, the hole conductor layer may be formed from a layer into which holes are injected from the electrode, and a layer which transports the holes away from the hole-injecting layer into the light-emitting layer. The electron conduction layer may likewise consist of a plurality of layers, for example a layer in which electrons are injected by the electrode, and a layer which receives electrons from the electron injection layer and transports them into the light-emitting layer. These layers mentioned are each selected according to factors such as energy level, thermal resistance and charge carrier mobility, and also energy difference of the layers specified with the organic layers or the metal electrodes. The person skilled in the art is capable of selecting the structure of the OLEDs such that it is matched optimally to the organic compounds used as emitter substances in accordance with the invention.

In order to obtain particularly efficient OLEDs, for example, the HOMO (highest occupied molecular orbital) of the hole conductor layer should be matched to the work function of the anode, and the LUMO (lowest unoccupied molecular orbital) of the electron conductor layer should be matched to the work function of the cathode, when the aforementioned layers are present in the inventive OLEDs.

The anode (1) is an electrode which provides positive charge carriers. It may be formed, for example, from materials which comprise a metal, a mixture of various metals, a metal alloy, a metal oxide or a mixture of various metal oxides. Alternatively, the anode may be a conductive polymer. Suitable metals comprise metals and alloys of the metals of the main groups, transition metals and of the lanthanoids, especially the metals of groups Ib, IVa, Va and VIa of the periodic table of the elements, and the transition metals of group VIIIa. When the anode is to be transparent, generally mixed metal oxides of groups IIb, IIIb and IVb of the periodic table of the elements (old IUPAC version) are used, for example indium tin oxide (ITO). It is likewise possible that the anode (1) comprises an organic material, for example polyaniline, as described, for example, in Nature, vol. 357, pages 477 to 479 (Jun. 11, 1992). At least either the anode or the cathode should be at least partly transparent in order to be able to emit the light formed. The material used for the anode (1) is preferably ITO.

Suitable hole conductor materials for layer (2) of the inventive OLEDs are disclosed, for example, in Kirk-Othmer Encyclopedia of Chemical Technology, 4th edition, vol. 18, pages 837 to 860, 1996. Both hole-transporting molecules and polymers can be used as hole transport material. Hole-transporting molecules typically used are selected from the group consisting of tris-[N-(1-naphthyl)-N-(phenylamino)] triphenylamine (1-naphDATA), 4,4'-bis[N-(1-naphthyl)-N-phenyl-amino]biphenyl (α-NPD), N,N'-diphenyl-N,N'-bis (3-methylphenyl)-[1,1'-biphenyl]-4,4'-diamine (TPD), 1,1-bis[(di-4-tolylamino)phenyl]cyclohexane (TAPC), N,N'-bis (4-methylphenyl)-N,N'-bis(4-ethylphenyl)-[1,1'-(3,3'-dimethyl)biphenyl]-4,4'-diamine (ETPD), tetrakis(3-methylphenyl)-N,N,N',N'-2,5-phenylenediamine (PDA), α-phenyl-4-N,N-diphenylaminostyrene (TPS), p-(diethylamino)benzaldehyde diphenylhydrazone (DEH), triphenylamine (TPA), bis[4-(N,N-diethylamino)-2-methylphenyl] (4-methylphenyl)methane (MPMP), 1-phenyl-3-[p-(diethylamino)styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4',4"-tris(N,N-diphenylamino)triphenylamine (TDTA), 4,4',4"-tris (N-carbazolyl)triphenylamine (TCTA), N,N'-bis (naphthalen-2-yl)-N,N'-bis(phenyl)benzidine (β-NPB), N,N'-bis(3-methylphenyl)-N,N'-bis(phenyl)-9,9-spirobifluorene (spiro-TPD), N,N'-bis(naphthalen-1-yl)-N,N'-bis (phenyl)-9,9-spirobifluorene (spiro-NPB), N,N'-bis(3-methylphenyl)-N,N'-bis(phenyl)-9,9-dimethylfluorene (DMFL-TPD), Di-[4-(N,N-ditolylamino)phenyl]cyclohexane, N,N'-bis(naphthalen-1-yl)-N,N'-bis(phenyl)-9,9-dimethylfluorene, N,N'-bis(naphthalen-1-yl)-N,N'-bis (phenyl)-2,2-dimethylbenzidine, N,N'-bis(naphthalen-1-yl)-N,N'-bis(phenyl)benzidine, N,N'-bis(3-methylphenyl)-N, bis(phenyl)benzidine, 2,3,5,6-tetrafluoro-7,7,8,8-tetracyanoquinodimethane (F4-TCNQ), 4,4',4"-tris(N-3-methylphenyl-N-phenylamino)triphenylamine, 4,4',4"-tris(N-(2-naphthyl)-N-phenylamino)triphenylamine, pyrazino[2,3-f] [1,10]phenanthroline-2,3-dicarbonitrile (PPDN), N,N,N',N'-tetrakis(4-methoxyphenyl)benzidine (MeO-TPD), 2,7-bis [N,N-bis(4-methoxyphenyl)amino]-9,9-spirobifluorene (MeO-spiro-TPD), 2,2'-bis[N,N-bis(4-methoxyphenyl) amino]-9,9-spirobifluorene (2,2'-MeO-spiro-TPD), N,N'-diphenyl-N,N'-di[4-(N,N-ditolylamino)phenyl]benzidine (NTNPB), N,N'-diphenyl-N,N'-di[4-(N,N-diphenylamino) phenyl]benzidine (NPNPB), N,N'-di(naphthalen-2-yl)-N,N'-diphenylbenzene-1,4-diamine (β-NPP), N,N'-bis(3-methylphenyl)-N,N'-bisphenyl-9,9-diphenylfluorene (DPFL-TPD), N,N'-bis(naphthalen-1-yl)-N,N'-bisphenyl-9,9-diphenylfluorene (DPFL-NPB), 2,2',7,7'-tetrakis(N,N-diphenylamino)-9,9'-spirobifluorene (spiro-TAD), 9,9-bis[4-N,N-bis(biphenyl-4-yl)amino)phenyl]-9H-fluorene (BPAPF), 9,9-bis[4-(N,N-bis(naphthalen-2-yl)amino)phenyl]-9H-fluorene (NPAPF), 9,9-bis[4-(N,N-bis(naphthalen-2-yl)-N,N'-bisphenylamino)phenyl]-9H-fluorene (NP-BAPF), 2,2',7,7'-tetrakis[N-naphthalenyl(phenyl)amino]-9, 9'-spirobifluorene (spiro-2NPB), N,N'-bis(phenanthren-9-yl)-N,N'-bis(phenyl)benzidine (PAPB), 2,7-bis[N,N-bis(9,9-spirobifluoren-2-yl)amino]-9,9-spirobifluorene (spiro-5), 2,2'-bis[N,N-bis(biphenyl-4-yl)amino]-9,9-spirobifluorene (2,2'-spiro-DBP), 2,2'-bis(N,N-diphenylamino)-9,9-spirobifluorene (spiro-BPA), 2,2',7,7'-tetra(N,N-ditolyl)amino-spirobifluorene (spiro-TTB), N,N,N',N'-tetranaphthalen-2-ylbenzidine (TNB), porphyrin compounds, and phthalocyanines such as copper phthalocyanines and titanium oxide phthalocyanines. Hole-transporting polymers typically used are selected from the group consisting of polyvinylcarbazoles, (phenylmethyl)polysilanes and polyanilines. It is likewise possible to obtain hole-transporting polymers by doping hole-transporting molecules into polymers such as polystyrene and polycarbonate. Suitable hole-transporting molecules are the molecules already mentioned above.

In addition—in one embodiment—carbene complexes can be used as hole conductor materials, in which case the band gap of the at least one hole conductor material is generally greater than the band gap of the emitter material used. In the context of the present application, "band gap" is understood to mean the triplet energy. Suitable carbene complexes are as described, for example, in WO 2005/019373 A2, WO 2006/056418 A2, WO 2005/113704, WO 2007/115970, WO 2007/115981 and WO 2008/000727. One example of a suitable carbene complex is Ir(dpbic)$_3$ with the formula:

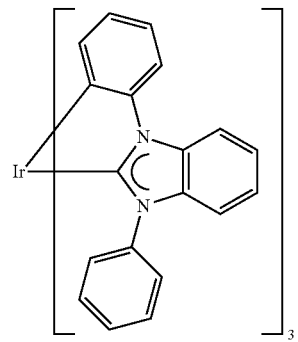

which is disclosed, for example, in WO2005/019373. In principle, it is possible that the hole conductor layer comprises at least one compound of the formula (III) or a compound of the general formula (I) as hole conductor material.

The light-emitting layer (3) comprises at least one emitter material. This may in principle be a fluorescence or phosphorescence emitter, suitable emitter materials being known to those skilled in the art. The at least one emitter material is preferably a phosphorescence emitter. The phosphorescence emitter compounds used with preference are based on metal complexes, and especially the complexes of the metals Ru, Rh, Ir, Pd and Pt, in particular the complexes of Ir, have gained significance. The compounds of the formula (III) or the compounds of the general formula (I) or an inventive crosslinked or polymerized material can be used as a matrix in the light-emitting layer.

Suitable metal complexes for use in the inventive OLEDs are described, for example, in documents WO 02/60910 A1, US 2001/0015432 A1, US 2001/0019782 A1, US 2002/0055014 A1, US 2002/0024293 A1, US 2002/0048689 A1, EP 1 191 612 A2, EP 1 191 613 A2, EP 1 211 257 A2, US 2002/0094453 A1, WO 02/02714 A2, WO 00/70655 A2, WO 01/41512 A1, WO 02/15645 A1, WO 2005/019373 A2, WO 2005/113704 A2, WO 2006/115301 A1, WO 2006/067074 A1, WO 2006/056418, WO 2006/21811 A1, WO 2007/095118 A2, WO 2007/115970, WO 2007/115981 and WO 2008/000727.

Further suitable metal complexes are the commercially available metal complexes tris(2-phenylpyridine)iridium (III), iridium(III) tris(2-(4-tolyl)pyridinato-N,$C^{2'}$), bis(2-phenylpyridine)(acetylacetonato)iridium(III), iridium(III) tris(1-phenylisoquinoline), iridium(III) bis(2,2'-benzothienyl)pyridinato-N,$C^{3'}$)(acetylacetonate), tris(2-phenylquinoline)iridium(III), iridium(III) bis(2-(4,6-difluorophenyl)pyridinato-N,$C^2$)picolinate, iridium(III) bis(1-phenylisoquinoline)(acetylacetonate), bis(2-phenylquinoline)(acetylacetonato)iridium(III), iridium(III) bis(dibenzo[f,h]quinoxaline)(acetylacetonate), iridium(III) bis(2-methyldibenzo[f,h]quinoxaline)(acetylacetonate) and tris(3-methyl-1-phenyl-4-trimethylacetyl-5-pyrazolino)terbium(III), bis[1-(9,9-dimethyl-9H-fluoren-2-ypisoquinoline](acetylacetonato)iridium(III), bis(2-phenylbenzothiazolato)(acetylacetonato)iridium(III), bis(2-(9,9-dihexylfluorenyl)-1-pyridine)(acetylacetonato)iridium (III), bis(2-benzo[b]thiophen-2-yl-pyridine)(acetylacetonato)iridium(III).

In addition, the following commercially available materials are suitable: tris(dibenzoylacetonato)mono(phenanthroline)europium(III), tris(dibenzoylmethane)mono(phenanthroline)europium(III), tris(dibenzoylmethane)mono(5-aminophenanthroline)europium(III), tris(di-2-naphthoylmethane)mono(phenanthroline)europium(III), tris (4-bromobenzoylmethane)mono(phenanthroline)europium (III), tris(di(biphenyl)methane)mono(phenanthroline) europium(III), tris(dibenzoylmethane)mono(4,7-diphenylphenanthroline)europium(III), tris (dibenzoylmethane)mono(4,7-dimethylphenanthroline) europium(III), tris(dibenzoylmethane)mono(4,7-dimethylphenanthrolinedisulfonic acid)europium(III) disodium salt, tris[di(4-(2-(2-ethoxyethoxy)ethoxy)benzoyl-methane)]mono(phenanthroline)europium(III) and tris[d][4-(2-(2-ethoxyethoxy)ethoxy)benzoylmethane)]mono(5-aminophenanthroline)europium(III), osmium(II) bis(3-(trifluoromethyl)-5-(4-tert-butylpyridyl)-1,2,4-triazolato) diphenylmethylphosphine, osmium(II) bis(3-(trifluoromethyl)-5-(2-pyridyl)-1,2,4-triazole) dimethylphenylphosphine, osmium(II) bis(3-(trifluoromethyl)-5-(4-tert-butylpyridyl)-1,2,4-triazolato) dimethylphenylphosphine, osmium(II) bis(3-(trifluoromethyl)-5-(2-pyridyl)-pyrazolato) dimethylphenylphosphine, tris[4,4'-di-tert-butyl(2,2')-bipyridine]ruthenium(III), osmium(II) bis(2-(9,9-dibutylfluorenyl)-1-isoquinoline(acetylacetonate).

Suitable triplet emitters are, for example, carbene complexes. In one embodiment of the present invention, the compounds of the formula (III) or the compounds of the general formula (I) are used in the light-emitting layer as a matrix material together with carbene complexes as triplet emitters. Suitable carbene complexes are known to those skilled in the art and are described, for example, in WO 2005/019373 A2, WO 2006/056418 A2, WO 2005/113704, WO 2007/115970, WO 2007/115981 and WO 2008/000727.

The light-emitting layer may comprise further components in addition to the emitter material. For example, a fluorescent dye may be present in the light-emitting layer in order to alter the emission color of the emitter material. In addition—in a preferred embodiment—a matrix material can be used. This matrix material may be a polymer, for example poly(N-vinylcarbazole) or polysilane. The matrix material may, however, likewise be a small molecule, for example 4,4'-N,N'-dicarbazolebiphenyl (CDP=CBP) or tertiary aromatic amines, for example TCTA. In a preferred embodiment of the present invention, at least one compound of the formula (III) or a compound of the general formula (I) is used as a matrix material.

In a preferred embodiment, the light-emitting layer is formed from 2 to 20% by weight, preferably 5 to 17% by weight, of at least one of the aforementioned emitter materials and 80 to 98% by weight, preferably 83 to 95% by weight, of at least one of the aforementioned matrix materials—in one embodiment at least one compound of the formula (III), a compound of the general formula (I) or an inventive crosslinked or polymerized material—where the sum total of the emitter material and of the matrix material adds up to 100% by weight.

In a further embodiment, the compounds of the formula (III), the compounds of the general formula (I) or an inventive crosslinked or polymerized material is used as hole/exciton blocker material, preferably together with carbene complexes as triplet emitters. The compounds of the formula (III), the compounds of the general formula (I) or an inventive crosslinked or polymerized material may additionally—as mentioned above—be used as matrix materials or both as matrix materials and as hole/exciton blocker materials together with carbene complexes as triplet emitters. In addition, it is possible that at least one compound of the formula (III), the compounds of the general formula (I) or an inventive crosslinked or polymerized material is present in a blocking layer for holes/excitons, a blocking layer for electrons/excitons, a hole injection layer, a hole conductor layer, an electron injection layer and/or an electron conductor layer of the OLED, preferably together with carbene complexes as triplet emitters.

Suitable metal complexes for use together with the compounds of the formula (III), the compounds of the general formula (I) or an inventive crosslinked or polymerized material as matrix material and/or hole/exciton blocker material and/or electron/exciton blocker material and/or hole injection material and/or electron injection material and/or hole conductor material and/or electron conductor material, preferably as matrix material and/or hole/exciton blocker material and/or electron conductor material, most preferably as electron conductor material, in OLEDs are thus, for example, also carbene complexes as described in WO 2005/019373 A2, WO 2006/056418 A2, WO 2005/113704, WO 2007/115970, WO 2007/115981 and WO 2008/000727. Reference is hereby made explicitly to the disclosure of the WO applications cited, and these disclosures shall be considered to be incorporated into the content of the present application.

If the blocking layer for holes/excitons (4) does not comprise any compounds of the formula (III), any compounds of the general formula (I) or an inventive crosslinked or polymerized material, the OLED has—if a blocking layer for holes is present—hole blocker materials typically used in OLEDs, such as 2,6-bis(N-carbazolyl)pyridine (mCPy), 2,9-dimethyl-4,7-diphenyl-1,10-phenanthroline (bathocuproin, (BCP)), bis(2-methyl-8-quinolinato)-4-phenylphenylato) aluminum(III) (BAlq), phenothiazine S,S-dioxide derivatives and 1,3,5-tris(N-phenyl-2-benzylimidazole)benzene) (TPBI), TPBI also being suitable as electron-conducting material. Further suitable hole blockers and/or electron conductor materials are 2,2',2"-(1,3,5-benzenetriyl)tris(1-phenyl-1H-benzimidazole), 2-(4-biphenylyl)-5-(4-tert-butylphenyl)-1,3,4-oxadiazole, 8-hydroxyquinolinolatolithium, 4-(naphthalen-1-yl)-3,5-diphenyl-4H-1,2,4-triazole, 1,3-bis[2-(2,2'-bipyridin-6-yl)-1,3,4-oxadiazol-5-yl]benzene, 4,7-diphenyl-1,10-phenanthroline, 3-(4-biphenylyl)-4-phenyl-5-tert-butylphenyl-1,2,4-triazole, 6,6'-bis[5-(biphenyl-4-yl)-1,3,4-oxadiazol-2-yl]-2,2'-bipyridyl, 2-phenyl-9,10-di(naphthalen-2-yl)anthracene, 2,7-bis[2-(2,2'-bipyridin-6-yl)-1,3,4-oxadiazol-5-yl]-9,9-dimethylfluorene, 1,3-bis[2-(4-tert-butylphenyl)-1,3,4-oxadiazol-5-yl]benzene, 2-(naphthalen-2-yl)-4,7-diphenyl-1,10-phenanthroline, tris(2,4,6-trimethyl-3-(pyridin-3-yl)phenyl)borane, 2,9-bis(naphthalen-2-yl)-4,7-diphenyl-1,10-phenanthroline, 1-methyl-2-(4-(naphthalen-2-yl)phenyl)-1H-imidazo[4,5-f][1,10]-phenanthroline. In a further embodiment, it is possible to use compounds which comprise aromatic or heteroaromatic rings joined via groups comprising carbonyl groups, as disclosed in WO2006/100298, disilyl compounds selected from the group consisting of disilylcarbazoles, disilylbenzofurans, disilylbenzothiophenes, disilylbenzophospholes, disilylbenzothiophene S-oxides and disilylbenzothiophene S,S-dioxides, as specified, for example, in PCT applications WO 2009/003919 and WO 2009/000872, and disilyl compounds as disclosed in WO2008/034758, as a blocking layer for holes/excitons (4) or as matrix materials in the light-emitting layer (3).

In a preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and optionally further layers, wherein the blocking layer for holes/excitons, the electron conductor layer or the light-emitting layer comprises at least one compound of the formula (III) or at least one compound of the general formula (I).

In a further preferred embodiment, the present invention relates to an inventive OLED comprising the layers (1) anode, (2) hole conductor layer, (3) light-emitting layer, (4) blocking layer for holes/excitons, (5) electron conductor layer and (6) cathode, and optionally further layers, wherein the light-emitting layer (3) comprises at least one compound of the formula (III) or at least one compound of the general formula (I) and the blocking layer for holes/excitons and/or the electron conductor layer comprises at least one compound of the formula (III) or at least one compound of the general formula (I).

Suitable further electron conductor materials which can be used in addition to the inventive compounds and materials in the layer (5) of the inventive OLEDs comprise metals chelated to oxinoid compounds, such as 2,2',2''-(1,3,5-phenylene)tris[1-phenyl-1H-benzimidazole] (TPBI), tris(8-quinolinolato)aluminum (Alq$_3$), compounds based on phenanthroline, such as 2,9-dimethyl-4,7-diphenyl-1,10-phenanthroline (DDPA=BCP) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ), 8-hydroxyquinolinolatolithium (Liq), 4,7-diphenyl-1,10-phenanthroline (BPhen), bis(2-methyl-8-quinolinolato)-4-(phenylphenolato)aluminum (BAlq), 1,3-bis[2-(2,2'-bipyridin-6-yl)-1,3,4-oxadiazo-5-yl]benzene (Bpy-OXD), 6,6'-bis[5-(biphenyl-4-yl)-1,3,4-oxadiazo-2-yl]-2,2'-bipyridyl (BP-OXD-Bpy), 4-(naphthalen-1-yl)-3,5-diphenyl-4H-1,2,4-triazole (NTAZ), 2,9-bis(naphthalen-2-yl)-4,7-diphenyl-1,10-phenanthroline (NBphen), 2,7-bis[2-(2,2'-bipyridin-6-yl)-1,3,4-oxadiazo-5-yl]-9,9-dimethylfluorene (Bby-FOXD), 1,3-bis[2-(4-tert-butylphenyl)-1,3,4-oxadiazo-5-yl]benzene (OXD-7), tris(2,4,6-trimethyl-3-(pyridin-3-yl)phenyl)borane (3TPYMB), 1-methyl-2-(4-(naphthalen-2-yl)phenyl)-1H-imidazo[4,5-f][1,10]phenanthroline (2-NPIP), 2-phenyl-9,10-di(naphthalen-2-yl)anthracene (PADN), 2-(naphthalen-2-yl)-4,7-diphenyl-1,10-phenanthroline (HNBphen). The layer (5) may serve both to facilitate electron transport and as a buffer layer or barrier layer in order to prevent quenching of the exciton at the interfaces of the layers of the OLED. The layer (5) preferably improves the mobility of the electrons and reduces quenching of the exciton. In a preferred embodiment, TPBI is used as the electron conductor material. In principle, it is possible and preferred that the electron conductor layer comprises at least one compound of the formula (III), at least one compound of the general formula (I) or an inventive crosslinked or polymerized material as electron conductor material.

Among the materials mentioned above as hole conductor materials and electron conductor materials, some may fulfill several functions. For example, some of the electron-conducting materials are simultaneously hole-blocking materials when they have a low-lying HOMO. These may be used, for example, in the blocking layer for holes/excitons (4). However, it is likewise possible that the function as a hole/exciton blocker is also assumed by layer (5), such that layer (4) can be dispensed with.

The charge transport layers may also be electronically doped in order to improve the transport properties of the materials used, in order firstly to make the layer thicknesses more generous (avoidance of pinholes/short circuits) and in order secondly to minimize the operating voltage of the device. p-Doping is achieved by the addition of oxidizing materials. These mixtures may, for example, be mixtures of the abovementioned hole transport materials with $MoO_2$, $MoO_3$, $WO_x$, $ReO_3$, $V_2O_5$, 7,7,8,8-tetracyanoquinodimethane (TCNQ), 2,3,5,6-tetrafluoro-7,7,8,8-tetracyanoquinodimethane ($F_4$-TCNQ), 2,5-bis(2-hydroxy-ethoxy)-7,7,8,8-tetracyanoquinodimethane, bis(tetra-n-butylammonium)tetracyanodiphenoquinodimethane, 2,5-dimethyl-7,7,8,8-tetracyanoquinodimethane, tetracyanoethylene, 11,11,12,12-tetracyanonaphtho-2,6-quinodimethane, 2-fluoro-7,7,8,8-tetracyanoquinodimethane, 2,5-difluoro-7,7,8,8-tetracyanoquinodimethane, dicyanomethylene-1,3,4,5,7,8-hexafluoro-6H-naphthalen-2-ylidene)-malononitrile ($F_6$-TNAP), Mo(tfd)$_3$ (from Kahn et al., J. Am. Chem. Soc. 2009, 131 (35), 12530-12531), and with quinone compounds as mentioned in EP 09153776.1.

The further electron conductor materials may, for example, be doped with alkali metals, for example Alq$_3$ with lithium. In addition, electron conductors can be doped with salts such as $Cs_2CO_3$. Electronic doping is known to those skilled in the art and is disclosed, for example, in W. Gao, A. Kahn, J. Appl. Phys., Vol. 94, No. 1, 1 Jul. 2003 (p-doped organic layers); A. G. Werner, F. Li, K. Harada, M. Pfeiffer, T. Fritz, K. Leo. Appl. Phys. Lett., Vol. 82, No. 25, 23 Jun. 2003 and Pfeiffer et al., Organic Electronics 2003, 4, 89-103. For example, the hole conductor layer may be doped, in addition to a carbene complex, e.g. Ir(dpbic)$_3$, with $MoO_3$ or $WO_3$.

The cathode (6) is an electrode which serves to introduce electrons or negative charge carriers. Suitable materials for the cathode are selected from the group consisting of alkali metals of group Ia, for example Li, Cs, alkaline earth metals of group IIa, for example calcium, barium or magnesium, metals of group IIb of the periodic table of the elements (old IUPAC version), comprising the lanthanides and actinides, for example samarium. In addition, it is also possible to use metals such as aluminum or indium, and combinations of all metals mentioned. In addition, lithium-comprising organometallic compounds or LiF can be applied between the organic layer and the cathode in order to reduce the operating voltage.

The OLED according to the present invention may additionally comprise further layers which are known to those skilled in the art. For example, between the layer (2) and the light-emitting layer (3) may be applied a layer which facilitates the transport of the positive charge and/or matches the band gap of the layers to one another. Alternatively, this further layer may serve as a protective layer. In an analogous manner, additional layers may be present between the light-emitting layer (3) and the layer (4) in order to facilitate the transport of the negative charge and/or to match the band gap between the layers to one another. Alternatively, this layer may serve as a protective layer.

In a preferred embodiment of the inventive OLED, all layers, i.e. hole conductor, electron blocker, matrix, hole blocker and electron conductor consist of materials of the formula (III), of the formula (I) or an inventive crosslinked or polymerized material; only the emission layer additionally comprises at least one emitter.

In a preferred embodiment, the inventive OLED, in addition to layers (1) to (6), comprises at least one of the following layers mentioned below:
  a hole injection layer between the anode (1) and the hole-transporting layer (2);
  a blocking layer for electrons between the hole-transporting layer (2) and the light-emitting layer (3);
  an electron injection layer between the electron-transporting layer (5) and the cathode (6).

Materials for a hole injection layer may be selected from copper phthalocyanine, 4,4',4''-tris(N-3-methylphenyl-N-phenylamino)triphenylamine (m-MTDATA), 4,4',4''-tris(N-(2-naphthyl)-N-phenylamino)triphenylamine (2T-NATA), 4,4',4''-tris(N-(1-naphthyl)-N-phenylamino)triphenylamine (1T-NATA), 4,4',4''-tris(N,N-diphenylamino)triphenylamine (NATA), titanium oxide phthalocyanine, 2,3,5,6-tetrafluoro-7,7,8,8-tetracyanoquinodimethane (F4-TCNQ), pyrazino[2,3-f][1,10]phenanthroline-2,3-dicarbonitrile (PPDN), N,N,N',N'-tetrakis(4-methoxyphenyl)benzidine (MeO-TPD), 2,7-bis[N,N-bis(4-methoxy-phenyl)amino]-9,9-spirobifluorene (MeO-spiro-TPD), 2,2'-bis[N,N-bis(4-methoxy-phenyl)amino]-9,9-spirobifluorene (2,2'-MeO-spiro-TPD), N,N'-diphenyl-N,N'-di-[4-(N,N-ditolylamino)phenyl]benzidine (NTNPB), N,N'-diphenyl-N,N'-di-[4-(N,N-diphenylamino) phenyl]benzidine (NPNPB), N,N'-di(naphthalen-2-yl)-N,N'-diphenylbenzene-1,4-diamine (β-NPP). In principle, it is possible that the hole injection layer comprises at least one compound of the formula (III) as hole injection material.

The material selected for the electron injection layer may, for example, be LiF, CsF or $Cs_2CO_3$. In principle, it is possible that the electron injection layer comprises at least one compound of the formula (III), at least one compound of the general formula (I) or an inventive crosslinked or polymerized material as electron injection material.

Those skilled in the art are aware of how suitable materials have to be selected (for example on the basis of electrochemical studies). Suitable materials for the individual layers are known to those skilled in the art and are disclosed, for example, in WO 00/70655.

In addition, it is possible that some of the layers used in the inventive OLED have been surface-treated in order to increase the efficiency of charge carrier transport. The selection of the materials for each of the layers mentioned is preferably determined by obtaining an OLED with a high efficiency and lifetime.

The inventive OLED can be produced by methods known to those skilled in the art. In general, the inventive OLED is produced by successive vapor deposition of the individual layers onto a suitable substrate. Suitable substrates are, for example, glass, inorganic semiconductors or polymer films. For vapor deposition, it is possible to use customary techniques, such as thermal evaporation, chemical vapor deposition (CVD), physical vapor deposition (PVD) and others. In an alternative process, the organic layers of the OLED can be applied from solutions or dispersions in suitable solvents, employing coating techniques known to those skilled in the art.

In general, the different layers have the following thicknesses: anode (1) 50 to 500 nm, preferably 100 to 200 nm; hole-conducting layer (2) 5 to 100 nm, preferably 20 to 80 nm, light-emitting layer (3) 1 to 100 nm, preferably 10 to 80 nm, blocking layer for holes/excitons (4) 2 to 100 nm, preferably 5 to 50 nm, electron-conducting layer (5) 5 to 100 nm, preferably 20 to 80 nm, cathode (6) 20 to 1000 nm, preferably 30 to 500 nm. The relative position of the recombination zone of holes and electrons in the inventive OLED in relation to the cathode and hence the emission spectrum of the OLED can be influenced, among other factors, by the relative thickness of each layer. This means that the thickness of the electron transport layer should preferably be selected such that the position of the recombination zone is matched to the optical resonator property of the diode and hence to the emission wavelength of the emitter. The ratio of the layer thicknesses of the individual layers in the OLED depends on the materials used. The layer thicknesses of any additional layers used are known to those skilled in the art. It is possible that the electron-conducting layer and/or the hole-conducting layer has/have greater thicknesses than the layer thicknesses specified when they are electrically doped.

By virtue of use of the compounds of the formula (III), of the compounds of the general formula (I) or an inventive crosslinked or polymerized material in at least one layer of the OLED, preferably in the light-emitting layer (preferably as matrix material) and/or in the blocking layer for holes/excitons and/or preferably in the electron conductor layer, OLEDs with high efficiency and with low use voltage and operating voltage are obtained. Frequently, the OLEDs obtained by the use of the compounds of the formula (III) additionally have high lifetimes. The efficiency of the OLEDs can additionally be improved by optimizing the other layers of the OLEDs. For example, high-efficiency cathodes such as Ca or Ba, optionally in combination with an intermediate layer of LiF, CsF or $Cs_2CO_3$ can be used. Shaped substrates and novel hole-transporting materials which bring about a reduction in the operating voltage or an increase in the quantum efficiency are likewise usable in the inventive OLEDs. Moreover, additional layers may be present in the OLEDs in order to adjust the energy level of the different layers and to facilitate electroluminescence.

The OLEDs may further comprise at least one second light-emitting layer. The overall emission of the OLEDs may be composed of the emission of the at least two light-emitting layers and may also comprise white light.

The OLEDs can be used in all devices in which electroluminescence is useful. Suitable devices are preferably selected from stationary and mobile visual display units and illumination units. Stationary visual display units are, for example, visual display units of computers, televisions, visual display units in printers, kitchen appliances and advertising panels, illuminations and information panels. Mobile visual display units are, for example, visual display units in cellphones, laptops, digital cameras, MP3 players, vehicles and destination displays on buses and trains. Further devices in which the inventive OLEDs can be used are, for example, keyboards; items of clothing; furniture; wallpaper.

In addition, the compounds of the formula (III), compounds of the general formula (I) or an inventive crosslinked or polymerized material may be used in OLEDs with inverse structure. Preferably, the compounds of the formula (III) used in accordance with the invention, compounds of the general formula (I) or an inventive crosslinked or polymerized material are used in these inverse OLEDs, in turn, as hole/exciton blocker materials. The structure of inverse OLEDs and the materials typically used therein are known to those skilled in the art.

In addition, the present invention relates to a device selected from the group consisting of stationary visual display units such as visual display units of computers, televisions, visual display units in printers, kitchen appliances and advertising panels, illuminations, information panels, and mobile visual display units such as visual display units in cellphones, laptops, digital cameras, MP3 players, vehicles and destination displays on buses and trains; illumination units; keyboards; items of clothing; furniture; wallpaper, comprising at least one inventive organic light-emitting diode or at least one inventive light-emitting layer or at least one inventive electron-conducting layer.

EXAMPLES

Compound (I)

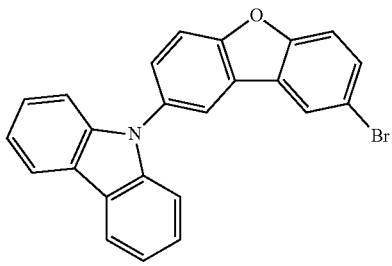

(1)

effected as in application PCT/EP2009/067120, which was yet to be published at the priority date of the present application.

Synthesis Example 1

Synthesis of 2-carbazolyl-8-imidazol-1-yldibenzofuran (Compound 2)

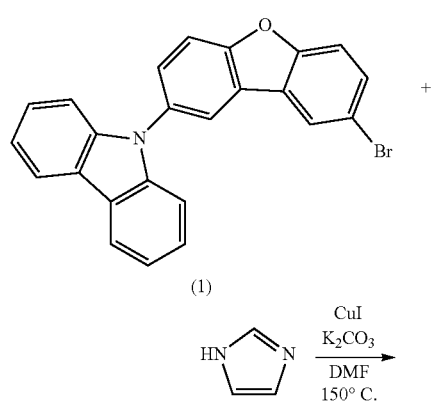

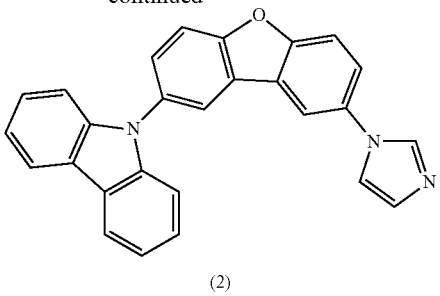

(2)

Under argon, compound 1 (5.0 g, 1 eq.) is combined with imidazole (1.03 g, 1.25 eq.), potassium carbonate (2.18 g, 1.3 eq.) and copper iodide (0.46 g, 0.2 eq.) in DMF (25 mL). The reaction is degassed with argon and heated to 150° C. The reaction is stirred at 150° C. for 48 h. The mixture is cooled to room temperature, and methylene chloride (600 mL) and demineralized water (300 mL) are added. After extractive stirring on a magnetic stirrer, the organic phase is removed and washed 3× with demineralized water (200 mL), then dried with sodium sulfate and concentrated. The white residue is suspended in cyclohexane, filtered off with suction and washed with ethanol. After drying under reduced pressure overnight, 4.65 g were obtained (95.9% yield).

$^1$H NMR (CD$_2$Cl$_2$, 400 MHz): δ=8.33 (s+d, 3H), 8.14 (s, 1H), 8.04 (s, 1H), 8.01 (d, 1H), 7.91 (d, 1H), 7.86 (d, 1H), 7.74 (d, 1H), 7.53-7.61 (m, 5H), 7.46 (dd, 2H), 7.33 (s, 1H).

Synthesis Example 2

Synthesis of 2-carbazolyl-8-(2-phenylimidazol-1-yl)) dibenzofuran (compound 3)

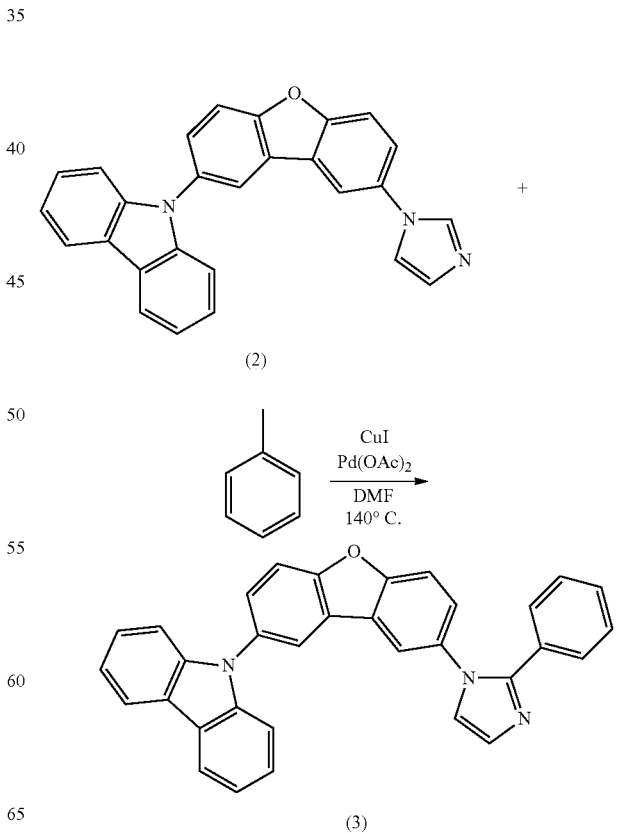

Under argon, compound 2 (2.0 g, 1 eq.) is combined with palladium acetate (56 mg, 0.05 eq.), copper iodide (1.93 g, 2.0 eq.) and iodobenzene (2.08 g, 2.0 eq.) in DMF (30 mL). The reaction is degassed with argon and heated to 140° C. The reaction is stirred at 140° C. for 24 h. The mixture is cooled to room temperature and precipitated with demineralized water, filtered with suction and washed with demineralized water. Dried under reduced pressure overnight. The solid is dissolved in methylene chloride and repeatedly extracted by shaking with a 10% sodium thiosulfate solution. Organic phase is washed with water, removed and concentrated. LC (C18-SiO$_2$; acetonitrile) gives 1.41 g of compound 3 (yield: 59.2%).

$^1$H NMR (CD$_2$Cl$_2$, 400 MHz): δ=8.17 (d, 2H), 8.09 (s, 1H), 7.89 (s, 1H), 7.85 (d, 1H), 7.70 (d, 1H), 7.66 (d, 1H), 7.20-7.43 (m, 14H)

Synthesis Example 3

Synthesis of N-(3-bromophenyl)carbazole (compound 4)

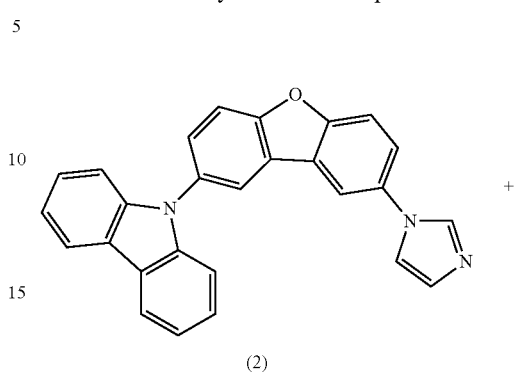

Under nitrogen, carbazole (24.3 g, 1 eq.) is added to a flask together with 1-bromo-3-iodobenzene (98%; 75.3 g, 1.9 eq.), potassium carbonate (48.2 g, 2.5 eq.) and copper (1.77 g, 0.1 eq.). The reaction is heated to 150° C. and stirred at 150° C. for 48 h. The mixture is cooled to room temperature and diluted with 150 mL of methylene chloride. 100 mL of demineralized water are added to the mixture, which is stirred. Removal of the aqueous phase is followed by washing a further 2× with demineralized water (100 mL). The organic phase is dried over sodium sulfate and concentrated. The excess 1-bromo-3-iodobenzene is distilled off under reduced pressure. LC (SiO$_2$; cyclohexane/methylene chloride 95:5) gives 37.1 g of product (82.4% yield).

$^1$H NMR (CD$_2$Cl$_2$, 400 MHz): δ=8.13 (d, 2H), 7.75 (s, 1H), 7.61 (d, 1H), 7.53 (d, 1H), 7.49 (d, 1H), 7.42 (m, 4H), 7.27-7.31 (m, 2H)

Synthesis Example 4

Synthesis of Compound 5

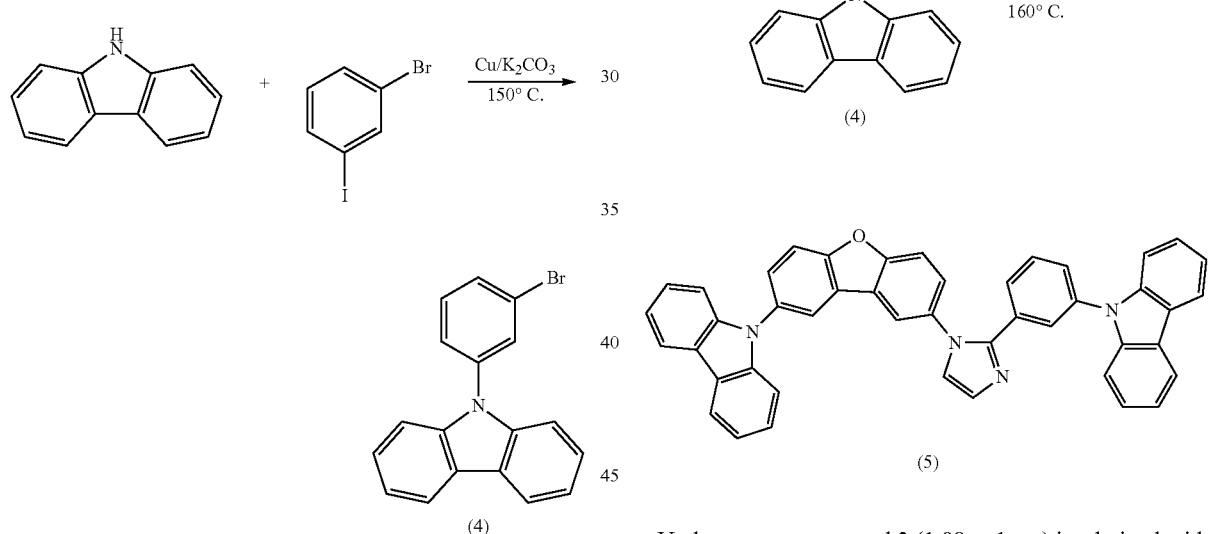

Under argon, compound 2 (1.08 g, 1 eq.) is admixed with palladium acetate (30 mg, 0.05 eq.), copper iodide (1.04 g, 2.0 eq.) and compound 4 (1.74 g, 2.0 eq.) in DMA (16 mL). The reaction is degassed with argon and heated to 160° C. The reaction is stirred at 160° C. for 20 h. The mixture is cooled to room temperature and diluted with 100 mL of methylene chloride. The brown solution is extracted by stirring in a beaker with 60 mL of a 10% sodium thiosulfate solution. The mixture is separated in a separating funnel; the organic phase is washed with water (3×100 mL). The organic phase is dried over sodium sulfate and concentrated. The tacky residue is extracted by stirring with ethanol, filtered off with suction and washed with a little ethanol. LC (SiO$_2$; methylene chloride) gives 1.53 g of compound 5 (88.4% yield).

$^1$H NMR (CD$_2$Cl$_2$, 400 MHz): δ=8.10 (d, 2H), 8.04 (s, 1H), 7.98 (d, 2H), 7.89 (s, 1H), 7.86 (d, 1H), 7.70 (m, 3H), 7.52 (dd, 1H), 7.38-7.44 (m, 3H), 7.28-7.35 (m, 4H), 7.22-7.25 (m, 3H), 7.10 (dd, 2H), 6.97 (dd, 2H), 6.91 (d, 1H)

Synthesis Example 5

Synthesis of 2-carbazolyl-8-benzimidazol-1-yldibenzofuran (Compound 6)

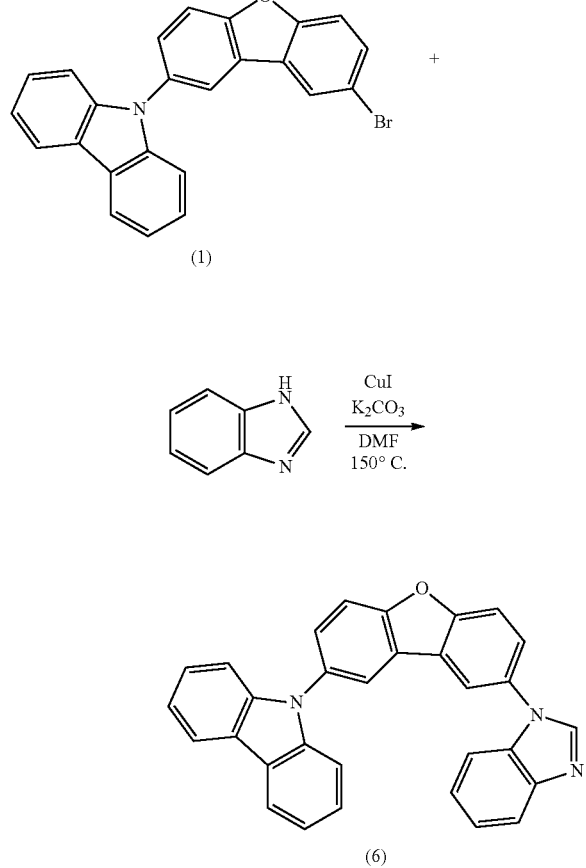

Under argon, compound 1 (4.36 g, 1 eq.) is combined with benzimidazole (1.60 g, 1.25 eq.), potassium carbonate (1.91 g, 1.3 eq.) and copper iodide (0.40 g, 0.2 eq.) in DMF (45 mL). The reaction is degassed with argon and heated to 150° C. The reaction is stirred at 150° C. for 48 h. Then copper iodide (0.40 g, 0.2 eq.) and potassium carbonate (1.91 g, 1.3 eq.) are added to the reaction. The mixture is stirred at 150° C. for a further 144 h. The experiment is cooled to room temperature and extracted by stirring with ethyl acetate and filtered with suction, and the residue is washed with ethyl acetate. The filtrate is concentrated and dried under reduced pressure overnight. LC (SiO$_2$, cyclohexane/ethyl acetate) gives 4.0 g of compound 6 (84% yield).

$^1$H NMR (CD$_2$Cl$_2$, 400 MHz): δ=8.18 (m, 4H), 8.11 (s, 1H), 7.82-7.90 (m, 3H), 7.73 (d, 1H), 7.69 (d, 1H), 7.58 (m, 1H), 7.40-7.45 (m, 4H), 7.29-7.36 (m, 4H).

Synthesis Example 6

Synthesis of 2-carbazolyl-8-(2-phenylbenzimidazol-1-yl)dibenzofuran (Compound 7)

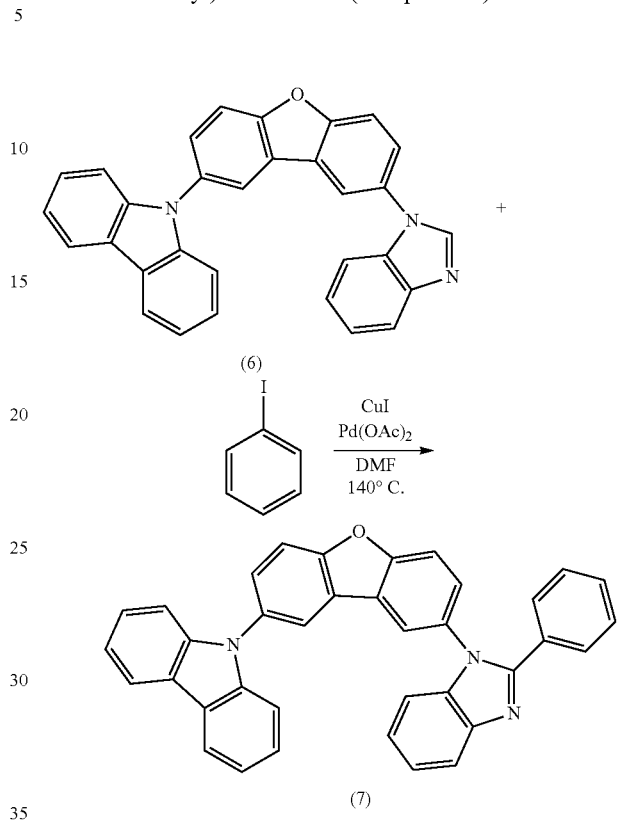

Under argon, compound 6 (2.25 g, 1 eq.) is combined with palladium acetate (56 mg, 0.05 eq.), copper iodide (1.93 g, 2.0 eq.) and iodobenzene (2.08 g, 2.0 eq.) in DMF (30 mL). The reaction is degassed with argon and heated to 140° C. The mixture is stirred at 140° C. for 24 h. After cooling to room temperature, add ethyl acetate (300 mL). Filter the suspension through silica gel. Wash with ethyl acetate (about 2 L) until product can longer be seen by TLC. The solution is concentrated, the residue obtained extracted by stirring in ethyl acetate (200 mL). The suspension is filtered (RS1). The filtrate is concentrated to 20 mL and filtered with suction (RS2), washed with a little ethyl acetate. LC (SiO$_2$, 9:1 cyclohexane/ethyl acetate) gives 1.43 g of product (54.3% yield).

$^1$H NMR (CD$_2$Cl$_2$, 400 MHz): δ=8.17 (d, 2H), 8.15 (s, 1H), 8.00 (s, 1H), 7.89 (d, 1H), 7.83 (d, 1H), 7.78 (d, 1H), 7.71 (d, 1H), 7.61 (d, 2H), 7.26-7.41 (m, 13H)

DIODE EXAMPLES

Comparative Example 1

Production of an OLED Comprising BCP as Electron Transport Material

The ITO substrate used as the anode is first cleaned with commercial detergents for LCD production (Deconex® 20NS and 25ORGAN-ACID® neutralizing agent) and then in an acetone/isopropanol mixture in an ultrasound bath. To eliminate possible organic residues, the substrate is exposed to a continuous ozone flow in an ozone oven for a further 25 minutes. This treatment also improves the hole injection properties of the ITO. Next, the AJ20-1000 hole injection layer from Plexcore is spun on from solution (~40 nm).

Thereafter, the organic materials specified below are applied to the cleaned substrate by vapor deposition at a rate of approx. 0.5-5 nm/min at about $10^{-8}$ mbar. The hole conductor and exciton blocker applied to the substrate is Ir(dpbic)$_3$ (V1) with a thickness of 45 nm, the first 35 nm of which are doped with MoO$_x$ (~10%) to improve the conductivity.

Emitter 2

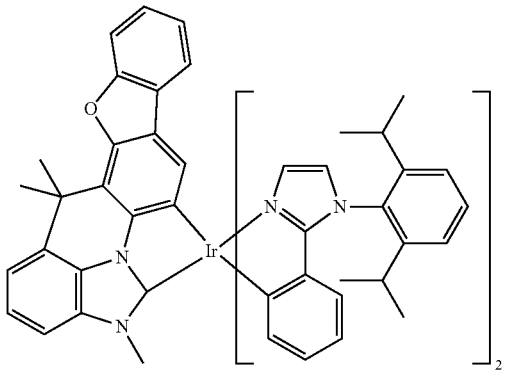

The compound Emitter 2 and the preparation process therefor are disclosed in European application EP 10160188.8, which was yet to be published at the priority date of the present application.

Subsequently, a mixture of 20% by weight of the compound (Emitter 2) and 80% by weight of the compound H1 (described in PCT application PCT/EP2009/067120, published as WO2010/079051) was applied by vapor deposition in a thickness of 40 nm, the former compound functioning as an emitter material, the latter as a matrix material.

Subsequently, the material H1 is applied by vapor deposition with a thickness of 10 nm as an exciton and hole blocker.

H1

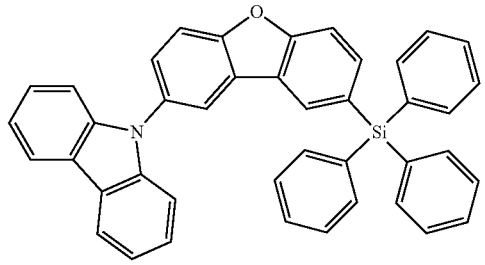

Next, as an electron transporter, a mixture of H1 (20%) and BCP (2,9-dimethyl-4,7-diphenyl-1,10-phenanthroline, 80%)) in a thickness of 20 nm, a 0.7 nm-thick LiF layer and finally a 100 nm-thick Al electrode were applied by vapor deposition. All components were bonded to a glass cover in an inert nitrogen atmosphere.

To characterize the OLED, electroluminescence spectra are recorded at different currents and voltages. In addition, the current-voltage characteristic is measured in combination with the emitted light output. The light output can be converted to photometric parameters by calibration with a photometer.

Example 1

Production of an OLED Comprising Compound 3 as Electron Transport Material

As comparative example 1, except that the electron transport material used is compound 3 according to synthesis example 2 instead of a mixture of BCP and H1. The measurements for comparative example 1 are set to 100%.

| Example | Current efficiency at 1000 cd/m$^2$ (Cd/A) | lm/W at 1000 cd/m$^2$ (%) | Voltage at 300 cd/m$^2$ (V) | External quantum efficiency (%) |
|---|---|---|---|---|
| Comparative example 1 | 100 | 100 | 100 | 100 |
| 1 | 116 | 177 | 66 | 114 |

Example 2

Production of an OLED Comprising Compound 3 as Host, Exciton Blocker and Electron Transport Material As comparative example 1, except that the host used is compound 3 according to synthesis example 2 instead of H1, the hole/exciton blocker used is compound 3 (5 nm) instead of H1 and the electron transport material used is compound 3 according to synthesis example 2 instead of a mixture of BCP and H1. The measurements for comparative example 1 are set to 100%.

| Example | Current efficiency at 1000 cd/m$^2$ (Cd/A) | lm/W at 1000 cd/m$^2$ (%) | Voltage at 300 cd/m$^2$ (V) | External quantum efficiency (%) |
|---|---|---|---|---|
| Comparative example 1 | 100 | 100 | 100 | 100 |
| 2 | 135 | 184 | 73 | 128 |

Example 3

Production of an OLED Comprising Compound 3 or 7 as Electron Transport Material

Device built-up as comparative example 1, with the following differences:

The electron transport material used is compound 3 according to synthesis example 2 (example 3a and 3c) respectively compound 7 according to synthesis example 6 (example 3b).

As a host H2 (example 3a), H3 (example 3b) and H4 (example 3c) is used.

The emitter layer (16 nm) comprises a mixture of Ir(dpbic)$_3$ (VI) (40 wt.-%), emitter 3 (described in the not prior published European patent application EP 10 187 176.2 and the not prior published U.S. application U.S. 61/391,712) (30 wt.-%) and a host (H2, H3 or H4) (30 wt.-%).

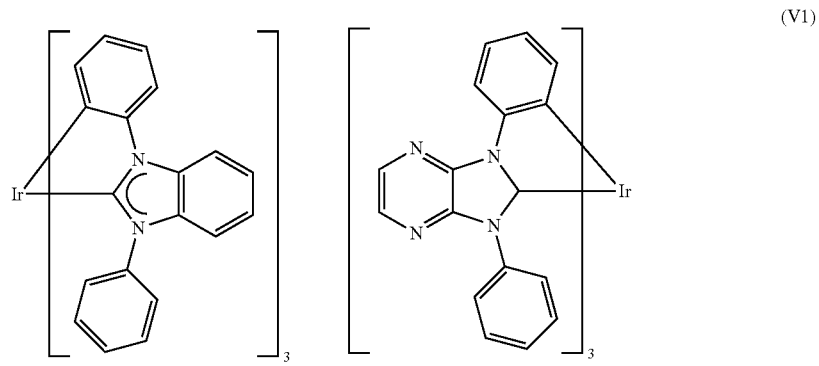

emitter 3

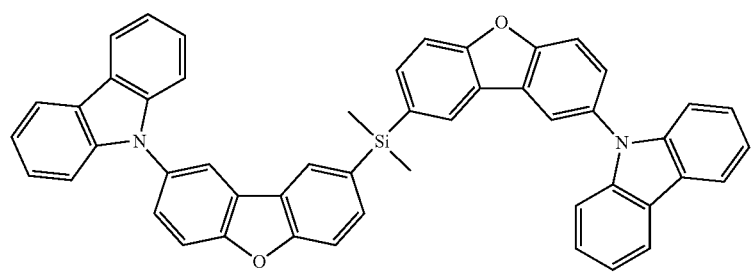

H2

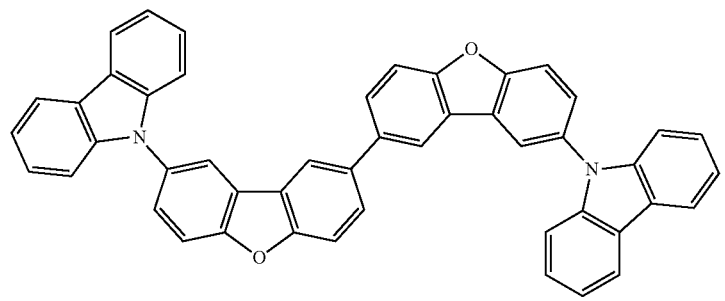

H3

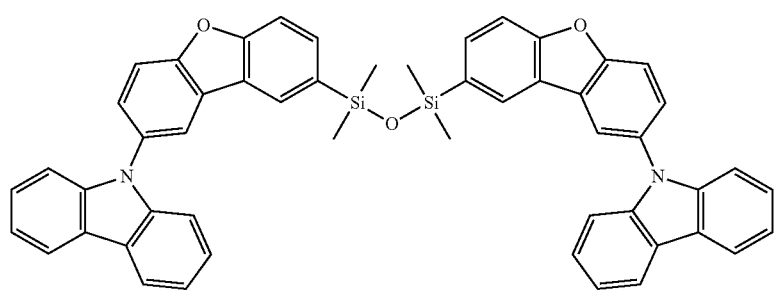

H4

As hole blocker 10 nm of the respective host are used. As electron transporter 20 nm of compound 3 (examples 3a and 3c) respectively 7 (example 3b) are used.

The measurements for comparative example 1 are set to 100%.

| Example | Host | ETL[1] | Current efficiency at 1000 cd/m² (Cd/A) | lm/W at 1000 cd/m² (%) | Voltage at 300 cd/m² (V) | External quantum efficiency (%) |
|---|---|---|---|---|---|---|
| comparative example 1 | H1 | BCP | 100 | 100 | 100 | 100 |
| 3a | H2 | compound 3 | 154 | 208 | 69 | 149 |
| 3b | H3 | compound 7 | 161 | 188 | 80 | 152 |

| Example | Host | ETL[1] | Current efficiency at 1000 cd/m² (Cd/A) | lm/W at 1000 cd/m² (%) | Voltage at 300 cd/m² (V) | External quantum efficiency (%) |
|---|---|---|---|---|---|---|
| 3c | H4 | compound 3 | 188 | 232 | 73 | 186 |

[1]ETL = electron transport layer

Example 4

Production of an OLED Comprising Compound 3 as Electron Transport Material

Device built-up as example 3a, with the following differences:

The emitter layer (20 nm) comprises a mixture of emitter (20 wt.-%), emitter 3 (example 4a), emitter 4 (example 4b), emitter 5 (example 4c) (emitter 3, 4 and 5 are described in the not prior published European patent application EP 10 187 176.2 and the not prior published U.S. application 61/391,712) and a host (H3) (80 wt.-%).

As hole blocker 5 nm of H3 are used. As electron transporter 20 nm of compound 3 are used. As electron injection layer CsF (2 nm) are used. The hole transport layer (10 nm) is doped with 10 wt.-% $MO_x$.

| Example | emitter | Current efficiency at 1000 cd/m² (Cd/A) | lm/W at 1000 cd/m² (%) | Voltage at 300 cd/m² (V) | Current efficiency at 1000 cd/m² (Cd/A) |
|---|---|---|---|---|---|
| 4a | emitter 3 | 100 | 100 | 100 | 100 |
| 4b | emitter 4 | 147 | 122 | 116 | 150 |
| 4c | emitter 5 | 128 | 131 | 98 | 127 |

The measurements for example 4a are set to 100% for comparison.

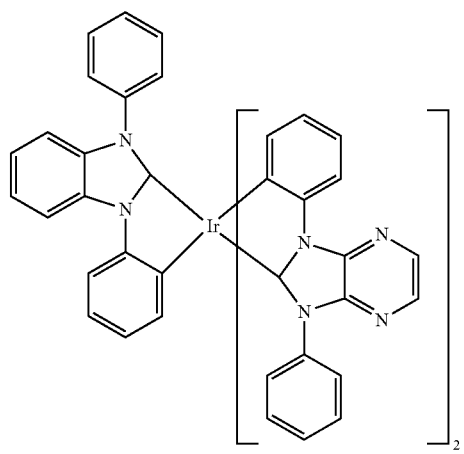

emitter 4

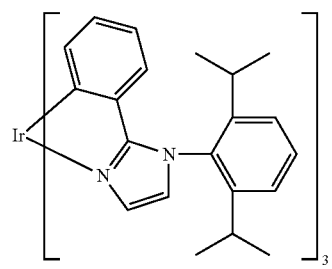

emitter 5

The invention claimed is:

1. An organic light-emitting diode, comprising:
at least one compound of formula (I):

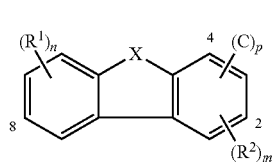

(I)

wherein

X is S or O;

$R^1$ and $R^2$ are each independently aryl, heteroaryl, alkyl, cycloalkyl, heterocycloalkyl, a crosslinkable or polymerizable group bonded via a spacer, —$NR^3R^4$, —$P(O)R^5R^6$, —$PR^7R^8$, —$S(O)_2R^9$, —$S(O)R^{10}$, —$SR^{11}$ or —$OR^{12}$, or a C group;

$R^3$, $R^4$ are each independently aryl, heteroaryl, alkyl, cycloalkyl or heterocycloalkyl, a crosslinkable or polymerizable group bonded via a spacer, or $R^3$ and $R^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;

$R^5, R^6, R^7, R^8, R^9, R^{10}, R^{11}$ and $R^{12}$ are each independently aryl, heteroaryl, alkyl, cycloalkyl or heterocycloalkyl, a crosslinkable or polymerizable group bonded via a spacer, n is 0, 1, 2, 3 or 4, m is 0, 1, 2 or 3, p is 1 or 2, wherein m+p is ≤4, C is a five-membered saturated or unsaturated heterocyclic radical of formula (II)

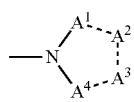

(II)

wherein
A¹ is independently CR$^a$, N or NR$^b$;
A² is independently CR$^c$, N or NR$^d$;
A³ is independently CR$^e$, N or NR$^f$;
A⁴ is independently CR$^g$, N or NR$^h$
R$^a$, R$^b$, R$^c$, R$^d$, R$^e$, R$^f$, R$^g$ and R$^h$ are each independently hydrogen, aryl, heteroaryl, alkyl, cycloalkyl, heterocycloalkyl, a crosslinkable or polymerizable group bonded via a spacer;
or
one combination of 2 R groups selected from the group consisting of
(R$^a$ or R$^b$) and (R$^c$ or R$^d$),
(R$^e$ or R$^f$) and (R$^g$ or R$^h$), and
(R$^c$ or R$^d$) and (R$^e$ or R$^f$)
may optionally form, together with the carbon or nitrogen atom, a cyclic radical which has 3 to 10 ring atoms and may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;
wherein the C group is bonded in the 2 and/or 4 position,
or
two units of the general formula (I) are bridged to one another via a bond, a linear or branched, saturated or unsaturated bridge optionally interrupted by at least one heteroatom or via O, wherein this bridge in the general formula (I) is bonded in place of R$^a$, R$^b$, R$^c$, R$^d$, R$^e$, R$^f$, R$^g$, R$^h$ or via and/or in place of R¹ or R², in monomeric, polymerized or crosslinked form.

2. The organic light-emitting diode according to claim 1, wherein R¹ is independently aryl selected from phenyl, naphthyl, anthracenyl, phenanthrenyl, indenyl and fluorenyl which each may be unsubstituted substituted at one, more than one or all substitutable positions, heteroaryl selected from pyridine radicals, pyrimidine radicals, pyrrole radicals, furan radicals, pyrazole radicals, imidazole radicals, thiophene radicals, oxazole radicals, thiazole radicals, triazole radicals, benzofuryl radicals, benzothienyl radicals, benzopyrrolyl radicals, dibenzofuryl radicals, phenanthrolinyl radicals, carbazolyl radicals, azacarbazolyl radicals and diazacarbazoyl radicals which may be unsubstituted or substituted at one, more than one or all substitutable positions, alkyl, cycloalkyl, heterocycloalkyl, a crosslinkable or polymerizable group bonded via a spacer, —NR³R⁴, —P(O)R⁵R⁶, —PR⁷R⁸, —S(O)₂R⁹, —S(O)R¹⁰, —SR¹¹ or —OR¹²;
R³ and R⁴ are each independently aryl, heteroaryl, alkyl, cycloalkyl or heterocycloalkyl,
a crosslinkable or polymerizable group bonded via a spacer, or R³ and R⁴ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be
fused to one or more further cyclic radicals having 3 to 10 ring atoms, wherein the fused
radicals may be unsubstituted or substituted by one or more substituents selected from
alkyl, cycloalkyl, heterocycloalkyl, aryl, heteroaryl, a crosslinkable or polymerizable group
bonded via a spacer, or a group with donor or acceptor action;
R⁵, R⁶, R⁷, R⁸, R⁹, R¹⁰, R¹¹ and R¹² are each independently aryl, heteroaryl, alkyl,
cycloalkyl or heterocycloalkyl, a crosslinkable or polymerizable group bonded via a spacer,
n is 0, 1, 2, 3 or 4,
m is 0, 1, 2 or 3,
p is 1 or 2, wherein m+p is ≤4,
C is a five-membered saturated or unsaturated heterocyclic radical of formula (II)

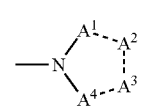

(II)

wherein
A¹ is independently CR$^a$, N or NR$^b$;
A² is independently CR$^c$, N or NR$^d$;
A³ is independently CR$^e$, N or NR$^f$;
A⁴ is independently CR$^g$, N or NR$^h$
R$^a$, R$^b$, R$^c$, R$^d$, R$^e$, R$^f$, R$^g$ and R$^h$ are each independently hydrogen, aryl, heteroaryl, alkyl, cycloalkyl, heterocycloalkyl, a crosslinkable or polymerizable group bonded via a spacer,
wherein the C group is bonded in the 2 and/or 4 position.

3. The organic light-emitting diode according to claim 1, wherein n is 1.

4. The organic light-emitting diode according to claim 1, wherein m is 0.

5. The organic light-emitting diode according to claim 1, wherein X is O.

6. The organic light-emitting diode according to claim 1, wherein
R¹ is —NR³R⁴; and
R³ and R⁴ form, together with the nitrogen atom, a cyclic radical which has 3 to 10 ring
atoms and may be unsubstituted or substituted by one or more substituents selected from
alkyl, cycloalkyl, heterocycloalkyl, aryl, heteroaryl and a group with donor or acceptor
action and/or may be fused to one or more further cyclic radicals having 3 to 10 ring
atoms, wherein the fused radicals may be unsubstituted or substituted by one or more
substituents selected from alkyl, cycloalkyl, heterocycloalkyl, aryl, heteroaryl, a crosslinkable or polymerizable group bonded via a spacer, or a group with donor or
acceptor action.

7. The organic light-emitting diode according to claim 1, wherein R¹ is selected from the group consisting of carbazolyl, pyrrolyl, indolyl, imidazolyl, triazolyl, benzimidazolyl, azacarbazolyl, diazacarbazolyl and diphenylamine, unsubstituted or substituted by one or more substituents selected from alkyl, cycloalkyl, heterocycloalkyl, aryl, heteroaryl, a crosslinkable or polymerizable group bonded via a spacer or a group with donor or acceptor action.

8. The organic light-emitting diode according to claim 1, wherein the C group is:

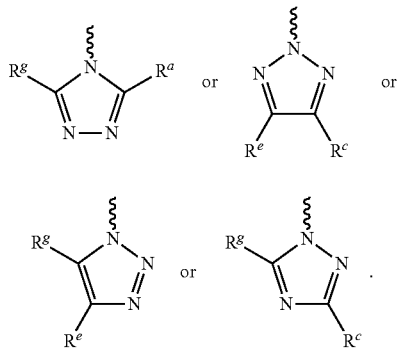

9. The organic light-emitting diode according to claim 8, wherein the C group is:

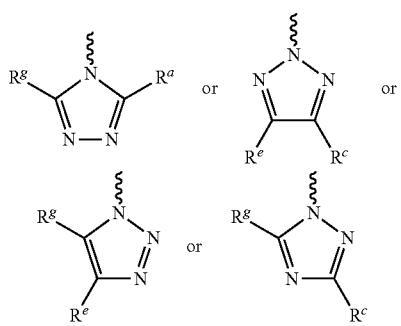

wherein
R$^a$ is not

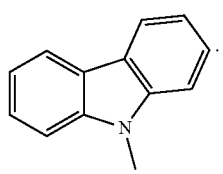

10. The organic light-emitting diode according to claim 1, wherein the C group is:

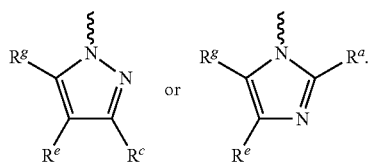

11. The organic light-emitting diode according to claim 10, wherein in the group

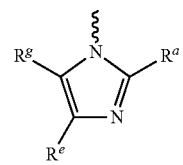

R$^g$, R$^e$ are H, and

R$^a$ is hydrogen, aryl, heteroaryl, alkyl, cycloalkyl, heterocycloalkyl, a crosslinkable or polymerizable group bonded via a spacer.

12. The organic light-emitting diode according to claim 1, wherein the C group is:

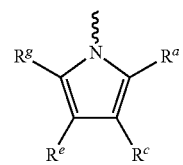

with the proviso that a compound of the following formula is excluded:

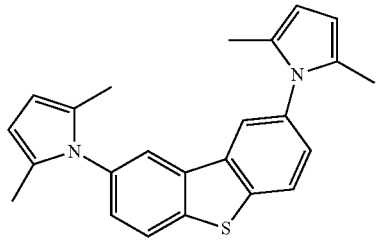

13. The organic light-emitting diode according to claim 1, wherein at least one of R$^a$, R$^c$, R$^e$ and R$^g$ is aryl.

14. The organic light-emitting diode according to claim 2, wherein

R$^1$ is —NR$^3$R$^4$, and

R$^3$ and R$^4$ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and n is 1.

15. The organic light-emitting diode according to claim 1, wherein the compound of the general formula (I) is selected from

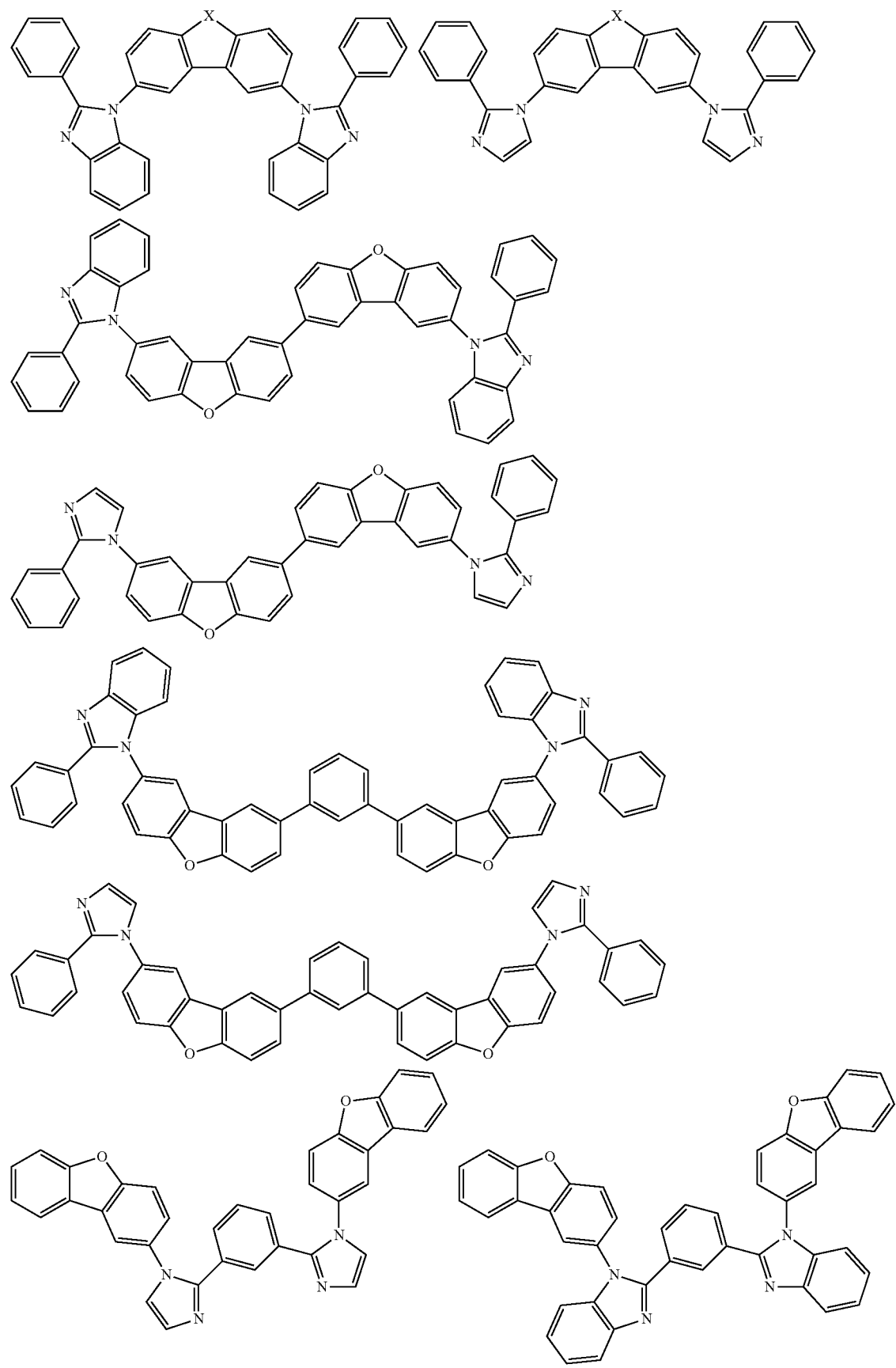

-continued
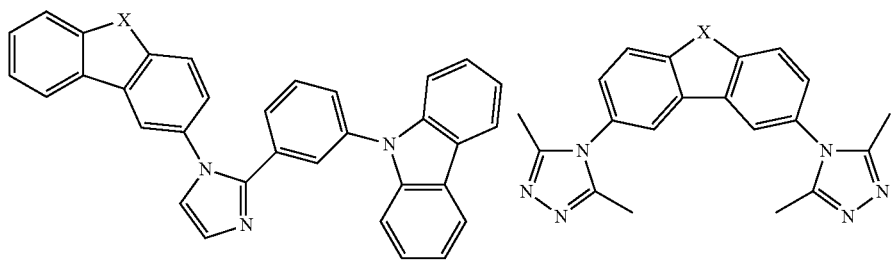
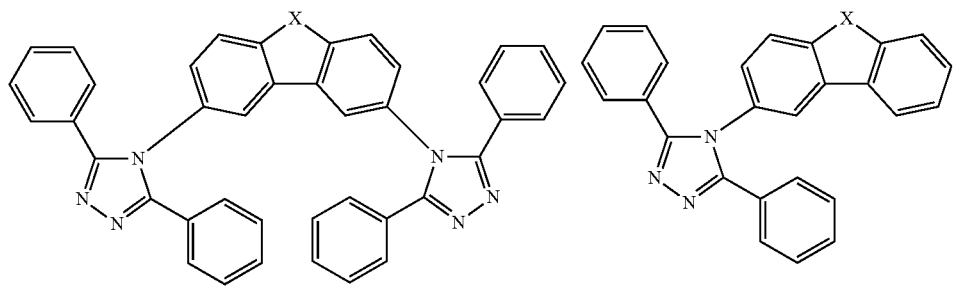
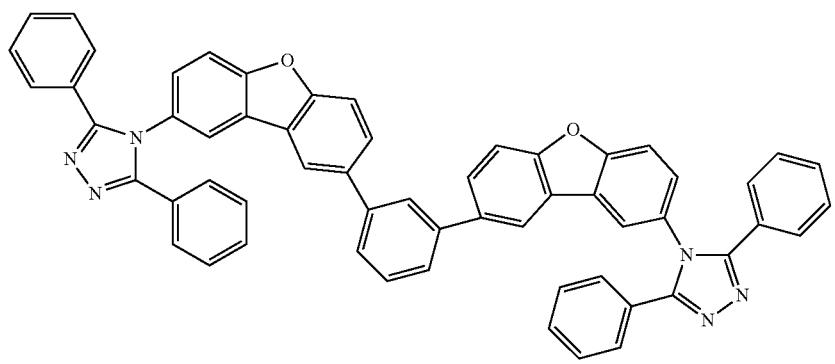
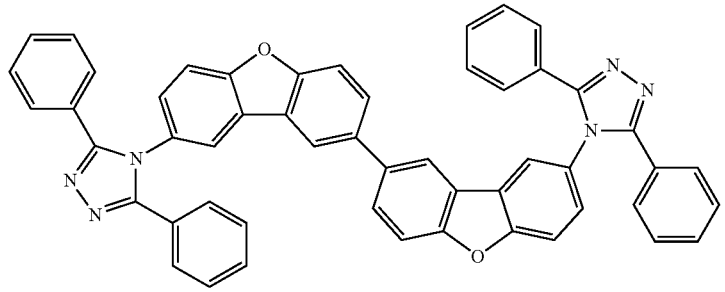
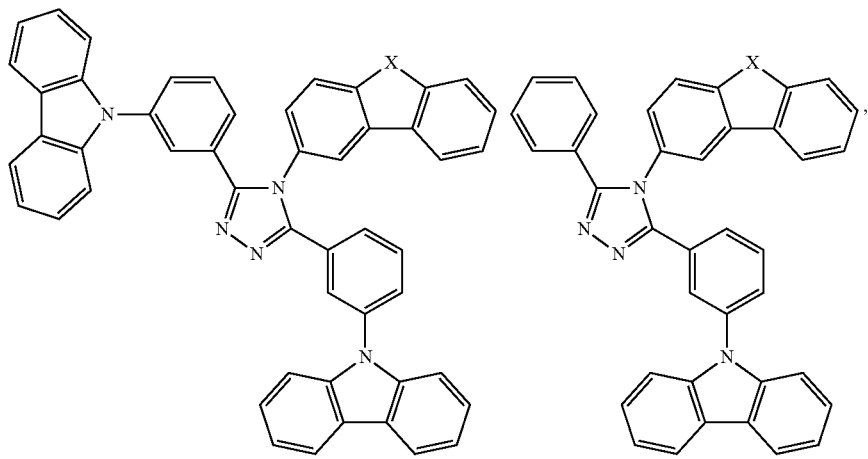

-continued
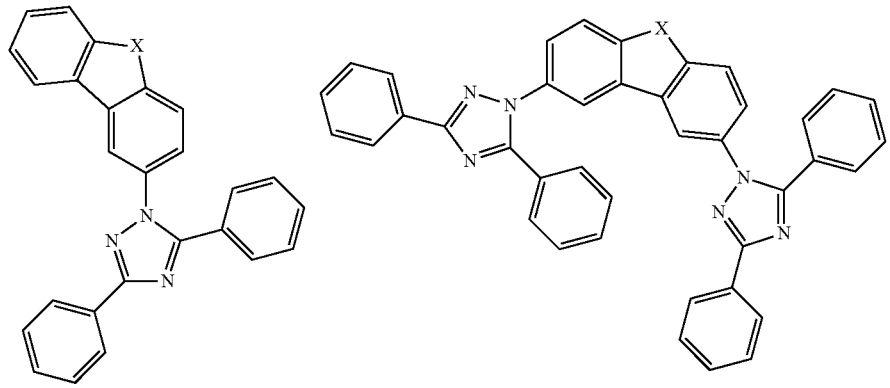
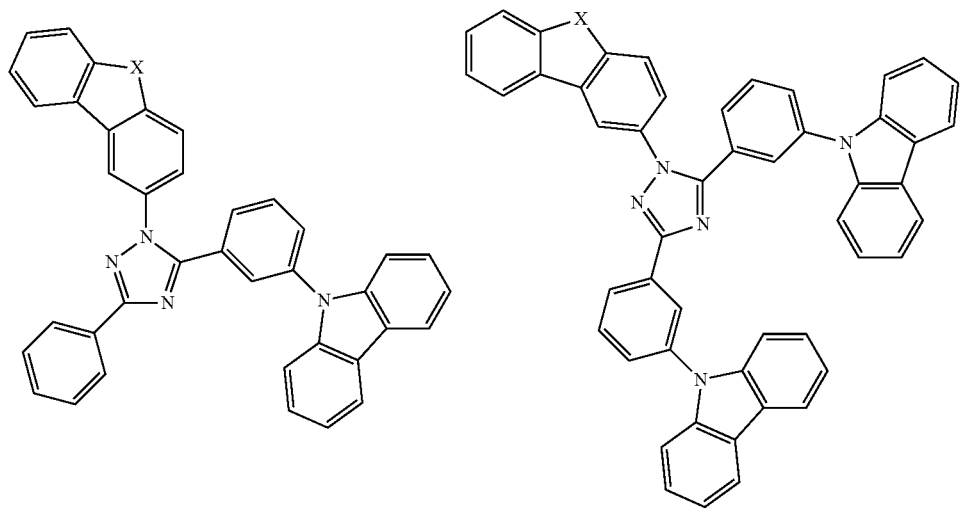
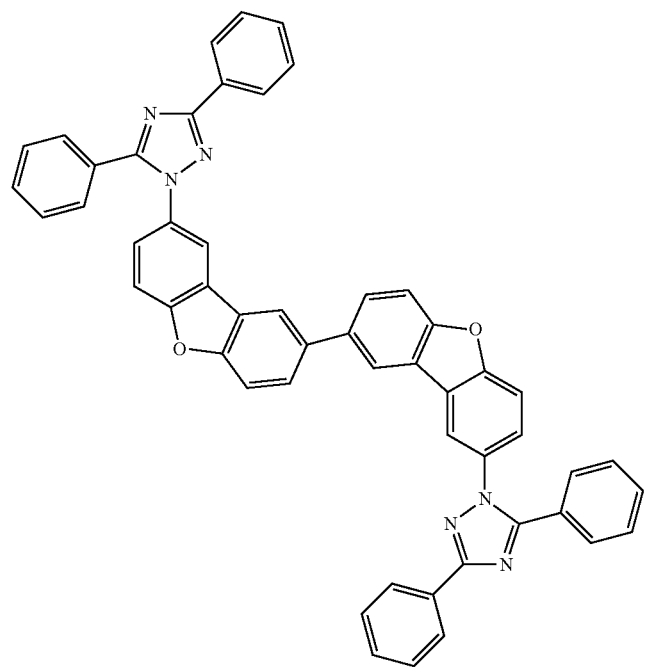

-continued
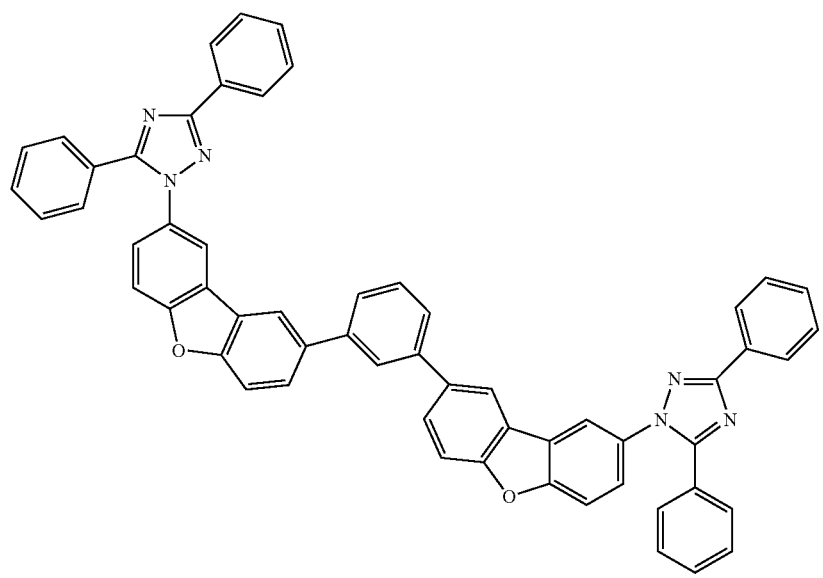
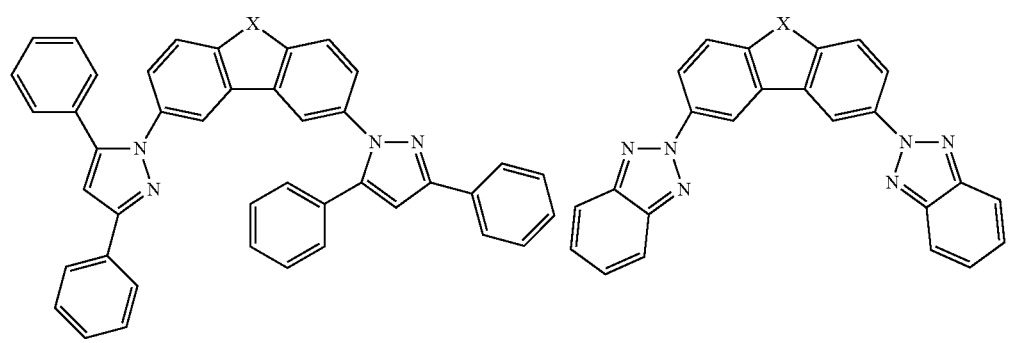
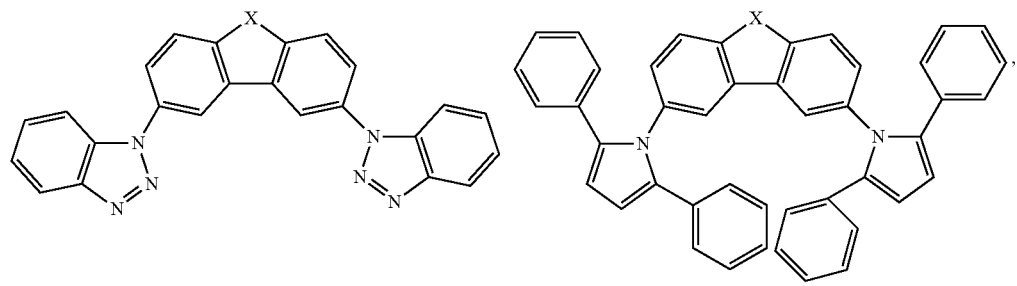
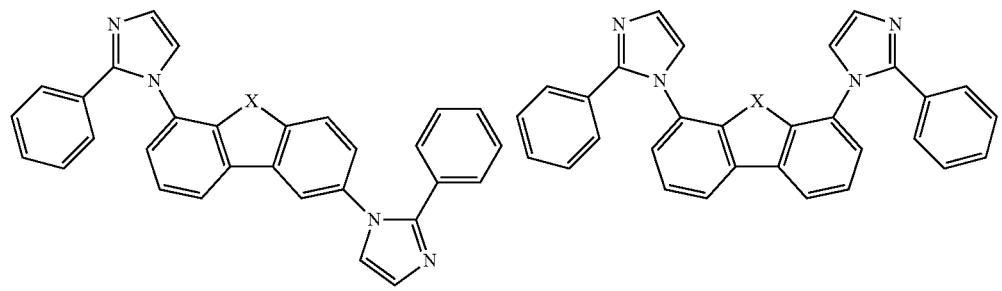

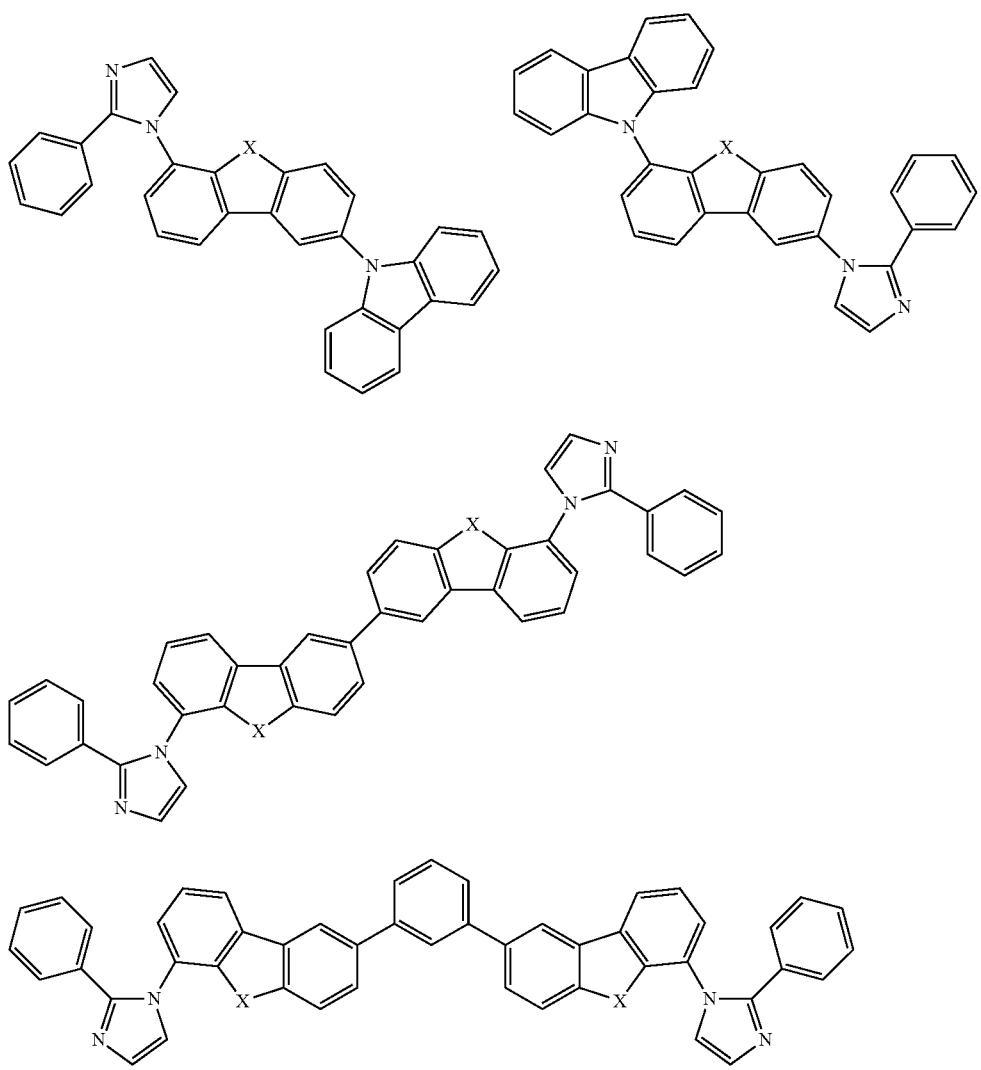

wherein X is S or O.

16. The organic light-emitting diode according to claim 1, comprising at least one compound of formula (I) as host, blocker and/or charge transport material.

17. A compound of formula (III)

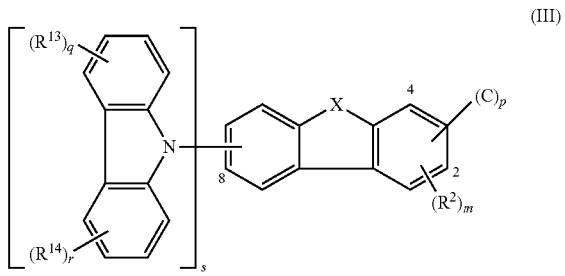

wherein
X is S or O;
R² are each independently aryl, heteroaryl, alkyl, cycloalkyl, heterocycloalkyl, a crosslinkable or polymerizable group bonded via a spacer, —NR³R⁴, —P(O)R⁵R⁶, —PR⁷R⁸, —S(O)₂R⁹, —S(O)R¹⁰, —SR¹¹ or —OR¹², R³, R⁴ are each independently aryl, heteroaryl, alkyl, cycloalkyl or heterocycloalkyl, a crosslinkable or polymerizable group bonded via a spacer, or R³ and R⁴ form, together with the nitrogen atom, a cyclic radical which has 3 to 10 ring atoms and may be unsubstituted or substituted by one or more substituents selected from alkyl, cycloalkyl, heterocycloalkyl, aryl, heteroaryl and a group with donor or acceptor action and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, a crosslinkable or polymerizable group bonded via a spacer, and a group with donor or acceptor action;

R⁵, R⁶, R⁷, R⁸, R⁹, R¹⁰, R¹¹ and R¹² are each independently aryl,
heteroaryl, alkyl, cycloalkyl or heterocycloalkyl, a crosslinkable or polymerizable group bonded via a spacer, $R^{13}$, $R^{14}$ are each independently aryl, heteroaryl, alkyl, cycloalkyl, heterocycloalkyl, a crosslinkable or polymerizable group bonded via a spacer, $-NR^3R^4$, $-P(O)R^5R^6$, $-PR^7R^8$, $-S(O)_2R^9$, $-S(O)R^{10}$, $-SR^{11}$ or $-OR^{12}$, m is 0, 1, 2 or 3, p is 1 or 2, wherein m+p is ≤4, q is 0, 1, 2, 3 or 4, r is 0, 1, 2, 3 or 4, s is 1, 2, 3 or 4, C is a five-membered saturated or unsaturated heterocyclic radical of formula (II)

$$—N\begin{matrix}A^1\cdots A^2\\ |\\ A^4\cdots A^3\end{matrix}$$ (II)

wherein $A^1$ is independently $CR^a$, N or $NR^b$;

$A^2$ is independently $CR^c$, N or $NR^d$;

$A^3$ is independently $CR^e$, N or $NR^f$;

$A^4$ is independently $CR^g$, N or $NR^h$;

$R^a$, $R^b$, $R^c$, $R^d$, $R^e$, $R^f$, $R^g$ and $R^h$ are each independently hydrogen, aryl, heteroaryl, alkyl, cycloalkyl, heterocycloalkyl, a crosslinkable or polymerizable group bonded via a spacer;

or one combination of 2R groups selected from the group consisting of ($R^a$ or $R^b$) and ($R^c$ or $R^d$), ($R^e$ or $R^f$) and ($R^g$ or $R^h$), and ($R^c$ or $R^d$) and ($R^e$ or $R^f$)

may optionally form, together with the carbon or nitrogen atom, a cyclic radical which has 3 to 10 ring atoms and may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action, and/or may be fused to one or more further cyclic radicals having 3 to 10 ring atoms, wherein the fused radicals may be unsubstituted or substituted by one or more substituents selected from alkyl, cycloalkyl, heterocycloalkyl, aryl, heteroaryl, a crosslinkable or polymerizable group bonded via a spacer, or a group with donor or acceptor action;

wherein the C group is bonded in the 2 and/or 4 position, or two units of the general formula (III) are bridged to one another via a bond, a linear or branched, saturated or unsaturated bridge optionally interrupted by at least one heteroatom or via O, wherein this bridge in the general formula (III) is bonded in place of $R^a$, $R^b$, $R^c$, $R^d$, $R^e$, $R^f$, $R^g$, $R^h$, $R^{13}$, $R^{14}$ or via and/or in place of $R^2$.

18. A compound according to claim 17, wherein $R^a$, $R^b$, $R^c$, $R^d$, $R^e$, $R^f$, $R^g$ and $R^h$ are each independently hydrogen, aryl, heteroaryl, alkyl, cycloalkyl, heterocycloalkyl, a crosslinkable or polymerizable group bonded via a spacer.

19. A compound according to claim 17, wherein s is 1;

p is 1; and m is 0.

20. A compound according to claim 17, wherein the C group is:

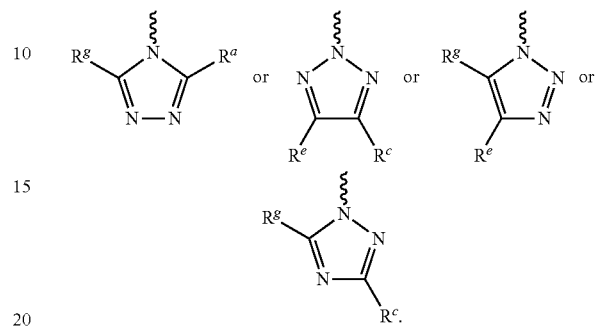

21. A compound according to claim 17, wherein the C group is:

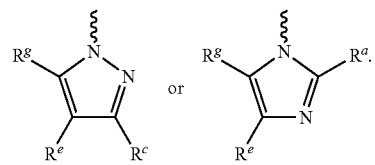

22. A compound according to claim 17, wherein the C group is

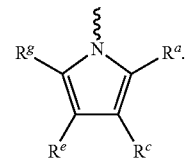

23. A compound according to claim 17, wherein a carbazolyl substituent (IV)

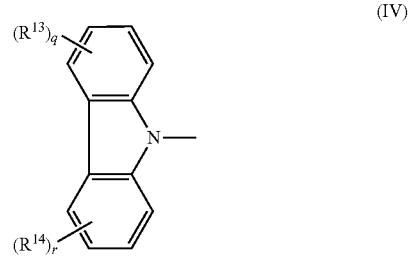

is present bonded in the 8 position of the dibenzofuran or dibenzothiophene base skeleton.

24. A compound according to claim 17, which is selected from the following group

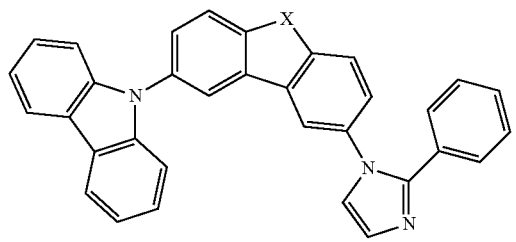
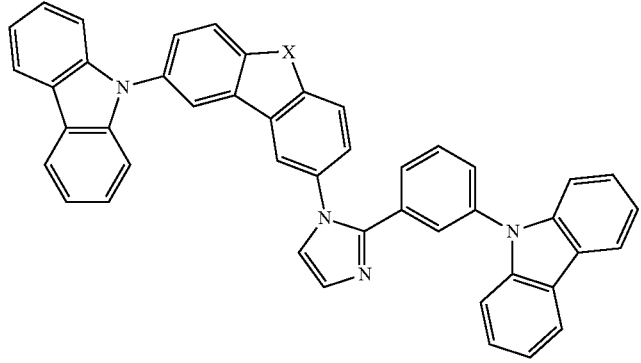
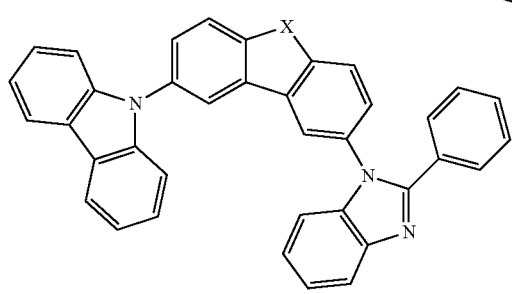
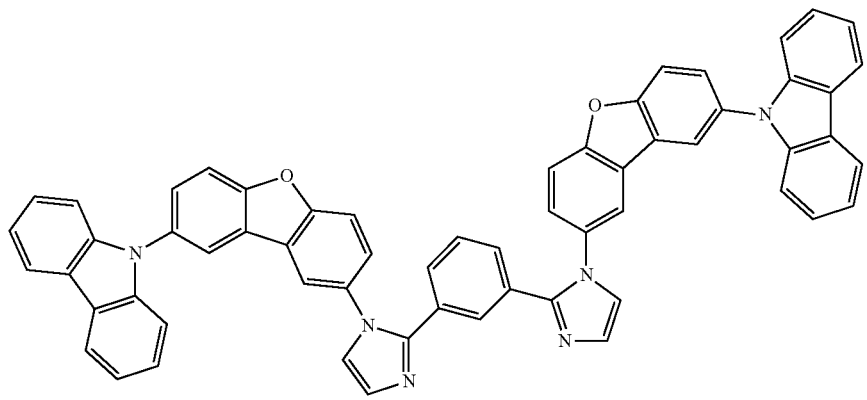
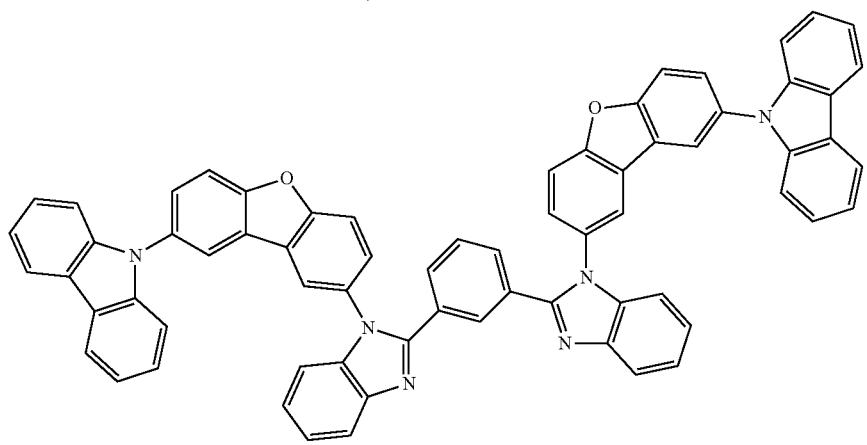

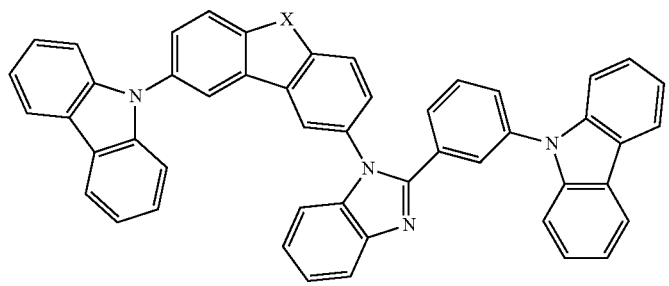
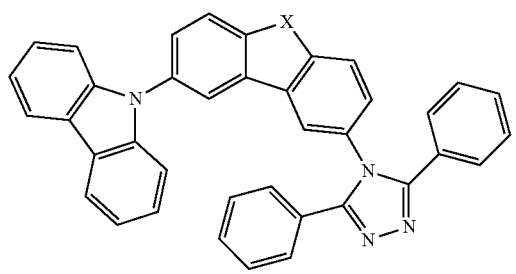
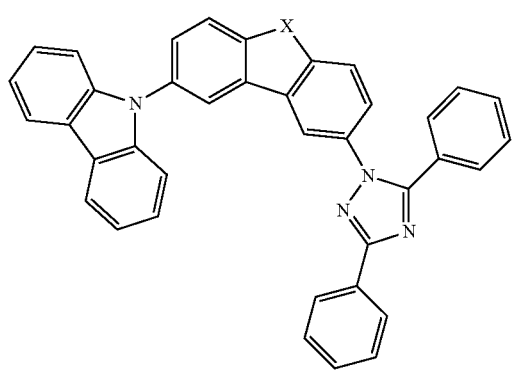
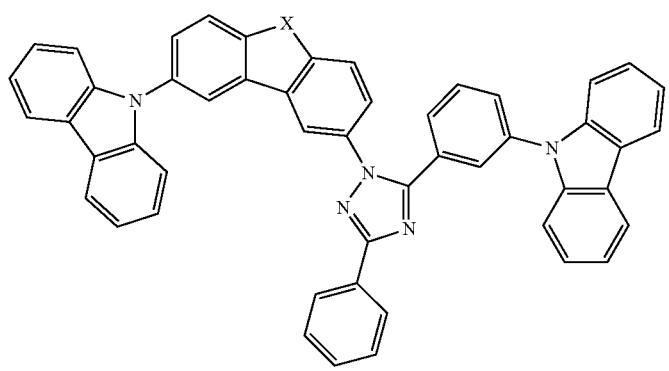

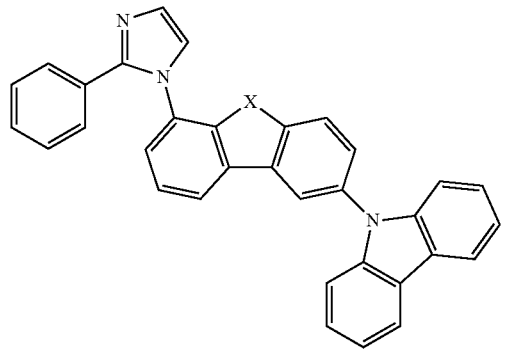
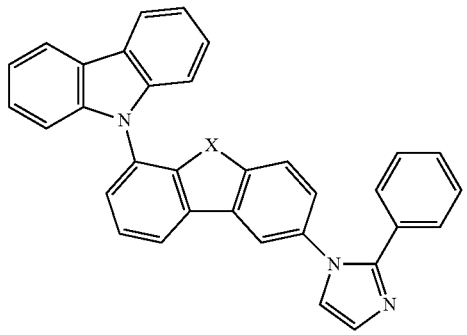

wherein X is S or O.

25. A process for preparing compounds of the formula (III) according to claim 17, wherein the at least one carbazolyl radical (IV)

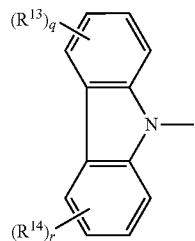
(IV)

and the optionally substituted five-membered nitrogen heterocycle C are introduced into a base skeleton of the formula (V) according to one of the following variants a) or b)

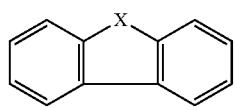
(V)

wherein X is S or O,
variant a)
ia) preparation of a precursor compound suitable for introduction of the carbazolyl radical(s) (IV), and optionally of the R² radical(s) and of the C radical(s),
iia) introduction of the carbazolyl radical(s) (IV),
iiia) introduction of the C radical(s) or of a precursor thereof, and, if present, introduction of the R² radical(s),
iva) optionally, conversion of the precursor of C to the C radical,
or
variant b)
ib) preparation of a precursor compound suitable for introduction of the carbazolyl radical(s) (IV), and optionally of the R² radical(s) and of the C radical(s),
iib) introduction of the C radical(s) or of a precursor thereof,
iiib) introduction of the carbazolyl radical(s) (IV), and, if present, introduction of the R² radical(s),
ivb) optionally, conversion of the precursor of C to the C radical.

26. A crosslinked or polymerized material which comprises units of the general formula (III) according to claim 17.

27. Formulations for liquid-processed applications in organic electronics a compound of the general formula (III) according to claim 17.

28. An organic light-emitting diode comprising at least one compound of the formula (III) according to claim 17.

29. The organic light-emitting diode according to claim 28, comprising an anode An and a cathode Ka and at least one light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (III) is present in the electron conductor layer and/or light-emitting layer E and/or in at least one of the further layers.

30. The organic light-emitting diode according to claim 28, wherein at least one compound of the formula (III) is present in the electron conductor layer and/or in the light-emitting layer and/or in the at least one blocking layer for holes/excitons.

31. A light-emitting layer comprising at least one compound of the formula (III) according to claim 17.

32. A blocking layer for holes/excitons, comprising at least one compound of the formula (III) according to claim 17.

33. An electron-conducting layer comprising at least one compound of the formula (III) according to claim 17.

34. A device selected from the group consisting of stationary visual display units, mobile visual display units, illumination units; keyboards; garments; furniture and wallpaper, comprising at least one organic light-emitting diode according to claim 1.

35. A crosslinked or polymerized material which comprises units of the general formula (I) as defined in claim 1.

36. Formulations for liquid-processed applications in organic electronics comprising a compound of the general formula (I) as defined in claim 1.

37. Formulations for liquid-processed applications in organic electronics comprising a material according to claim 26.

38. An organic light-emitting diode comprising a material according to claim 26.

39. The organic light-emitting diode according to claim 1 comprising an anode An and a cathode Ka and at least one light-emitting layer E arranged between the anode An and the cathode Ka, and optionally at least one further layer selected from the group consisting of at least one blocking layer for holes/excitons, at least one blocking layer for electrons/excitons, at least one hole injection layer, at least one hole conductor layer, at least one electron injection layer and at least one electron conductor layer, wherein the at least one compound of the formula (I) is present in the electron conductor layer and/or light-emitting layer E and/or in at least one of the further layers.

40. The organic light-emitting diode according to claim 39 wherein at least one compound of the formula (I) is present in the electron conductor layer and/or in the light-emitting layer and/or in the at least one blocking layer for holes/excitons.

41. The organic light-emitting diode according to claim 38 wherein the at least one compound of the formula (I) is present in the electron conductor layer and/or in the light-emitting layer and/or in the at least one blocking layer for holes/excitons.

42. A light-emitting layer comprising a compound of the general formula (I) as defined in claim 1.

43. A light-emitting layer comprising a material according to claim 26.

44. A blocking layer for holes/excitons comprising a compound of the general formula (I) as defined in claim 1.

45. A blocking layer for holes/excitons comprising a material according to claim 26.

46. An electron-conducting layer comprising a compound of the general formula (I) as defined in claim 1.

47. An electron-conducting layer comprising a material according to claim 26.

48. A device selected from the group consisting of stationary visual display units, mobile visual display units, illumination units, keyboards, garments, furniture and wallpaper, comprising at least one organic light-emitting diode according to claim 28.

49. A device selected from the group consisting of stationary visual display units, mobile visual display units, illumination units, keyboards, garments, furniture and wallpaper, comprising at least one organic light-emitting diode according to claim 38.

* * * * *